US009212216B2

(12) United States Patent
Godfroid et al.

(10) Patent No.: US 9,212,216 B2
(45) Date of Patent: Dec. 15, 2015

(54) **IDENTIFICATION AND MOLECULAR CHARACTERISATION OF PROTEINS, EXPRESSED IN THE *IXODES RICINUS* SALIVARY GLANDS**

(71) Applicant: Bioxodes SPRL, Brussels (BE)

(72) Inventors: Edmond Godfroid, Brussels (BE); Yves Decrem, Ohain (BE); Luc Vanhamme, Court-Saint-Etienne (BE); Alex Bollen, Itterbeek (BE); Gerard Leboulle, Brussels (BE)

(73) Assignee: BIOXODES SA, Marche-en-Famenne (BE)

( * ) Notice: Subject to any disclaimer, the term of this patent is extended or adjusted under 35 U.S.C. 154(b) by 0 days.

(21) Appl. No.: 14/302,862

(22) Filed: Jun. 12, 2014

(65) Prior Publication Data
US 2014/0357566 A1 Dec. 4, 2014

Related U.S. Application Data

(60) Division of application No. 13/632,763, filed on Oct. 1, 2012, now abandoned, which is a continuation of application No. 11/932,985, filed on Oct. 31, 2007, now Pat. No. 8,277,813.

(51) Int. Cl.
| | |
|---|---|
| *A61K 38/00* | (2006.01) |
| *A61K 39/00* | (2006.01) |
| *A61K 39/002* | (2006.01) |
| *A61K 39/38* | (2006.01) |
| *C07K 1/00* | (2006.01) |
| *C07K 14/00* | (2006.01) |
| *C07K 17/00* | (2006.01) |
| *C07K 14/81* | (2006.01) |
| *C07K 14/435* | (2006.01) |
| *C07K 16/38* | (2006.01) |
| *C07K 16/18* | (2006.01) |
| *A61K 38/57* | (2006.01) |
| *C12N 9/99* | (2006.01) |

(52) U.S. Cl.
CPC .............. *C07K 14/8114* (2013.01); *A61K 38/57* (2013.01); *A61K 39/0003* (2013.01); *C07K 14/43527* (2013.01); *C07K 14/811* (2013.01); *C07K 16/18* (2013.01); *C07K 16/38* (2013.01); *C12N 9/99* (2013.01); *A61K 38/00* (2013.01); *A61K 2121/00* (2013.01)

(58) Field of Classification Search
None
See application file for complete search history.

(56) References Cited

U.S. PATENT DOCUMENTS

| 8,277,813 B2 | 10/2012 | Godfroid |
| 2008/0219970 A1 | 9/2008 | Godfroid et al. |

FOREIGN PATENT DOCUMENTS

| WO | WO 95/04750 | 2/1995 |
| WO | WO 00/77198 | 12/2000 |

OTHER PUBLICATIONS

U.S. Office Action dated Apr. 4, 2010 cited in U.S. Appl. No. 11/932,985.
U.S. Office Action dated Nov. 2, 2010 cited in U.S. Appl. No. 11/932,985.
U.S. Office Action dated Dec. 15, 2012 cited in U.S. Appl. No. 11/932,985.
Abaza et al. 'Effects of amino acid substitutions outside an antigenic site on protein binding to monoclonal antibodies of predetermined specificity obtained by peptide immunization: demonstration with region 94-100 (antigenic site 3) of myoglobin.' J. Prot. Chem. 11 (5):433-444, 1992.
Bergman, D.K., et al., (2000) Isolation and molecular closing of a secreted immunosuppressant protein from dermacentor andersoni salivary gland, J. Parasitol; 86(3):516-525.
Brossard, M., et al. (1997) Immunology of Interactions Between Ticks and Hosts, Medical and Veterinary Entomology, 11:270-276.
Colman et al. 'Effects of amino acid sequence changes on antibody-antigen interactions.' Research in Immunology 145(1 ):33-36, 1994.
Colman, Research in Immunology, vol. 145, 1994, pp. 33-36.
Das, et al. (2000) SALP16, A Gene Induced in Ixodes Scapularis Salivery Glands During Tick Feeding, Am. J. Trop. Med. Hyg. 62(1) 99-105.
De Silva, N.M., (1995) Growth and Migration of Borrelia Burgdorferi in Ixodes Ticks During Blood Feeding, Am. J. Trop. Med, Hyg., 53(4):397-404.
Decrem et al. 'Ir-CPI, a coagulation contact phase inhibitor from the tick Ixodes ricinus, inhibits thrombus formation without impairing hemostasis.' J. Exp. Med. 206(11 ):2381-2395, 2009.
Frohman, M.A., et al. (1988) Rapid production of full-length cDNAs from rate transcripts: Amplification using a single gene-specific oligonucleotide primer, Proc. Natl. Acad. Sci., USA 85:8998-9002.
Fuchsberger, N. et al., (1995) Ixodid tick salivary gland extracts inhibit production of lipopolysaccharide-induced mRNA of several different human cytokines, Experimental & Applied Acarology; 19:671-676.
Ganapamo, F., et al. (1995) in vitro production of Interleukin-4 and Interferon-y by lymph node cells from BALB/c mice infested with nymphal Ixodes ricinus ticks, Immunology, 85:120-124.

(Continued)

*Primary Examiner* — Nora Rooney
(74) *Attorney, Agent, or Firm* — Merchant & Gould P.C.

(57) ABSTRACT

The invention relates to a new polynucleotide which encodes a polypeptide expressed in the salivary glands of ticks, more particularly the *Ixodes ricinus* arthropod tick, during the slow-feeding phase of the blood meal have, said polynucleotide and related polypeptide may be used in different constructions and for different applications which are also included in the present invention.

19 Claims, 11 Drawing Sheets

(56) References Cited

OTHER PUBLICATIONS

Ganapamo, F., et al. (1996) Immunosuppression and cytokine production in mice infected with Ixodes ricinus ticks: a possible role of laminin and interleukin-10 on the in vitro responsiveness of lymphocytes to mitogens, Immunology, 87:259-263.

Ganapamo, F., et al. (1997) Identification of an Ixodes ricinus salivary gland fraction through its ability to stimulate CD4 T cells present in BALB/c mice lymph nodes draining the tick fixation site, Parasitology, 775:91-96.

Hubank, M., et al. (1994) Identifying differences in mRNA expression by representational difference analysis of cDNA, Nucleic Acids Research, 22(25):5640-5648.

Kopecly, J., et al. (1998) Suppresive effect of Ixodes ricinus salivary gland extract on mechanisms of natural immunity In Vitro, Parasite Immuniology, 20:169-174.

Kuby et al. 'Immunology.' Fourth Edition, Chapter 18: 449-465, 2000.

Leboulle et al. 'Isolation of Ixodes ricinus salivary gland mRNA encoding factors induced during blood feeding.' Am. J. Trop. Med. Hyg. 66(3):225-233, 2002.

Lederman et al. 'A single amino acid substitution in a common African allele of the CD4 molecule ablates binding of the monoclonal antibody, OKT4.' Molec. Immunol. 28:1171-1181, 1991.

Luo, et al. (1997) Cloning and sequence of a gene for the homologue of the stearoly CoA desaturase from salivary glands of the tick Amblyomma americanum, Insect Molecular Biology, 6(3): 267-271.

Metzler et al. 'Solution structure of human CTLA-4 and delineation of a CD80/CD86 binding site conserved in CD28.' Nature Structural Biol. 4:527-531,1997.

Needham, et al. (1989) Characterization of Ixodid Tick Salivery-Gland Gene Products, Using Recombinant DNA Technology, Experimental & Applied Acarology, 7:21-32.

Ngo et al., The protein folding problem and teriary structure prediction, 1994, pp. 492-495, Birkhauser press.

Porter et al., Biochem. J., 2005, 386; 15-27.

Ramachandra R.N., et al. (1992) Modulaton of host0immune responses by ticks (Acari:Ixodidae): effect of salivary gland extracts on host macrophages and lynphocyte cytokine productions, J. Med. Entomol., 29(5):818-828.

Sauer, J.R. et al. (1995) Tick Salivery Gland Physiology, Ann. Rev. Entomol., 40:245-267.

Schoeler, G.B., et al. (2000) Influence of soluble proteins from the salivary glands of ixodes ticks on the in-vitro proliferative responses of lymphocytes from BALB/c and C3H/HeN mice, Ann. Trop. Med. Parasitol., 94(5):507-518.

Skolnick et al., TIBTECH, vol. 18, pp. 34-39, 2000.

Skolnick et al., Trends in Biotechnology, 2000, 18(1) 34-39.

Urioste, S., et al. (1994) Saliva of the Lyme Disease Vector, Ixodes dammini, Blocks Cell Activation by a Nonprostaglandin E2-dependent Mechanism, I. Exp. Med. 180:1077-1085.

Wang, H., et al. (1994) Excretion of host immunoglobulin in tick saliva and detection if IgG-binding proteins in tick haemolymph and salivary glands, Parasitology, 109:525-530.

Whisstock et al., Quarterly Reviews of Biophysics, 2003, 36:307-340.

Wikel, S. K. (1996) Host Immunity to Ticks, Annu. Rev. Entomol, 41:1-22.

Zeidner, et al. (1996) Suppression of Acute Icodes scapularis-induced Borrelia burgdorferi infection using Tumor Necroses Factor-a, Interleukin-2 and Interferon-y, J. Infect. Diseases, 173:187-195.

International Search Report from PCT/BE00/00061 filed Aug. 6, 2000.

SEQUENCE LISTING

<160> NUMBER OF SEQ ID NOS: 46

<210> SEQ ID NO 1
<211> LENGTH: 194
<212> TYPE: DNA
<213> ORGANISM: Ixodes ricinus

<400> SEQUENCE: 1

```
atacctteca cttgtagece ttcctcatcc gatatggtga cggatgccat tgcatcctcg    60
tcgtggaaga ggtcctcttc taaataagac ccatccatat atgtgtgttt gcgaatgccg   120
tcgacgtagc tcctgactag aaactcgtcg gctaggacag aacttttctt caggtttagc   180
gtaatgtcct cgtt                                                     194
```

<210> SEQ ID NO 2
<211> LENGTH: 607
<212> TYPE: DNA
<213> ORGANISM: Ixodes ricinus
<220> FEATURE:
<221> NAME/KEY: misc_feature
<222> LOCATION: (5)..(5)
<223> OTHER INFORMATION: n = A,T,C or G
<220> FEATURE:
<221> NAME/KEY: misc_feature
<222> LOCATION: (333)..(333)
<223> OTHER INFORMATION: n = A,T,C or G
<220> FEATURE:
<221> NAME/KEY: misc_feature
<222> LOCATION: (555)..(555)
<223> OTHER INFORMATION: n = A,T,C or G

<400> SEQUENCE: 2

```
taccngggaa tccaaaacca atttttattg gaacttccac gtcttcttca aggcggtggc    60
acctctgcat ttatgaagtt cgtcttggca ttttattttt tgcttctttc attgcrgaac   120
tcgcaaatgc acttcccgtg cttgtcgcat ttcgccccaa aagcgcatgg cattccttcc   180
ggcagattaa cttttttcaaa ttcacggttc tgaaccaata atagatcgtg gcaatgtttg   240
tgctgtttgc gatttgcaaa ccagctgtag ccaccattgg actcaaaggt gcgcacaaca   300
tggcgccgaa ctgtgaaaaa caaattaagg ctncttttgta ataacgctag tcttggtacg   360
ccgttagagg tcgatgtcgc gcctcgcgat tgcaaagtca cttgcactta tcaagctcct   420
ggagaaaaat gggtgcaacg gggggatcag cgtttgtact tgcaaacatt tgtgagacg    480 gtaaaccwgt atttcgcgga actcagatgc tccagcgtga agctcgtctt aataaaagtt   540
gtaaattcga gtatngatga agaactgaaa ttcgaggcat ttagaaacac cacgagaagc   600
agcggaa                                                             607
```

<210> SEQ ID NO 3
<211> LENGTH: 259
<212> TYPE: DNA
<213> ORGANISM: Ixodes ricinus

<400> SEQUENCE: 3

```
gatcctacgc ctgaaaatga gtgtccatcg tcttcacata gtgccacatt gtaattggta    60
caagctccat tttcgtcagc gctgtttgtt atgctgccgc ctactttttcc ttcggcactc   120 cataagttaa accctgtcat tataagtgtg attgccgtat ctcggctgaa tgggttccat   180
ttttctctta aataatcacg tgtccatatt ccatgtattg tgttcatgag tatgtgattc   240
tcatcgtata tcttcgcct                                                259
```

<210> SEQ ID NO 4
<211> LENGTH: 170
<212> TYPE: DNA
<213> ORGANISM: Ixodes ricinus

<400> SEQUENCE: 4

```
ccactcgaaa atggaggctt tgaaacattt cagtacccct gtgaactctg gctttgcaat    60
gtaacagcaa aaacacttac agttgaaggg tgcagtgtca gacgctatgg aagttgcatc   120
cacgagcacr accctgatta ctactggcca cgttgctrtc cgggtcgtcc              170
```

<210> SEQ ID NO 5
<211> LENGTH: 168
<212> TYPE: DNA
<213> ORGANISM: Ixodes ricinus

<400> SEQUENCE: 5

```
gtatgttacc atgtccaacc cggttattaa ataccaag tcgtaggatt tgtaggcagc    60
tgcattgccc ttgacgtact ctctcaacgt tgccaaggac tcaggcccat aaatgtagtg   120
gggttgacct tgaactcttc gtaaaaagcg ttctttctcc gtcgtgag                168
```

<210> SEQ ID NO 6
<211> LENGTH: 247
<212> TYPE: DNA
<213> ORGANISM: Ixodes ricinus

<400> SEQUENCE: 6

```
ccgaamataa aacttagtct caccaatata cgtttgccta acgcgaagga acaggcacaa    60
atatactacg agcacgacat tctcaagaac acggttcacg gagtgtggac gagaattcac   120
tcaaaatatc cgttccctga agatgaggga attcactga taatgacagg gtttgattta   180
tggagtgccg atttaactgt aggcggcacc ataacaaaca gcgctgagaa aagcggagct   240
tgtacga                                                              247
```

<210> SEQ ID NO 7
<211> LENGTH: 261
<212> TYPE: DNA
<213> ORGANISM: Ixodes ricinus
<220> FEATURE:
<221> NAME/KEY: CDS
<222> LOCATION: (1)..(261)

<400> SEQUENCE: 7

```
atg cct ttt att ttc gtg gtg agc tta gtc att gtg gcc tgc atc gtg     48
Met Pro Phe Ile Phe Val Val Ser Leu Val Ile Val Ala Cys Ile Val
1               5                   10                  15 gta gac aca gcc aac cac aaa ggt aga ggg cgg cct gcg aag tgt aaa     96
Val Asp Thr Ala Asn His Lys Gly Arg Gly Arg Pro Ala Lys Cys Lys
            20                  25                  30 ctt cct ccg gac gac gga cca tgc aga gca cga att ccg agt tac tac    144
Leu Pro Pro Asp Asp Gly Pro Cys Arg Ala Arg Ile Pro Ser Tyr Tyr
        35                  40                  45 ttt gat aga aaa acc aaa acg tgc aag gag ttt atg tat ggc gga tgc    192
Phe Asp Arg Lys Thr Lys Thr Cys Lys Glu Phe Met Tyr Gly Gly Cys
    50                  55                  60 gaa gga aac gaa aac aat ttt gaa aac ata act acg tgc caa gag gaa    240
Glu Gly Asn Glu Asn Asn Phe Glu Asn Ile Thr Thr Cys Gln Glu Glu
65                  70                  75                  80 tgc aga gca aaa aaa gtc tag                                         261
Cys Arg Ala Lys Lys Val
                85
```

<210> SEQ ID NO 8
<211> LENGTH: 86
<212> TYPE: PRT
<213> ORGANISM: Ixodes ricinus

<400> SEQUENCE: 8

```
Met Pro Phe Ile Phe Val Val Ser Leu Val Ile Val Ala Cys Ile Val
1               5                   10                  15

Val Asp Thr Ala Asn His Lys Gly Arg Gly Arg Pro Ala Lys Cys Lys
            20                  25                  30

Leu Pro Pro Asp Asp Gly Pro Cys Arg Ala Arg Ile Pro Ser Tyr Tyr
        35                  40                  45

Phe Asp Arg Lys Thr Lys Thr Cys Lys Glu Phe Met Tyr Gly Gly Cys
    50                  55                  60

Glu Gly Asn Glu Asn Asn Phe Glu Asn Ile Thr Thr Cys Gln Glu Glu
65                  70                  75                  80

Cys Arg Ala Lys Lys Val
                85
```

<210> SEQ ID NO 9
<211> LENGTH: 292
<212> TYPE: DNA
<213> ORGANISM: Ixodes ricinus

<400> SEQUENCE: 9

```
catcgmagcc atagtatatt ttgcacttgt cttccgtttc gtcgtagtag gaccgattcc      60
acattgtagt acaccagtca cttatatcct gcgggcggtg cttgcatttg tcctgaacaa     120
atcttccaca gcgcttgtcg cacgcctcct gggaatagaa cgcgttctct cctccgcatc     180
tccatttgga atcatagaaa catctttcag tttgaatatt gtagcgataa taatcggtat     240
cagtttcttt gcatggtcct gggaggggtt tggcgcaggg gccgtattca gg             292
```

<210> SEQ ID NO 10
<211> LENGTH: 270
<212> TYPE: DNA
<213> ORGANISM: Ixodes ricinus

<400> SEQUENCE: 10

```
ggtaatagtt gtcaaattcc attaatgtat cctgaaatgt gaccatatct ttgtttcccc      60
tgtaaaatct cataaaaggc tgtgtgtttt ccttaagaag tgtaacagcc acgatggtca     120
atctcacgga tggatgtgtg acacttttat atctcaggtt tgccgacatt gccattacag     180
ataaatagtt gataatttct ttcttgttat agttgtaagc agcgcatgtt gttgcatcaa     240
gcaccacatg cacttcaggc aatatggttt                                      270
```

<210> SEQ ID NO 11
<211> LENGTH: 316
<212> TYPE: DNA
<213> ORGANISM: Ixodes ricinus

<400> SEQUENCE: 11

```
agaaagcagt catattggcc atccacaggt cacaatggtt ctctccttga cctggcatcg      60
ggattcgaag tatggtgcag ttcacgtagt tggaatacaa cacgaaatgt gttcgttggt     120
acgccaatag gggttctcgc aaagaacata tcatttggag gaaggcgtag tccgtcgaga     180
tatcccaaaa ctagggtttc attgcgtgcg aaccaactgc ccccacttct gtatgtgtac     240
```

```
tgtaaggagt rgttgaacgg ygtcctctttt cccataaccct tgaagttttc acactgcaga    300
ggattacctc tcaaaa                                                      316
```

```
<210> SEQ ID NO 12
<211> LENGTH: 241
<212> TYPE: DNA
<213> ORGANISM: Ixodes ricinus

<400> SEQUENCE: 12
aaggtagcaa gggtggtagg cttttcctcac aaagagtctg gcttccgtga taaccatatc     60
cattcctcac cgtatacccg tcatccaacg tcaattgtgt tacaaggcag ataatgtcaa    120
aatggctctg gtccctataa tagtcggata atgtagaaat cgctccatgt ggccaaatag    180
atgttcctct ttcatactgt tttaacttta attgtaggtc cgcctcgttc tcgaggtatg    240
t                                                                    241
```

```
<210> SEQ ID NO 13
<211> LENGTH: 636
<212> TYPE: DNA
<213> ORGANISM: Ixodes ricinus
<220> FEATURE:
<221> NAME/KEY: misc_feature
<222> LOCATION: (7)..(7)
<223> OTHER INFORMATION: n = A,T,C or G
<220> FEATURE:
<221> NAME/KEY: misc_feature
<222> LOCATION: (22)..(23)
<223> OTHER INFORMATION: n = A,T,C or G
<220> FEATURE:
<221> NAME/KEY: misc_feature
<222> LOCATION: (37)..(37)
<223> OTHER INFORMATION: n = A,T,C or G
<220> FEATURE:
<221> NAME/KEY: misc_feature
<222> LOCATION: (572)..(572)
<223> OTHER INFORMATION: n = A,T,C or G

<400> SEQUENCE: 13
ttccccnaat tggccttgcg anncttgcaa gtcgacncta gaggctccga agatggacag     60
attgcgcatg aaatatttga atcgagcag aatggtgatt ttaggagcga ttatattgtg    120
ccacccagtt tgaaagtgca agaacgcaca gtggtttacc gtaacaagta caccagagtt    180
cctgtaaatt ttaccgtcga agttgccatg ctgattgata agtatttata cwaggagttc    240
aagaacgaga gccacatcgt accgtacctg gctatgatac tgactttgat aaatctgagg    300
tatgccgaca cacatgaccc gtacatccag tttcttctca cacaagtgtt cgtggggaaw    360
wctggcgatc atatgggcca catgcccttc cgacgagcgt tcttgttcag gcgccggcat    420
tatgcgcagt ttaggcccaa tmacaccttc cacttgtaat tctccgttgt tggatagtgt    480
aagtgaggcc attgcatcag catcgtggaa gargccttcc tccaagtagg aaccgcccat    540
ttaggtttgc tttcccaatc cgccaattta antttaaaa aaaattcccc ccccaaaat     600 taatttttt taaaggtgga ttgtgatttc tccgtt                              636
```

```
<210> SEQ ID NO 14
<211> LENGTH: 432
<212> TYPE: DNA
<213> ORGANISM: Ixodes ricinus

<400> SEQUENCE: 14
gatcccaaaa gtgccctgg arcgacggtt acatcatgag ctacgtcata aacttcaaaa      60
accacttcaa attttctccc tgctgtgtag aatcaattcg attcgtcgca cgagagcggg    120
```

```
actgcctcta caaagtcaat gccaaggatg ctgtaaaaag cctaatatct ctgcccggat    180
ttaggatatc gccaacgagt ttctgtcaat ttatgcatcc gctttaccgc ggtgtccata    240
gcgataagaa agcaggtctg tccgattgcg tacagacgtg tagaacggcc aaaaatcgac    300
gaggaggcta ccattcatgg attcacgcgg cacttgacgg ggttccttgc gacaagagaa    360
accccaagaa ggcctgcata acgggaaatg cacccctcct aagagcatg ccccacagaa     420 cgtaccggga at                                                        432

<210> SEQ ID NO 15
<211> LENGTH: 466
<212> TYPE: DNA
<213> ORGANISM: Ixodes ricinus

<400> SEQUENCE: 15
agggcgttct ttgcttyaca gggaacrgca tatgggccac gtgaccttcc aatgaccgct     60
ccaaatctgg cataggttga aytcgcaagt cgtggcgcag caggcctycc acattcactc    120
catcctcgtc ttttaggatg actgccgcca tttgttttgt atcgtggtac aggtgtttgt    180
tatggtccga gccgtcgaca taagtattga ccaacgatcg gccgaatgat tacggctcac    240
caaacacatc aaataccccc gtcaagtcaa gagctggaag cacaaagcat agtatgtaca    300
agataccctt ggaaatcttt cccgaagttc accttgtggt ggacagcaca tttgccaaag    360
cttttaaatt tgacgtgtac aaagtaacgc gttacttcgc agtgcttaca aatgcggcta    420
atcttaggta tgccagcttc gtatttccaa aagtacagct caggat                   466

<210> SEQ ID NO 16
<211> LENGTH: 377
<212> TYPE: DNA
<213> ORGANISM: Ixodes ricinus

<400> SEQUENCE: 16
ctcgtccaca cattctccta aaatgcaagc cttttttttc ccacaaggtg taccgtcgac     60
tacactgagt ctccaataaa tatgttttcc ggtgcaattt accttgcagt ctttgacgcc    120
gtatgtaggg tcagcgtgca tgccttcgtc gtacatatac accctctgac agtagttgct    180
cagtgttgtc atcctaccag gaagcttaga cgaacgtttt attgttttg tcgtgtatcg     240 ttctctaagg catttgaatt ccggacggtt gtagaggttc ctgacttctc gctggcagca    300
ataagagaac tgatactggc gctcgtcttg catcttgtaa ctcatgaggt atccgtcatc    360
ccatgggcag tccgcag                                                   377

<210> SEQ ID NO 17
<211> LENGTH: 1670
<212> TYPE: DNA
<213> ORGANISM: Ixodes ricinus
<220> FEATURE:
<221> NAME/KEY: CDS
<222> LOCATION: (54)..(1520)

<400> SEQUENCE: 17
aaggaagaag ttaggcgtag gctttgggaa accggtcatc ctcgaaacca gag atg       56
                                                           Met
                                                             1 tcg gga ctc agc ctg aaa ttg tgg att gta gcg ttc ttt tct ttc tgc     104
Ser Gly Leu Ser Leu Lys Leu Trp Ile Val Ala Phe Phe Ser Phe Cys
          5                  10                  15
```

-continued

| | |
|---|---|
| ttg gcc gag aaa gag cat ggg atc gtg tac ccc agg atg ctt gaa agc<br>Leu Ala Glu Lys Glu His Gly Ile Val Tyr Pro Arg Met Leu Glu Ser<br>     20                   25                 30 | 152 |
| aga gca gca act gga gag aga atg ctt aaa atc aac gat gac ctg acg<br>Arg Ala Ala Thr Gly Glu Arg Met Leu Lys Ile Asn Asp Asp Leu Thr<br>35                   40                 45 | 200 |
| ttg acg ctg cag aag agt aag gtc ttc gct gac gac ttt ctc ttc agc<br>Leu Thr Leu Gln Lys Ser Lys Val Phe Ala Asp Asp Phe Leu Phe Ser<br>50               55                 60                 65 | 248 |
| acg acc gac gga att gaa cct att gat tac tac atc aaa gcc gaa gac<br>Thr Thr Asp Gly Ile Glu Pro Ile Asp Tyr Tyr Ile Lys Ala Glu Asp<br>               70                 75                 80 | 296 |
| gct gaa cgt gac atc tac cac gac gca act cac atg gca tca gta agg<br>Ala Glu Arg Asp Ile Tyr His Asp Ala Thr His Met Ala Ser Val Arg<br>                   85                 90               95 | 344 |
| gta acg gac gat gat ggc gtg gaa gtg gaa gga att ctt gga gag agg<br>Val Thr Asp Asp Asp Gly Val Glu Val Glu Gly Ile Leu Gly Glu Arg<br>                 100               105             110 | 392 |
| ctt cgt gtt aaa cct ttg ccg gca atg gcc cgc agc agc gat ggc ctc<br>Leu Arg Val Lys Pro Leu Pro Ala Met Ala Arg Ser Ser Asp Gly Leu<br>115                 120                 125 | 440 |
| aga ccg cat atg ttg tac gaa gtc gac gca cac gaa aac ggc cgg cca<br>Arg Pro His Met Leu Tyr Glu Val Asp Ala His Glu Asn Gly Arg Pro<br>130                 135                 140               145 | 488 |
| cat gat tat ggt tca ccg aac aca aca aat acc ccc gta gag aga aga<br>His Asp Tyr Gly Ser Pro Asn Thr Thr Asn Thr Pro Val Glu Arg Arg<br>                 150               155               160 | 536 |
| gct gga ggc aca gaa ccc cag atg tac aag ata cca gcg gaa atc tat<br>Ala Gly Gly Thr Glu Pro Gln Met Tyr Lys Ile Pro Ala Glu Ile Tyr<br>165                 170                 175 | 584 |
| ccc gaa gtt tac ctt gtg gcg gat agt gcc ttt gcc aaa gaa ttt aac<br>Pro Glu Val Tyr Leu Val Ala Asp Ser Ala Phe Ala Lys Glu Phe Asn<br>                 180               185             190 | 632 |
| ttt gat gtg aac gcc gtt acg cgt tac ttc gca gtg ctt aca aat gcg<br>Phe Asp Val Asn Ala Val Thr Arg Tyr Phe Ala Val Leu Thr Asn Ala<br>195                 200                 205 | 680 |
| gct aat ctt agg tat gaa agc ttc aaa tct cca aag gta cag ctc agg<br>Ala Asn Leu Arg Tyr Glu Ser Phe Lys Ser Pro Lys Val Gln Leu Arg<br>210                 215                 220               225 | 728 |
| atc gtt ggc ata acg atg aac aaa aac cca gca gac gag cca tac att<br>Ile Val Gly Ile Thr Met Asn Lys Asn Pro Ala Asp Glu Pro Tyr Ile<br>                 230               235               240 | 776 |
| cac aat ata cgg gga tat gag cag tac cgg aat att ttg ttt aag gaa<br>His Asn Ile Arg Gly Tyr Glu Gln Tyr Arg Asn Ile Leu Phe Lys Glu<br>245                 250                 255 | 824 |
| aca ctg gag gat ttc aac act cag atg aag tca aaa cat ttt tat cgt<br>Thr Leu Glu Asp Phe Asn Thr Gln Met Lys Ser Lys His Phe Tyr Arg<br>                 260               265             270 | 872 |
| act gcc gat atc gtg ttt ctc gtg aca gca aaa aat atg tcc gaa tgg<br>Thr Ala Asp Ile Val Phe Leu Val Thr Ala Lys Asn Met Ser Glu Trp<br>275                 280                 285 | 920 |
| gtt ggt agc aca cta caa tca tgg act ggc ggg tac gct tac gta gga<br>Val Gly Ser Thr Leu Gln Ser Trp Thr Gly Gly Tyr Ala Tyr Val Gly<br>290                 295                 300               305 | 968 |
| aca gcg tgt tcc gaa tgg aaa gta gga atg tgt gaa gac cga ccg aca<br>Thr Ala Cys Ser Glu Trp Lys Val Gly Met Cys Glu Asp Arg Pro Thr<br>                 310               315               320 | 1016 |
| agc tat tac gga gct tac gtt ttc gcc cat gag ctg gcg cat aat ttg<br>Ser Tyr Tyr Gly Ala Tyr Val Phe Ala His Glu Leu Ala His Asn Leu<br>325                 330                 335 | 1064 |

| | | | | | | | | | | | | | | | | |
|---|---|---|---|---|---|---|---|---|---|---|---|---|---|---|---|---|
| ggt | tgt | caa | cac | gat | gga | gat | ggt | gcc | aat | agc | tgg | gtg | aaa | ggg | cac | 1112 |
| Gly | Cys | Gln | His | Asp | Gly | Asp | Gly | Ala | Asn | Ser | Trp | Val | Lys | Gly | His | |
| | | | 340 | | | | 345 | | | | 350 | | | | | |
| atc | gga | tct | gcg | gac | tgc | cca | tgg | gat | gac | gga | tac | ctt | atg | agc | tac | 1160 |
| Ile | Gly | Ser | Ala | Asp | Cys | Pro | Trp | Asp | Asp | Gly | Tyr | Leu | Met | Ser | Tyr | |
| 355 | | | | | 360 | | | | | 365 | | | | | | |
| aag | atg | gaa | gac | gag | cgc | cag | tat | aag | ttt | tct | ccc | tac | tgc | cag | aga | 1208 |
| Lys | Met | Glu | Asp | Glu | Arg | Gln | Tyr | Lys | Phe | Ser | Pro | Tyr | Cys | Gln | Arg | |
| 370 | | | | | 375 | | | | | 380 | | | | | 385 | |
| gaa | gtc | agg | aac | ctc | tac | agg | cgt | ccg | gaa | ttc | aaa | tgc | ctc | act | gaa | 1256 |
| Glu | Val | Arg | Asn | Leu | Tyr | Arg | Arg | Pro | Glu | Phe | Lys | Cys | Leu | Thr | Glu | |
| | | | | 390 | | | | | 395 | | | | | 400 | | |
| cga | aaa | gcg | aaa | aaa | aca | atc | cgc | tcg | tct | aag | cta | cct | ggt | gtg | atg | 1304 |
| Arg | Lys | Ala | Lys | Lys | Thr | Ile | Arg | Ser | Ser | Lys | Leu | Pro | Gly | Val | Met | |
| | | | 405 | | | | 410 | | | | | 415 | | | | |
| aca | tca | tcg | agc | aac | tat | tgc | cgg | agg | gtg | tac | atg | tac | gaa | aaa | ggc | 1352 |
| Thr | Ser | Ser | Ser | Asn | Tyr | Cys | Arg | Arg | Val | Tyr | Met | Tyr | Glu | Lys | Gly | |
| | | 420 | | | | | 425 | | | | | 430 | | | | |
| atg | cac | gcc | gac | gag | gca | tat | ggc | gtc | aag | gac | tgc | agg | gta | aaa | tgc | 1400 |
| Met | His | Ala | Asp | Glu | Ala | Tyr | Gly | Val | Lys | Asp | Cys | Arg | Val | Lys | Cys | |
| 435 | | | | | 440 | | | | | 445 | | | | | | |
| acc | acc | aca | tca | aga | atg | tat | tgg | cta | ctc | ggt | gta | gtc | gac | ggt | aca | 1448 |
| Thr | Thr | Thr | Ser | Arg | Met | Tyr | Trp | Leu | Leu | Gly | Val | Val | Asp | Gly | Thr | |
| 450 | | | | | 455 | | | | | 460 | | | | | 465 | |
| cct | tgc | gga | aat | gga | aag | gct | tgc | att | ctt | ggg | aaa | tgc | agg | aac | aaa | 1496 |
| Pro | Cys | Gly | Asn | Gly | Lys | Ala | Cys | Ile | Leu | Gly | Lys | Cys | Arg | Asn | Lys | |
| | | | | 470 | | | | | 475 | | | | | 480 | | |
| atc | aaa | ata | agc | aag | aag | gac | tga | gaggttgata | atatcaaatt | aatcatgata | | | | | | 1550 |
| Ile | Lys | Ile | Ser | Lys | Lys | Asp | | | | | | | | | | |
| | | | | 485 | | | | | | | | | | | | | tttcaaccac atgacttcgt gctcaactgg tagccccaaa taaatttttaa aaaaaatccc    1610 aatatgcgtg gtagaaaaag cagcaaacaa taaaacttct aaaaatgtct tgcaaaaatg    1670

<210> SEQ ID NO 18
<211> LENGTH: 488
<212> TYPE: PRT
<213> ORGANISM: Ixodes ricinus

<400> SEQUENCE: 18

Met Ser Gly Leu Ser Leu Lys Leu Trp Ile Val Ala Phe Phe Ser Phe
1               5                   10                  15

Cys Leu Ala Glu Lys Glu His Gly Ile Val Tyr Pro Arg Met Leu Glu
                20                  25                  30

Ser Arg Ala Ala Thr Gly Glu Arg Met Leu Lys Ile Asn Asp Asp Leu
            35                  40                  45

Thr Leu Thr Leu Gln Lys Ser Lys Val Phe Ala Asp Phe Leu Phe
        50                  55                  60

Ser Thr Thr Asp Gly Ile Glu Pro Ile Asp Tyr Tyr Ile Lys Ala Glu
65                  70                  75                  80

Asp Ala Glu Arg Asp Ile Tyr His Asp Ala Thr His Met Ala Ser Val
                85                  90                  95

Arg Val Thr Asp Asp Gly Val Glu Val Glu Gly Ile Leu Gly Glu
            100                 105                 110

Arg Leu Arg Val Lys Pro Leu Pro Ala Met Ala Arg Ser Ser Asp Gly
        115                 120                 125

Leu Arg Pro His Met Leu Tyr Glu Val Asp Ala His Glu Asn Gly Arg
    130                 135                 140

```
Pro His Asp Tyr Gly Ser Pro Asn Thr Thr Asn Thr Pro Val Glu Arg
145                 150                 155                 160

Arg Ala Gly Gly Thr Glu Pro Gln Met Tyr Lys Ile Pro Ala Glu Ile
                165                 170                 175

Tyr Pro Glu Val Tyr Leu Val Ala Asp Ser Ala Phe Ala Lys Glu Phe
            180                 185                 190

Asn Phe Asp Val Asn Ala Val Thr Arg Tyr Phe Ala Val Leu Thr Asn
        195                 200                 205

Ala Ala Asn Leu Arg Tyr Glu Ser Phe Lys Ser Lys Val Gln Leu
210                 215                 220

Arg Ile Val Gly Ile Thr Met Asn Lys Asn Pro Ala Asp Glu Pro Tyr
225                 230                 235                 240

Ile His Asn Ile Arg Gly Tyr Glu Gln Tyr Arg Asn Ile Leu Phe Lys
                245                 250                 255

Glu Thr Leu Glu Asp Phe Asn Thr Gln Met Lys Ser Lys His Phe Tyr
            260                 265                 270

Arg Thr Ala Asp Ile Val Phe Leu Val Thr Ala Lys Asn Met Ser Glu
        275                 280                 285

Trp Val Gly Ser Thr Leu Gln Ser Trp Thr Gly Gly Tyr Ala Tyr Val
290                 295                 300

Gly Thr Ala Cys Ser Glu Trp Lys Val Gly Met Cys Glu Asp Arg Pro
305                 310                 315                 320

Thr Ser Tyr Tyr Gly Ala Tyr Val Phe Ala His Glu Leu Ala His Asn
                325                 330                 335

Leu Gly Cys Gln His Asp Gly Asp Gly Ala Asn Ser Trp Val Lys Gly
            340                 345                 350

His Ile Gly Ser Ala Asp Cys Pro Trp Asp Asp Gly Tyr Leu Met Ser
        355                 360                 365

Tyr Lys Met Glu Asp Glu Arg Gln Tyr Lys Phe Ser Pro Tyr Cys Gln
370                 375                 380

Arg Glu Val Arg Asn Leu Tyr Arg Arg Pro Glu Phe Lys Cys Leu Thr
385                 390                 395                 400

Glu Arg Lys Ala Lys Lys Thr Ile Arg Ser Ser Lys Leu Pro Gly Val
                405                 410                 415

Met Thr Ser Ser Ser Asn Tyr Cys Arg Arg Val Tyr Met Tyr Glu Lys
            420                 425                 430

Gly Met His Ala Asp Glu Ala Tyr Gly Val Lys Asp Cys Arg Val Lys
        435                 440                 445

Cys Thr Thr Thr Ser Arg Met Tyr Trp Leu Leu Gly Val Val Asp Gly
450                 455                 460

Thr Pro Cys Gly Asn Gly Lys Ala Cys Ile Leu Gly Lys Cys Arg Asn
465                 470                 475                 480

Lys Ile Lys Ile Ser Lys Lys Asp
                485

<210> SEQ ID NO 19
<211> LENGTH: 158
<212> TYPE: DNA
<213> ORGANISM: Ixodes ricinus

<400> SEQUENCE: 19
caccagtgat gcttattgtt gcactgcact tgttgataat atccggtcgt cgaattgcac      60
ttcggaactt ccactccaac ttggcgagcc gtggattttg acttctcgtg atgctccacc     120
agacagttgc aggacttcag ctgcctagat ggagcctt                              158
```

```
<210> SEQ ID NO 20
<211> LENGTH: 146
<212> TYPE: DNA
<213> ORGANISM: Ixodes ricinus
<220> FEATURE:
<221> NAME/KEY: misc_feature
<222> LOCATION: (41)..(41)
<223> OTHER INFORMATION: n = A,T,C or G
<220> FEATURE:
<221> NAME/KEY: misc_feature
<222> LOCATION: (60)..(60)
<223> OTHER INFORMATION: n = A,T,C or G
<220> FEATURE:
<221> NAME/KEY: misc_feature
<222> LOCATION: (104)..(104)
<223> OTHER INFORMATION: n = A,T,C or G
<220> FEATURE:
<221> NAME/KEY: misc_feature
<222> LOCATION: (128)..(128)
<223> OTHER INFORMATION: n = A,T,C or G

<400> SEQUENCE: 20
ctgttgttga actgaaataa ataacaaaaa aatcataaag ntggaggaaa gatgatcgan      60
tccccgcccc ttgacaatcg tccgataaaa accaactata ttcngtcctt tttacaaaca    120
attccaantg tctgaccgaa ccgcga                                          146

<210> SEQ ID NO 21
<211> LENGTH: 140
<212> TYPE: DNA
<213> ORGANISM: Ixodes ricinus
<220> FEATURE:
<221> NAME/KEY: misc_feature
<222> LOCATION: (3)..(3)
<223> OTHER INFORMATION: n = A,T,C or G
<220> FEATURE:
<221> NAME/KEY: misc_feature
<222> LOCATION: (10)..(10)
<223> OTHER INFORMATION: n = A,T,C or G
<220> FEATURE:
<221> NAME/KEY: misc_feature
<222> LOCATION: (30)..(30)
<223> OTHER INFORMATION: n = A,T,C or G

<400> SEQUENCE: 21
ctnggacgan gtcctatgac ttgcgcttan gtttcttagt cttcttcggt ttcttctttt      60
tttgcttcgg ttttcggtg ggcgcaggtg tatagtcatc agtgtcggtg ggcccatccg      120
aatgagttgt caaatgacat                                                 140

<210> SEQ ID NO 22
<211> LENGTH: 143
<212> TYPE: DNA
<213> ORGANISM: Ixodes ricinus

<400> SEQUENCE: 22
tgccgaaaaa taacgatgat ttgacgttga ctctgcagaa gagtaaggtt ttcaccgaca      60
gttttctgtt tagcacgacg aaggataacg agcctatcga ttactacgtg agagccgaag    120
atgccgaacg agacatatat cac                                             143

<210> SEQ ID NO 23
<211> LENGTH: 140
<212> TYPE: DNA
<213> ORGANISM: Ixodes ricinus
<220> FEATURE:
<221> NAME/KEY: misc_feature
<222> LOCATION: (112)..(112)
<223> OTHER INFORMATION: n = A,T,C or G
```

-continued

<400> SEQUENCE: 23

```
tgttgctaca gactcgacgt ttcgagcttg ctcgccattt maagacaacg cactcacaga      60
atatttaagt gcgttcgtga wagctgtggg cttacgattg caggcgcttc antcaccagc     120
tgtgatatta magttcctag                                                  140
```

<210> SEQ ID NO 24
<211> LENGTH: 144
<212> TYPE: DNA
<213> ORGANISM: Ixodes ricinus

<400> SEQUENCE: 24

```
tcacgatagt tgaaacgttg aaacttgaaa tactcccaca gtcgttggat gcttcagaac      60
tgctaagaac ttcacacttt gcaagaagtw ccaaaatgaa agccgcgatg accgatgatt     120
tagcttccat cttctatcac ttga                                             144
```

<210> SEQ ID NO 25
<211> LENGTH: 95
<212> TYPE: DNA
<213> ORGANISM: Ixodes ricinus

<400> SEQUENCE: 25

```
gaccaccccg tccgaacttg ctaaakcaag caatggagtg aggtgttcta tgcgggttga      60
ttacaccaat ggcgctgcgt ggtgcgtggt gattt                                  95
```

<210> SEQ ID NO 26
<211> LENGTH: 1414
<212> TYPE: DNA
<213> ORGANISM: Ixodes ricinus
<220> FEATURE:
<221> NAME/KEY: CDS
<222> LOCATION: (143)..(1276)

<400> SEQUENCE: 26

```
gtagggccgt gcaagcgaag gcagcgaagg ctgcgagtgt acgtgcagtt cggaagtgca      60
atatcctgtt attaagctct aattagcaca ctgtgagtcg atcagaggcc tctcttaacg     120
ccacattgaa aaaggatcca ag atg gag gca agt ctg agc aac cac atc ctt      172
                         Met Glu Ala Ser Leu Ser Asn His Ile Leu
                         1               5                   10 aac ttc tcc gtc gac cta tac aag cag ctg aaa ccc tcc ggc aaa gac      220
Asn Phe Ser Val Asp Leu Tyr Lys Gln Leu Lys Pro Ser Gly Lys Asp
                15                  20                  25 acg gca gga aac gtc ttc tgc tca cca ttc agt att gca gct gct ctg      268
Thr Ala Gly Asn Val Phe Cys Ser Pro Phe Ser Ile Ala Ala Ala Leu
            30                  35                  40 tcc atg gcc ctc gca gga gct aga ggc aac act gcc aag caa atc gct      316
Ser Met Ala Leu Ala Gly Ala Arg Gly Asn Thr Ala Lys Gln Ile Ala
        45                  50                  55 gcc atc ctg cac tca aac gac gac aag atc cac gac cac ttc tcc aac      364
Ala Ile Leu His Ser Asn Asp Asp Lys Ile His Asp His Phe Ser Asn
    60                  65                  70 ttc ctt tgc aag ctt ccc agt tac gcc cca gat gtg gcc ctg cac atc      412
Phe Leu Cys Lys Leu Pro Ser Tyr Ala Pro Asp Val Ala Leu His Ile
75                  80                  85                  90 gcc aat cgc atg tac tct gag cag acc ttc cat ccg aaa gcg gag tac      460
Ala Asn Arg Met Tyr Ser Glu Gln Thr Phe His Pro Lys Ala Glu Tyr
                95                  100                 105
```

| | | |
|---|---|---|
| aca acc ctg ttg caa aag tcc tac gac agc acc atc aag gct gtt gac<br>Thr Thr Leu Leu Gln Lys Ser Tyr Asp Ser Thr Ile Lys Ala Val Asp<br>110                        115                      120 | 508 |
| ttt gca gga aat gcc gac agg gtc cgt ctg gag gtc aat gcc tgg gtt<br>Phe Ala Gly Asn Ala Asp Arg Val Arg Leu Glu Val Asn Ala Trp Val<br>        125                      130                      135 | 556 |
| gag gaa gtc acc agg tca aag atc agg gac ctg ctc gca cct gga act<br>Glu Glu Val Thr Arg Ser Lys Ile Arg Asp Leu Leu Ala Pro Gly Thr<br>140                        145                      150 | 604 |
| gtt gat tca tcg aca tca ctt ata tta gtg aat gcc att tac ttc aaa<br>Val Asp Ser Ser Thr Ser Leu Ile Leu Val Asn Ala Ile Tyr Phe Lys<br>155                      160                      165                      170 | 652 |
| ggt ctg tgg gat tct cag ttc aag cct agt gct acg aag ccg gga gat<br>Gly Leu Trp Asp Ser Gln Phe Lys Pro Ser Ala Thr Lys Pro Gly Asp<br>                175                      180                      185 | 700 |
| ttt cac ttg aca cca cag acc tca aag aaa gtg gac atg atg cac cag<br>Phe His Leu Thr Pro Gln Thr Ser Lys Lys Val Asp Met Met His Gln<br>190                        195                      200 | 748 |
| gaa ggg gac ttc aag atg ggt cac tgc agc gac ctc aag gtc act gcg<br>Glu Gly Asp Phe Lys Met Gly His Cys Ser Asp Leu Lys Val Thr Ala<br>        205                      210                      215 | 796 |
| ctt gag ata ccc tac aaa ggc aac aag acg tcg atg gtc att ctc ctg<br>Leu Glu Ile Pro Tyr Lys Gly Asn Lys Thr Ser Met Val Ile Leu Leu<br>220                        225                      230 | 844 |
| ccc gaa gat gta gag gga ctc tca gtc ctg gag gaa cac ttg acc gct<br>Pro Glu Asp Val Glu Gly Leu Ser Val Leu Glu Glu His Leu Thr Ala<br>235                        240                      245                      250 | 892 |
| ccg aaa ctg tcg gct ctg ctc ggc ggc atg tat gcg acg tcc gat gtc<br>Pro Lys Leu Ser Ala Leu Leu Gly Gly Met Tyr Ala Thr Ser Asp Val<br>                255                      260                      265 | 940 |
| aac ttg cgc ttg ccg aag ttc aaa cta gag cag tcc ata ggt ttg aag<br>Asn Leu Arg Leu Pro Lys Phe Lys Leu Glu Gln Ser Ile Gly Leu Lys<br>                270                      275                      280 | 988 |
| gat gta ctg atg gcg atg gga gtc aag gat ttc ttc acg tcc ctt gca<br>Asp Val Leu Met Ala Met Gly Val Lys Asp Phe Phe Thr Ser Leu Ala<br>285                        290                      295 | 1036 |
| gat ctt tct ggc atc agc gct gcg ggg aat ctg tgc gct tcg gat gtc<br>Asp Leu Ser Gly Ile Ser Ala Ala Gly Asn Leu Cys Ala Ser Asp Val<br>        300                      305                      310 | 1084 |
| atc cac aag gct ttt gtg gaa gtt aat gag gag ggc aca gag gct gca<br>Ile His Lys Ala Phe Val Glu Val Asn Glu Glu Gly Thr Glu Ala Ala<br>315                        320                      325                      330 | 1132 |
| gct gcc act gcc ata ccc att atg ttg atg tgt gcg aga ttt cca cag<br>Ala Ala Thr Ala Ile Pro Ile Met Leu Met Cys Ala Arg Phe Pro Gln<br>                335                      340                      345 | 1180 |
| gtg gtg aac ttt ttc gtt gac cgc cca ttc atg ttc ttg atc cac agc<br>Val Val Asn Phe Phe Val Asp Arg Pro Phe Met Phe Leu Ile His Ser<br>350                        355                      360 | 1228 |
| cat gat cca gat gtt gtt ctc ttc atg gga tcc atc cgt gag ctc taa<br>His Asp Pro Asp Val Val Leu Phe Met Gly Ser Ile Arg Glu Leu<br>        365                      370                      375 | 1276 |
| aaagcatatt cttaacggcg gccaatcagt ctgtggagtt atctcttagt cactaatgtg | 1336 |
| taacaattct gcaatattca gcttgtgtat ttcagtaact tgctagatct ttgtgttgtt | 1396 |
| gatgttaggc ttcttgcg | 1414 |

<210> SEQ ID NO 27
<211> LENGTH: 377
<212> TYPE: PRT
<213> ORGANISM: Ixodes ricinus

<400> SEQUENCE: 27

```
Met Glu Ala Ser Leu Ser Asn His Ile Leu Asn Phe Ser Val Asp Leu
1               5                   10                  15

Tyr Lys Gln Leu Lys Pro Ser Gly Lys Asp Thr Ala Gly Asn Val Phe
            20                  25                  30

Cys Ser Pro Phe Ser Ile Ala Ala Leu Ser Met Ala Leu Ala Gly
        35                  40                  45

Ala Arg Gly Asn Thr Ala Lys Gln Ile Ala Ala Ile Leu His Ser Asn
    50                  55                  60

Asp Asp Lys Ile His Asp His Phe Ser Asn Phe Leu Cys Lys Leu Pro
65                  70                  75                  80

Ser Tyr Ala Pro Asp Val Ala Leu His Ile Ala Asn Arg Met Tyr Ser
                85                  90                  95

Glu Gln Thr Phe His Pro Lys Ala Glu Tyr Thr Thr Leu Leu Gln Lys
            100                 105                 110

Ser Tyr Asp Ser Thr Ile Lys Ala Val Asp Phe Ala Gly Asn Ala Asp
        115                 120                 125

Arg Val Arg Leu Glu Val Asn Ala Trp Val Glu Val Thr Arg Ser
130                 135                 140

Lys Ile Arg Asp Leu Leu Ala Pro Gly Thr Val Asp Ser Ser Thr Ser
145                 150                 155                 160

Leu Ile Leu Val Asn Ala Ile Tyr Phe Lys Gly Leu Trp Asp Ser Gln
                165                 170                 175

Phe Lys Pro Ser Ala Thr Lys Pro Gly Asp Phe His Leu Thr Pro Gln
            180                 185                 190

Thr Ser Lys Lys Val Asp Met Met His Gln Glu Gly Asp Phe Lys Met
        195                 200                 205

Gly His Cys Ser Asp Leu Lys Val Thr Ala Leu Glu Ile Pro Tyr Lys
    210                 215                 220

Gly Asn Lys Thr Ser Met Val Ile Leu Leu Pro Glu Asp Val Glu Gly
225                 230                 235                 240

Leu Ser Val Leu Glu Glu His Leu Thr Ala Pro Lys Leu Ser Ala Leu
                245                 250                 255

Leu Gly Gly Met Tyr Ala Thr Ser Asp Val Asn Leu Arg Leu Pro Lys
            260                 265                 270

Phe Lys Leu Glu Gln Ser Ile Gly Leu Lys Asp Val Leu Met Ala Met
        275                 280                 285

Gly Val Lys Asp Phe Phe Thr Ser Leu Ala Asp Leu Ser Gly Ile Ser
    290                 295                 300

Ala Ala Gly Asn Leu Cys Ala Ser Asp Val Ile His Lys Ala Phe Val
305                 310                 315                 320

Glu Val Asn Glu Glu Gly Thr Glu Ala Ala Ala Thr Ala Ile Pro
                325                 330                 335

Ile Met Leu Met Cys Ala Arg Phe Pro Gln Val Val Asn Phe Phe Val
            340                 345                 350

Asp Arg Pro Phe Met Phe Leu Ile His Ser His Asp Pro Asp Val Val
        355                 360                 365

Leu Phe Met Gly Ser Ile Arg Glu Leu
    370                 375
```

<210> SEQ ID NO 28
<211> LENGTH: 200
<212> TYPE: DNA
<213> ORGANISM: Ixodes ricinus

<400> SEQUENCE: 28

```
accgtaacca aaattgtttc tttccagaag aatggttcaa acttttcaaa cagatttcgg        60
aaactcttct tgcactttta aaatccaatc tacaatcttt cctcgcactt ctgaattgca       120
ttccagttta ccttccaagc aaacctcttt tggcaactcc agccgtactc catttcggca       180
taccacagtg catgcacttg                                                   200
```

<210> SEQ ID NO 29
<211> LENGTH: 241
<212> TYPE: DNA
<213> ORGANISM: Ixodes ricinus

<400> SEQUENCE: 29

```
cgtattcttt gaagatttgt atacgaaaca taaattcgtc atgcatactt tgatggtta        60
cacgacatgc gaagctgccg acaaagaaga ctgggaagat aagaagcacc tagttacggt       120
agtgcgtgga ccggataaac gaaagtacac gtttctacgc aacattctca ccttacaacg       180
gagagtgaga gttagcaaaa caatgattga gctcgtacgg aacatgtcct gtaggacatt       240
t                                                                       241
```

<210> SEQ ID NO 30
<211> LENGTH: 313
<212> TYPE: DNA
<213> ORGANISM: Ixodes ricinus
<220> FEATURE:
<221> NAME/KEY: misc_feature
<222> LOCATION: (6)..(6)
<223> OTHER INFORMATION: n = A,T,C or G

<400> SEQUENCE: 30

```
aagcanccgg actacctgct tgaaaacgtt gtacgggcaa acttggacgg aaaactccca        60
gatgctactc cagttcctcc cggaagctac acgtacgctg agaatgataa cttcacctgc       120
tattccagaa gtacaccgtt tccggatggg gtgaatgttg tataacggct gctgggtgcg       180
gaagactatg atggattacg caaaaaagtt ctaaacgagt tgtttcccat cccggaaagt       240
ctgctgtatg ctgacatgat gcgacttgtg gctaagaaag acagagttga tcacactagt       300
ggatgacctg gga                                                          313
```

<210> SEQ ID NO 31
<211> LENGTH: 2417
<212> TYPE: DNA
<213> ORGANISM: Ixodes ricinus
<220> FEATURE:
<221> NAME/KEY: CDS
<222> LOCATION: (218)..(1495)

<400> SEQUENCE: 31
gtcgtagtcg tagtcgtagt cagttgcgca tgcgcggggc tttcctgtct ttcttgcctt 60
tctgcagtcg ttcaccaaca tgtggataca gctccggaga tttgtaaaca aatactgcac 120
ttttaagcaa gacttgatat ttagatcgat atcctcctgt tgtccgtctt gattaatcgg 180
ctctttaggg tttttagaat aggcttttcg gtacgag atg ccc aaa gga aag agg 235
Met Pro Lys Gly Lys Arg
1 5 gga ccc aaa gca ggt ggc gcc gcg cgc ggt ggc cgg tgc gag gcc agc 283
Gly Pro Lys Ala Gly Gly Ala Ala Arg Gly Gly Arg Cys Glu Ala Ser
10 15 20

```
ctg gct ccg tcg tcc agc gac gag gag tcc aac gca gac acg gcg agc       331
Leu Ala Pro Ser Ser Ser Asp Glu Glu Ser Asn Ala Asp Thr Ala Ser
        25                  30                  35 gtg ctg agc tgc gcc tcg gag tct cgc tgt ggc agt gac ggc acc gtt       379
Val Leu Ser Cys Ala Ser Glu Ser Arg Cys Gly Ser Asp Gly Thr Val
    40                  45                  50 gga gac cca gaa gcg gag gag gct gtg ctg cat gac gac ttt gaa gac       427
Gly Asp Pro Glu Ala Glu Glu Ala Val Leu His Asp Asp Phe Glu Asp
55                  60                  65                  70 aaa ctc aag gag gcc atc gac gga gct tcg cag aag agt gcc aaa gga       475
Lys Leu Lys Glu Ala Ile Asp Gly Ala Ser Gln Lys Ser Ala Lys Gly
                75                  80                  85 cgg ctg tcg tgc ctg gag gcg att cgc aag gcc ttt tcc acc aaa tac       523
Arg Leu Ser Cys Leu Glu Ala Ile Arg Lys Ala Phe Ser Thr Lys Tyr
        90                  95                  100 ctg tac gac ttc ctc atg gac aga ccg agc acg gtg tgc gac ctg gtg       571
Leu Tyr Asp Phe Leu Met Asp Arg Pro Ser Thr Val Cys Asp Leu Val
    105                 110                 115 gag cgt ggg gtg cgc aag ggc cga ggg gag gag gcg gcc ctg tgc gcc       619
Glu Arg Gly Val Arg Lys Gly Arg Gly Glu Glu Ala Ala Leu Cys Ala
120                 125                 130 act ctc ggg gcc ctg gcc tgc gtc cag ctc ggg gtc ggg gcc gag gcg       667
Thr Leu Gly Ala Leu Ala Cys Val Gln Leu Gly Val Gly Ala Glu Ala
135                 140                 145                 150 gac gcc ctg ttc gac gcc ctg cgc cag ccg ctc tgc act ttg ctg ctt       715
Asp Ala Leu Phe Asp Ala Leu Arg Gln Pro Leu Cys Thr Leu Leu Leu
                155                 160                 165 gac ggg gcc cag ggg ccc tcc ccc agg gcc agg tgt gcc act gcc ctc       763
Asp Gly Ala Gln Gly Pro Ser Pro Arg Ala Arg Cys Ala Thr Ala Leu
        170                 175                 180 ggc ctc tgc tgc ttc gtg gtg gac tcg gac aac cag ctg gtg ctg cag       811
Gly Leu Cys Cys Phe Val Val Asp Ser Asp Asn Gln Leu Val Leu Gln
    185                 190                 195 ccg tgc atg gag gtg ctc tgg cag gtg gtg ggt gcc aag gcg ggc ccc       859
Pro Cys Met Glu Val Leu Trp Gln Val Val Gly Ala Lys Ala Gly Pro
200                 205                 210 ggc tct ccg gtg ctc cag gca gcg gcc ctg ctc gcc tgg ggc ctc ctg       907
Gly Ser Pro Val Leu Gln Ala Ala Ala Leu Leu Ala Trp Gly Leu Leu
215                 220                 225                 230 ctc agc gtg gct ccc gtc gac cgc ctg ctg gcg ctc acg cgc acg cac       955
Leu Ser Val Ala Pro Val Asp Arg Leu Leu Ala Leu Thr Arg Thr His
                235                 240                 245 ctg ccc cgg ctg cag gag ctg ctg gag agc ccc gac ctg gac ctg cgc      1003
Leu Pro Arg Leu Gln Glu Leu Leu Glu Ser Pro Asp Leu Asp Leu Arg
        250                 255                 260 att gcc gcc ggg gag gtg atc gcc gtc atg tac gag ggg gcc agg gac      1051
Ile Ala Ala Gly Glu Val Ile Ala Val Met Tyr Glu Gly Ala Arg Asp
    265                 270                 275 tac gac gag gac ttt gag gag ccc tcg gag tcc ctg tgt gcc cag ctg      1099
Tyr Asp Glu Asp Phe Glu Glu Pro Ser Glu Ser Leu Cys Ala Gln Leu
280                 285                 290 cgc cag ctg gcc acg gac agc cag aag ttt cgg gcc aag aag gag cgg      1147
Arg Gln Leu Ala Thr Asp Ser Gln Lys Phe Arg Ala Lys Lys Glu Arg
295                 300                 305                 310 cgc cag cag cgc tcc acc ttc agg gac gtc tac cgg gcc gtc agg gag      1195
Arg Gln Gln Arg Ser Thr Phe Arg Asp Val Tyr Arg Ala Val Arg Glu
                315                 320                 325 ggg gcc tct ccc gac gtg agc gtc aag ttt ggc cgg gaa gtc ctg gaa      1243
Gly Ala Ser Pro Asp Val Ser Val Lys Phe Gly Arg Glu Val Leu Glu
        330                 335                 340
```

```
ctg gac acc tgg agt cgc aag ctg cag tac gac gct ttc tgc cag ctg     1291
Leu Asp Thr Trp Ser Arg Lys Leu Gln Tyr Asp Ala Phe Cys Gln Leu
        345                 350                 355
ctg ggc tcc ggc atg aac ctg cac ctg gcc gtg aac gag ctg ctg agg     1339
Leu Gly Ser Gly Met Asn Leu His Leu Ala Val Asn Glu Leu Leu Arg
    360                 365                 370
gac atc ttt gaa ctg ggg cag gtg ctg gca acc gag gac cac att atc     1387
Asp Ile Phe Glu Leu Gly Gln Val Leu Ala Thr Glu Asp His Ile Ile
375                 380                 385                 390
tcc aag atc acc aag ttc gaa agg cac atg gtg aac atg gcc agc tgc     1435
Ser Lys Ile Thr Lys Phe Glu Arg His Met Val Asn Met Ala Ser Cys
                395                 400                 405
cgg gcc cgc acc aag aca cgc aac cgg ctg agg gac aag cgc gcc gac     1483
Arg Ala Arg Thr Lys Thr Arg Asn Arg Leu Arg Asp Lys Arg Ala Asp
            410                 415                 420
gtg gtc gcc tga acctgcggag ggatgcttag ctatgcactc gccggcctac         1535
Val Val Ala
        425
cctggcggga ctcgatgcca ctcacgagtc ggcgctcgca aattcgccgc ccatcgttac   1595
gcaatgggag acaaagctgc ttttggcatt accgtttgag gtcggctcca acccatagat   1655
gaatttcttt tttgtggccg tttctgggtt acatgttttg ggggaaggga gtggaactgt   1715
ccggttcttt ggcacacgtc aggttgctct tgatgcgcga cgtgcttgta tttgggtact   1775
gccgacacca agcgtttcgg cgattcctgg aaaagagtgc ctctcgctcg acgtttggtt   1835
gttttctgcg tggtccgtcg tcgaccttcg ttcgtccaaa gacgccgtcc ggtttcatac   1895
tcccccccgc acacatatcg aggccaatta aattgctaag ggtgccgttg tcgtgcatct   1955
ggcaggctca gaagtggctt atttgtcttt taattttgcc gatgcacgca aaaattgtca   2015
tttcttgaaa gtttctcttt tattgcgtac acaattcaac ttttatgtaa tttctgatgg   2075
tctgttttac gtgtgcgtgt gtaaaacgta actttggaag aatttttatg cacactgaac   2135
aaacgctcgg tcctggggtt gaaagtgctc ggtgtgtgca tgagctaaag tgcaactgct   2195
ttgttccgaa ggttttctag tcgccgaaat gtaccattgt ggaccttgtt gcgagagacc   2255
ttggtcttct gggggagctg ctgtagcgtg gcaagccact attttgggag cgacattgca   2315
gagaaaatcg gcttttagaa aggcacctgc gcggcgagtg gacgtttttt cgtatatact   2375
gcgaaaaaaa aaaaaaaaaa aaaaaaaaaa aaaaaaaaaa aa                      2417

<210> SEQ ID NO 32
<211> LENGTH: 425
<212> TYPE: PRT
<213> ORGANISM: Ixodes ricinus

<400> SEQUENCE: 32

Met Pro Lys Gly Lys Arg Gly Pro Lys Ala Gly Gly Ala Ala Arg Gly
1               5                   10                  15

Gly Arg Cys Glu Ala Ser Leu Ala Pro Ser Ser Ser Asp Glu Glu Ser
            20                  25                  30

Asn Ala Asp Thr Ala Ser Val Leu Ser Cys Ala Ser Glu Ser Arg Cys
        35                  40                  45

Gly Ser Asp Gly Thr Val Gly Asp Pro Glu Ala Glu Glu Ala Val Leu
    50                  55                  60

His Asp Asp Phe Glu Asp Lys Leu Lys Glu Ala Ile Asp Gly Ala Ser
65                  70                  75                  80

Gln Lys Ser Ala Lys Gly Arg Leu Ser Cys Leu Glu Ala Ile Arg Lys
                85                  90                  95
```

```
Ala Phe Ser Thr Lys Tyr Leu Tyr Asp Phe Leu Met Asp Arg Pro Ser
            100                 105                 110

Thr Val Cys Asp Leu Val Glu Arg Gly Val Arg Lys Gly Arg Gly Glu
        115                 120                 125

Glu Ala Ala Leu Cys Ala Thr Leu Gly Ala Leu Ala Cys Val Gln Leu
    130                 135                 140

Gly Val Gly Ala Glu Ala Asp Ala Leu Phe Asp Ala Leu Arg Gln Pro
145                 150                 155                 160

Leu Cys Thr Leu Leu Leu Asp Gly Ala Gln Gly Pro Ser Pro Arg Ala
                165                 170                 175

Arg Cys Ala Thr Ala Leu Gly Leu Cys Cys Phe Val Val Asp Ser Asp
            180                 185                 190

Asn Gln Leu Val Leu Gln Pro Cys Met Glu Val Leu Trp Gln Val Val
        195                 200                 205

Gly Ala Lys Ala Gly Pro Gly Ser Pro Val Leu Gln Ala Ala Ala Leu
210                 215                 220

Leu Ala Trp Gly Leu Leu Leu Ser Val Ala Pro Val Asp Arg Leu Leu
225                 230                 235                 240

Ala Leu Thr Arg Thr His Leu Pro Arg Leu Gln Glu Leu Leu Glu Ser
                245                 250                 255

Pro Asp Leu Asp Leu Arg Ile Ala Ala Gly Glu Val Ile Ala Val Met
            260                 265                 270

Tyr Glu Gly Ala Arg Asp Tyr Asp Glu Asp Phe Glu Glu Pro Ser Glu
        275                 280                 285

Ser Leu Cys Ala Gln Leu Arg Gln Leu Ala Thr Asp Ser Gln Lys Phe
    290                 295                 300

Arg Ala Lys Lys Glu Arg Gln Gln Arg Ser Thr Phe Arg Asp Val
305                 310                 315                 320

Tyr Arg Ala Val Arg Glu Gly Ala Ser Pro Asp Val Ser Val Lys Phe
                325                 330                 335

Gly Arg Glu Val Leu Glu Leu Asp Thr Trp Ser Arg Lys Leu Gln Tyr
            340                 345                 350

Asp Ala Phe Cys Gln Leu Leu Gly Ser Gly Met Asn Leu His Leu Ala
        355                 360                 365

Val Asn Glu Leu Leu Arg Asp Ile Phe Glu Leu Gly Gln Val Leu Ala
    370                 375                 380

Thr Glu Asp His Ile Ile Ser Lys Ile Thr Lys Phe Glu Arg His Met
385                 390                 395                 400

Val Asn Met Ala Ser Cys Arg Ala Arg Thr Lys Thr Arg Asn Arg Leu
                405                 410                 415

Arg Asp Lys Arg Ala Asp Val Val Ala
            420                 425

<210> SEQ ID NO 33
<211> LENGTH: 933
<212> TYPE: DNA
<213> ORGANISM: Ixodes ricinus
<220> FEATURE:
<221> NAME/KEY: CDS
<222> LOCATION: (32)..(853)

<400> SEQUENCE: 33
gattgggaac ctcctattcc tcacttgaaa c atg gct gga ctc cgc tcc tgc        52
                                   Met Ala Gly Leu Arg Ser Cys
                                    1               5
```

| | | |
|---|---|---|
| atc ctc ctg gct ctt gcc act agt gcc ttc gcc ggc tac ctt cac ggt<br>Ile Leu Leu Ala Leu Ala Thr Ser Ala Phe Ala Gly Tyr Leu His Gly<br>10                           15                         20 | | 100 |
| ggc ctt acc cac ggc gct ggg tac ggt tac ggt gtc ggc tac ggt tcc<br>Gly Leu Thr His Gly Ala Gly Tyr Gly Tyr Gly Val Gly Tyr Gly Ser<br>    25                        30                         35 | | 148 |
| ggc ctt ggc tat ggc ctt ggc tac ggt tcc ggc ctt ggc tat gga cat<br>Gly Leu Gly Tyr Gly Leu Gly Tyr Gly Ser Gly Leu Gly Tyr Gly His<br>40                           45                         50                       55 | | 196 |
| gct gtt ggc ctt gga cac ggc ttt ggc tat tct ggt ctg acc ggc tac<br>Ala Val Gly Leu Gly His Gly Phe Gly Tyr Ser Gly Leu Thr Gly Tyr<br>                  60                        65                         70 | | 244 |
| agt gtg gct gcc cca gct agc tac gcc gtt gct gct cca gcc gtc agc<br>Ser Val Ala Ala Pro Ala Ser Tyr Ala Val Ala Ala Pro Ala Val Ser<br>    75                        80                         85 | | 292 |
| cgc acc gtt tcc act tac cac gct gct cca gct gtg gcc acc tac gcc<br>Arg Thr Val Ser Thr Tyr His Ala Ala Pro Ala Val Ala Thr Tyr Ala<br>90                         95                       100 | | 340 |
| gct gct cct gtc gcc acc tat gct gtt gct cca gct gtc act agg gtt<br>Ala Ala Pro Val Ala Thr Tyr Ala Val Ala Pro Ala Val Thr Arg Val<br>105                         110                        115 | | 388 |
| tcc ccc gtt cgc gcc gcc cca gct gtg gcc acg tac gcc gcc gct cca<br>Ser Pro Val Arg Ala Ala Pro Ala Val Ala Thr Tyr Ala Ala Ala Pro<br>120                       125                         130                       135 | | 436 |
| gtc gcc acc tac gcc gct gct cca gct gtg acc agg gtg tcc acc att<br>Val Ala Thr Tyr Ala Ala Ala Pro Ala Val Thr Arg Val Ser Thr Ile<br>                  140                         145                       150 | | 484 |
| cac gct gcc ccg gct gtg gcc aat tac gcc gtc gct cca gtc gcc acc<br>His Ala Ala Pro Ala Val Ala Asn Tyr Ala Val Ala Pro Val Ala Thr<br>                155                         160                       165 | | 532 |
| tat gcc gct gct cca gct gtg acc agg gtg tcc acc atc cac gcc gct<br>Tyr Ala Ala Ala Pro Ala Val Thr Arg Val Ser Thr Ile His Ala Ala<br>            170                         175                       180 | | 580 |
| cca gcc gtg gct agc tac cag acc tac cac gct cca gct gtc gcc act<br>Pro Ala Val Ala Ser Tyr Gln Thr Tyr His Ala Pro Ala Val Ala Thr<br>185                       190                                 195 | | 628 |
| gtg gct cat gct cca gct gtg gcc agc tac cag acc tac cac gct gcc<br>Val Ala His Ala Pro Ala Val Ala Ser Tyr Gln Thr Tyr His Ala Ala<br>200                       205                         210                       215 | | 676 |
| cca gcc gtg gct acc tac gcc cat gcc gct ccc gtc tac ggc tat ggt<br>Pro Ala Val Ala Thr Tyr Ala His Ala Ala Pro Val Tyr Gly Tyr Gly<br>                  220                         225                       230 | | 724 |
| gtc ggt acc ctc gga tat ggt gtc ggc cac tac ggc tac gga cac ggt<br>Val Gly Thr Leu Gly Tyr Gly Val Gly His Tyr Gly Tyr Gly His Gly<br>                     235                         240                       245 | | 772 |
| ctt ggc agc tac ggc ctg aac tac ggt tac ggc ctc ggc acc tac ggt<br>Leu Gly Ser Tyr Gly Leu Asn Tyr Gly Tyr Gly Leu Gly Thr Tyr Gly<br>            250                         255                       260 | | 820 |
| gac tac acc acc ctt ctc cgc aag aag aag taa atggcacatc tcaagagagc<br>Asp Tyr Thr Thr Leu Leu Arg Lys Lys Lys<br>265                         270 | | 873 |
| ccattggact gccatcgaca ttcttcttca ataaagagc ccgaagatgg cattattttt | | 933 |

<210> SEQ ID NO 34
<211> LENGTH: 273
<212> TYPE: PRT
<213> ORGANISM: Ixodes ricinus

<400> SEQUENCE: 34

Met Ala Gly Leu Arg Ser Cys Ile Leu Leu Ala Leu Ala Thr Ser Ala
1               5                   10                  15

Phe Ala Gly Tyr Leu His Gly Gly Leu Thr His Gly Ala Gly Tyr Gly
            20                  25                  30

Tyr Gly Val Gly Tyr Gly Ser Gly Leu Gly Tyr Gly Leu Gly Tyr Gly
        35                  40                  45

Ser Gly Leu Gly Tyr Gly His Ala Val Gly Leu Gly His Gly Phe Gly
    50                  55                  60

Tyr Ser Gly Leu Thr Gly Tyr Ser Val Ala Ala Pro Ala Ser Tyr Ala
65                  70                  75                  80

Val Ala Ala Pro Ala Val Ser Arg Thr Val Ser Thr Tyr His Ala Ala
                85                  90                  95

Pro Ala Val Ala Thr Tyr Ala Ala Ala Pro Val Ala Thr Tyr Ala Val
            100                 105                 110

Ala Pro Ala Val Thr Arg Val Ser Pro Val Arg Ala Ala Pro Ala Val
        115                 120                 125

Ala Thr Tyr Ala Ala Ala Pro Val Ala Thr Tyr Ala Ala Ala Pro Ala
    130                 135                 140

Val Thr Arg Val Ser Thr Ile His Ala Ala Pro Ala Val Ala Asn Tyr
145                 150                 155                 160

Ala Val Ala Pro Val Ala Thr Tyr Ala Ala Ala Pro Ala Val Thr Arg
                165                 170                 175

Val Ser Thr Ile His Ala Ala Pro Ala Val Ala Ser Tyr Gln Thr Tyr
            180                 185                 190

His Ala Pro Ala Val Ala Thr Val Ala His Ala Pro Ala Val Ala Ser
        195                 200                 205

Tyr Gln Thr Tyr His Ala Ala Pro Ala Val Ala Thr Tyr Ala His Ala
    210                 215                 220

Ala Pro Val Tyr Gly Tyr Gly Val Gly Thr Leu Gly Tyr Gly Val Gly
225                 230                 235                 240

His Tyr Gly Tyr Gly His Gly Leu Gly Ser Tyr Gly Leu Asn Tyr Gly
                245                 250                 255

Tyr Gly Leu Gly Thr Tyr Gly Asp Tyr Thr Thr Leu Leu Arg Lys Lys
            260                 265                 270

Lys

<210> SEQ ID NO 35
<211> LENGTH: 90
<212> TYPE: PRT
<213> ORGANISM: Ixodes ricinus

<400> SEQUENCE: 35

Met Lys Leu Thr Met Gln Leu Ile Phe Val Val Ser Leu Val Ile Val
1               5                   10                  15

Ala Cys Ile Val Val Asp Thr Ala Asn His Lys Gly Arg Gly Arg Pro
            20                  25                  30

Ala Lys Cys Lys Leu Pro Pro Asp Asp Gly Pro Cys Arg Ala Arg Ile
        35                  40                  45

Pro Ser Tyr Tyr Phe Asp Arg Lys Thr Lys Thr Cys Lys Glu Phe Met
    50                  55                  60

```
Tyr Gly Gly Cys Glu Gly Asn Glu Asn Asn Phe Glu Asn Ile Thr Thr
 65                  70                  75                  80

Cys Gln Glu Glu Cys Arg Ala Lys Lys Val
                 85                  90

<210> SEQ ID NO 36
<211> LENGTH: 67
<212> TYPE: PRT
<213> ORGANISM: Ixodes ricinus

<400> SEQUENCE: 36

Ala Asn His Lys Gly Arg Gly Arg Pro Ala Lys Cys Lys Leu Pro Pro
  1               5                  10                  15

Asp Asp Gly Pro Cys Arg Ala Arg Ile Pro Ser Tyr Tyr Phe Asp Arg
                 20                  25                  30

Lys Thr Lys Thr Cys Lys Glu Phe Met Tyr Gly Gly Cys Glu Gly Asn
             35                  40                  45

Glu Asn Asn Phe Glu Asn Ile Thr Thr Cys Gln Glu Glu Cys Arg Ala
         50                  55                  60

Lys Lys Val
 65

<210> SEQ ID NO 37
<211> LENGTH: 65
<212> TYPE: PRT
<213> ORGANISM: Bungarus fasciatus

<400> SEQUENCE: 37

Lys Asn Arg Pro Thr Phe Cys Asn Leu Leu Pro Glu Thr Gly Arg Cys
  1               5                  10                  15

Asn Ala Leu Ile Pro Ala Phe Tyr Tyr Asn Ser His Leu His Lys Cys
                 20                  25                  30

Gln Lys Phe Asn Tyr Gly Gly Cys Gly Gly Asn Ala Asn Asn Phe Lys
             35                  40                  45

Thr Ile Asp Glu Cys Gln Arg Thr Cys Ala Ala Lys Tyr Gly Arg Ser
         50                  55                  60

Ser
 65

<210> SEQ ID NO 38
<211> LENGTH: 33
<212> TYPE: DNA
<213> ORGANISM: Artificial Sequence
<220> FEATURE:
<223> OTHER INFORMATION: synthetic primer

<400> SEQUENCE: 38
cgcggatccg cggccaacca caaaggtaga ggg                                    33

<210> SEQ ID NO 39
<211> LENGTH: 37
<212> TYPE: DNA
<213> ORGANISM: Artificial Sequence
<220> FEATURE:
<223> OTHER INFORMATION: synthetic primer

<400> SEQUENCE: 39
ccgctcgagc ggttagactt tttttgctct gcattcc                                37
```

```
<210> SEQ ID NO 40
<211> LENGTH: 19
<212> TYPE: RNA
<213> ORGANISM: Artificial Sequence
<220> FEATURE:
<223> OTHER INFORMATION: synthetic siRNA

<400> SEQUENCE: 40
ccaugcagag cacgaauuc                                                19

<210> SEQ ID NO 41
<211> LENGTH: 19
<212> TYPE: RNA
<213> ORGANISM: Artificial Sequence
<220> FEATURE:
<223> OTHER INFORMATION: synthetic siRNA

<400> SEQUENCE: 41
gcacgaauuc cgaguuacu                                                19

<210> SEQ ID NO 42
<211> LENGTH: 19
<212> TYPE: RNA
<213> ORGANISM: Artificial Sequence
<220> FEATURE:
<223> OTHER INFORMATION: synthetic siRNA

<400> SEQUENCE: 42
acuacgugcc aagaggaau                                                19

<210> SEQ ID NO 43
<211> LENGTH: 24
<212> TYPE: DNA
<213> ORGANISM: Artificial Sequence
<220> FEATURE:
<223> OTHER INFORMATION: synthetic primer

<400> SEQUENCE: 43
atgaaactaa cgatgcagct gatc                                          24

<210> SEQ ID NO 44
<211> LENGTH: 25
<212> TYPE: DNA
<213> ORGANISM: Artificial Sequence
<220> FEATURE:
<223> OTHER INFORMATION: synthetic primer

<400> SEQUENCE: 44
ttagactttt tttgctctgc attcc                                         25

<210> SEQ ID NO 45
<211> LENGTH: 21
<212> TYPE: DNA
<213> ORGANISM: Artificial Sequence
<220> FEATURE:
<223> OTHER INFORMATION: synthetic primer

<400> SEQUENCE: 45
atgtgtgacg acgaggttgc c                                             21

<210> SEQ ID NO 46
<211> LENGTH: 22
<212> TYPE: DNA
<213> ORGANISM: Artificial Sequence
```

```
<220> FEATURE:
<223> OTHER INFORMATION: synthetic primer

<400> SEQUENCE: 46
ttagaagcac ttgcggtgga tg                                              22
```

IDENTIFICATION AND MOLECULAR CHARACTERISATION OF PROTEINS, EXPRESSED IN THE *IXODES RICINUS* SALIVARY GLANDS

This application is a Divisional of U.S. Ser. No. 13/632,763, filed 1 Oct. 2012, which is a Continuation of U.S. Ser. No. 11/932,985, filed 31 Oct. 2007 and which applications are incorporated herein by reference. To the extent appropriate, a claim of priority is made to each of the above disclosed applications.

FIELD OF THE INVENTION

The present invention is related to the molecular characterisation of DNA sequences, which encode proteins expressed in the salivary glands of the *Ixodes ricinus* arthropod tick. These proteins are involved in the complex mechanism of interaction between this arthropod and its mammalian host. The invention relates to newly identified polynucleotides, polypeptides encoded by them and the use of such polynucleotides and polypeptides, and to their production.

BACKGROUND OF THE INVENTION

Ticks are hematophagous arthropods that feed on a wide diversity of hosts. Unlike this group of arthropods, the Ixodid adult female ticks have the characteristics to ingest blood for an extended period of over 2 weeks.

Completion of the blood meal is dependent on the relationships of ticks with hosts species. Resistance to tick infestation implicates both innate and acquired immunity, and is characterized by reduced feeding, molting and mating capabilities that may lead to the death of the parasite. Acquired immunity of resistant hosts is mediated by a polarized Th1-type immune response, involving IFN-γ production and delayed type hypersensitivity reaction.

Some hosts are unable to counteract the tick infestation. Indeed, during their blood meal, ticks circumvent host defences via pharmacologically active components secreted in their saliva. These factors can modulate both the innate and the acquired immunity of the host. In this way, the leukocyte responsiveness is modified during tick feeding. For example, cytokines production is modulated, inducing a polarised Th2 immune response.

Therefore, the complex tick-host molecular interaction can be considered as a balance between host defences raised against the parasite and the tick evasion strategies, facilitating feeding for an extended period. Although, there is extensive information about the effects of tick bioactive factors on host immune defences, little is known about the mechanisms of their actions. However, it has been observed that a wide range of new proteins is expressed during the blood meal. Several of them might be essential for the completion of the tick feeding process.

SUMMARY OF THE INVENTION

The present invention is related to a new isolated and purified polynucleotide obtained from tick salivary gland and presenting more than 75% identity with at least one nucleotide sequence selected from the group consisting of SEQ.ID.NO.1, SEQ.ID.NO.2, SEQ.ID.NO.3, SEQ.ID.NO.4, SEQ.ID.NO.5, SEQ.ID.NO.6, SEQ.ID.NO.7, SEQ.ID.NO.9, SEQ.ID.NO.10, SEQ.ID.NO.11, SEQ.ID.NO.12, SEQ.ID.NO.13, SEQ.ID.NO.14, SEQ.ID.NO.15, SEQ.ID.NO.16, SEQ.ID.NO.17, SEQ.ID.NO.19, SEQ.ID.NO.20, SEQ.ID.NO.21, SEQ.ID.NO.22, SEQ.ID.NO.23, SEQ.ID.NO.24, SEQ.ID.NO.25, SEQ.ID.NO.26, SEQ.ID.NO.28, SEQ.ID.NO.29, SEQ.ID.NO.30, SEQ.ID.NO.31, SEQ.ID.NO.33 or a sequence complementary thereto, or a fragment thereof, as defined hereafter.

Preferably, the polynucleotide of claim 1, which presents at least 80% identity with at least one of said nucleotide sequences, more preferably at least 90% identity, more preferably with at least 95% identity, and even at least about 98 to 99% identity.

Preferably, the polynucleotide of claim 1, which presents at least 99% identity with at least one of said nucleotide sequences.

The present invention is also related to a polypeptide encoded by the polynucleotide of the present invention or a biologically active fragment or portion thereof.

Said polypeptide may be modified by or linked to at least one substitution group, preferably selected from the group consisting of amide, acetyl, phosphoryl, and/or glycosyl groups.

Moreover, said polypeptide may take the form of a "mature" protein.

It may also be part of a larger protein or part of a fusion protein.

Preferably, the polypeptide of the present invention further includes at least one additional amino acid sequence which contains secretory or leader sequences, pro-sequences, sequences which help in purification such as multiple histidine residues, or additional sequences for stability during production of recombinant molecules.

Another object of the present invention concerns a variant of the polynucleotide or the polypeptide of the present invention, a precise definition of this term being given hereafter.

Preferably, said variant varies from the referent by conservative amino acid substitutions.

Preferably, at least one residue is substituted in said variant with another residue of similar characteristics.

Advantageously, the substitutions in said variant are among Ala, Val, Leu and Ile; among Ser and Thr, among the acidic residues Asp and Glu; among Asn and Gln; among the basic residues Lys and Arg; or among aromatic residues Phe and Tyr.

Preferably, in the variant of the present invention, several amino acids are substituted, deleted or added in any combination.

Preferably, 5-10, more preferably 1-5, more preferably 1-2 amino acids are substituted, deleted or added in any combination, in said variant.

Said variant may be a naturally occurring allelic variant of an *Ixodes ricinus* salivary gland polypeptide present in *Ixodes ricinus* salivary glands.

The present invention is also related to a recombinant vector comprising at least one element selected from the polynucleotide, the polypeptide, and the variant of the present invention or fragments thereof.

Another object of the present invention concerns a cell transfected by or comprising the recombinant vector according to the invention.

The present invention further includes an inhibitor directed against said polynucleotide, polypeptide, or variant.

Said inhibitor is preferably an antibody or an hypervariable portion thereof.

The present invention is also related to an hybridoma cell line expressing said inhibitor.

Another object of the present invention concerns a pharmaceutical composition comprising an adequate pharmaceutical carrier and an element selected from the group consisting of said polynucleotide, polypeptide, variant, vector, cell, inhibitor or a mixture thereof.

Preferably, said pharmaceutical composition presents anticoagulant properties and advantageously contains at least one polynucleotide selected from the group consisting of SEQ.ID.NO.7, SEQ.ID.NO.17, and SEQ.ID.NO.26, and fragments thereof or contains at least one polypeptide encoded by said polynucleotides or fragments thereof.

Preferably, the pharmaceutical composition presents immunomodulatory properties, and contains at least one polynucleotide selected from the group consisting of SEQ.ID.NO.12, SEQ.ID.NO.21, SEQ.ID.NO.26, and SEQ.ID.NO.31, and fragments thereof, or contains at least one polypeptide encoded by said polynucleotides or fragments thereof.

Another object of the invention is an immunological composition or vaccine for inducing an immunological response in a mammalian host to a tick salivary gland polypeptide which comprises at least one element of the group consisting of a) a polynucleotide of tick salivary glands according to the invention;
b) a polypeptide of tick salivary glands according to the invention;
c) a variant according to the invention;
d) epitope-bearing fragments, analogs, outer-membrane vesicles or cells (attenuated or otherwise) of components a) or b) or c);
e) possibly a carrier.

The present invention is also related to a method for treating or preventing a disease affecting a mammal, said method comprising the step of administrating to said mammal a sufficient amount of the pharmaceutical composition or the immunological composition or vaccine according to the invention, in order to prevent or cure either the transmission of pathogenic agents by tick, especially by *Ixodes ricinus*, or the symptoms of diseases induced by tick or pathogenic agents transmitted by tick.

The present invention is also related to the use of the pharmaceutical composition or the immunological composition or vaccine according to the invention for the manufacture of a medicament in the treatment and/or prevention of diseases induced by tick or pathogenic agents transmitted by tick, especially by *Ixodes ricinus*.

Advantageously, said medicament may be used in transplantation, in rheumatology, but also in general treatment.

Finally, another object of the invention is a diagnostic kit for detecting a disease or susceptibility to a disease induced or transmitted by tick, especially *Ixodes ricinus*, which comprises:

a) at least one tick salivary gland polynucleotide of the invention, or a fragment thereof;
b) or at least one nucleotide sequence complementary to that of a);
c) or at least one tick salivary gland polypeptide, of the invention or a fragment thereof;
d) or at least one variant according to the invention or a fragment thereof
e) or an inhibitor of the invention;
f) or a phage displaying an antibody of the invention whereby a), b), c), d), e), f) may comprise a substantial component.

DEFINITIONS

Figure 1:
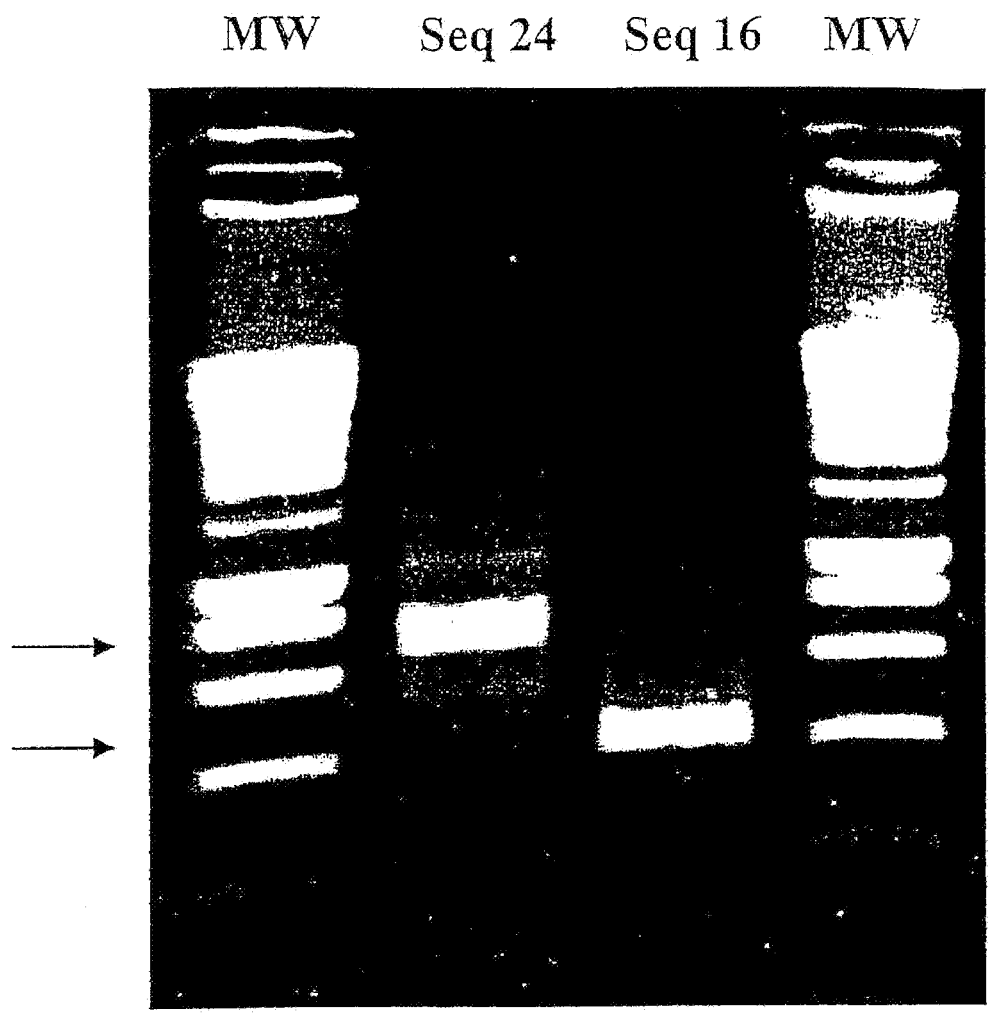
FIG. 1 shows sequencing of SEQ ID NO: 24 and 16.

"Putative anticoagulant, anti-complementary and immunomodulatory" polypeptides refer to polypeptides having the amino acid sequence encoded by the genes indicated in the table. These present homologies with anticoagulant, anti-complementary and immunomodulatory polypeptides already existing in databases. These polypeptides belong to the Class I and Class II sequences (see table).

"Putative anticoagulant, anti-complementary and immunomodulatory" cDNAs refer to polynucleotides having the nucleotide sequence described in the table, or allele variants thereof and/or their complements. These present homologies with anticoagulant, anti-complementary and immunomodulatory polynucleotides already existing in databases. These cDNAs belong to the Class I and Class II sequences (see table).

Some polypeptide or polynucleotide sequences present low or no homologies with already existing polypeptides or polynucleotides in databases. These belong to the Class III (see table).

<<Polypeptide>> refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslational natural processes or may be made by synthetic methods. Modifications include acetylation, acylation, ADP-ribosylation, amidation, covalent attachment of flavin, covalent attachment of a hem moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-linkings, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino of amino acids to proteins such as arginylation, and ubiquitination. See, for instance, PROTEINS—STRUCTURE AND MOLECULAR PROPERTIES, $2^{nd}$ Ed., T. E. Creighton, W.H. Freeman and Comany, New York, 1993 and Wolt, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182: 626-646 and Rattan et al, "Protein Synthesis: Posttranslational Modifications and Aging", Ann NY Acad Sci (1992) 663: 48-62.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "Polynucleotide" refers to triple-stranded regions comprising RNA or DNA or both RNA and DNA. The term "Polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "Polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more substitutions (preferably conservative), additions and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. Variants should retain one or more of the biological activities of the reference polypeptide. For instance, they should have similar antigenic or immunogenic activities as the reference polypeptide. Antigenicity can be tested using standard immunoblot experiments, preferably using polyclonal sera against the reference polypeptide. The immunogenicity can be tested by measuring antibody responses (using polyclonal sera generated against the variant polypeptide) against purified reference polypeptide in a standard ELISA test. Preferably, a variant would retain all of the above biological activities.

"Identity" is a measure of the identity of nucleotide sequences or amino acid sequences. In general, the sequences are aligned so that the highest order match is obtained. "Identify" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds, Humana Press, New Jersey, 1994; SEQUENCE ANALYSIS IN MOLECULAR BIOLOGY, von Heijne, G., Academic Press, 1987; and SEQUENCE ANALYSIS PRIMER, Gribskov, M. and Devereux, J., eds, M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1998) 48: 1073). Methods commonly employed to determine identity or similarity between two sequences include, but are not limited to those disclosed in Guide to Huge Computers, Martin J. Bishop, ed., Academic Press, San Diego, 1994, and Carillo, H., and Lipton, D., *SIAM J Applied Math* (1988) 48: 1073. Methods to determine identity and similarity are codified in computer programs. Preferred computer program methods to determine identity and similarity between two sequences include, but are not limited to, GCG program package (Devereux, J., et al., *J Molec Biol* (1990) 215: 403). Most preferably, the program used to determine identity levels was the GAP program, as was used in the Examples hereafter.

As an illustration, by a polynucleotide having a nucleotide sequence having at least, for example, 95% "identity" to a reference nucleotide sequence is intended that the nucleotide sequence of the polynucleotide is identical to the reference sequence except that the polynucleotide sequence may include an average up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Fragments of *I. ricinus* salivary gland polypeptides are also included in the present invention. A fragment is a polypeptide having an amino acid sequence that is the same as a part, but not all, of the amino acid sequence of the aforementioned *I. ricinus* salivary gland polypeptides. As with *I. ricinus* salivary gland polypeptides, fragment may be "free-standing" or comprised within a larger polypeptide of which they form a part or region, most preferably as a single continuous region. Representative examples of polypeptide fragments of the invention, include, for example, fragments from about amino acid number 1-20, 21-40, 41-60, 61-80, 81-100, and 101 to the end of the polypeptide. In this context "about" includes the particularly recited ranges larger or smaller by several, 5, 4, 3, 2 or 1 amino acid at either extreme or at both extremes.

Preferred fragments include, for example, truncated polypeptides having the amino acid sequence of the *I. ricinus* salivary gland polypeptides, except for deletion of a continuous series of residues that includes the amino terminus, or a continuous series of residues that includes the carboxyl terminus and/or transmembrane region or deletion of two continuous series of residues, one including the amino terminus and one including the carboxyl terminus. Also preferred are fragments characterised by structural or functional attributes such as fragments that comprise alpha-helix and alpha-helix forming regions, beta-sheet and beta-sheet forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate *I. ricinus* salivary gland protein activity, including those with a similar activity or an improved activity, or with a decreased undesirable activity. Also included are those that are antigenic or immunogenic in an animal or in a human.

EXAMPLES

Example 1

Characterisation of the Induced Genes

Genes are induced in the salivary glands of *Ixodes ricinus* during the slow-feeding phase of the blood meal. The cloning of these genes was carried out by setting up two complementary DNA (cDNA) libraries. The first one is a subtractive library based on the methodology described by Lisitsyn et al. (*Science* 259, 946-951, 1993) and improved by Diatchenko et al. (*Proc. Natl. Acad. Sci. USA* 93, 6025-6030, 1996). This library cloned selectively induced mRNA during the tick feeding phase. The second library is a full-length cDNA library, which was constructed by using the basic property of mRNAs (presence of a polyA tail in its 3' end and a cap structure in its 5' end). This cDNA library permitted the cloning of full-length cDNAs, corresponding to some incomplete cDNA sequences identified in the subtractive cDNA library.

The subtractive library was set up by subtracting uninduced-cDNAs (synthetized from mRNAs equally expressed in the salivary glands of both unfed and engorged ticks) from induced-cDNAs (synthesised from mRNAs differentially expressed in the salivary gland at the end of the slow-feeding phase). The induced-cDNAs was digested by a restriction enzyme, divided into two aliquots, and distinctively modified by the addition of specific adapters. As for the induced-cDNAs, the uninduced cDNAs was also digested by the same restriction enzyme and then mixed in excess to each aliquot of modified induced-cDNA. Each mixture of uninduced-/induced-cDNAs was subjected to a denaturation step, immediately followed by an hybridisation step, leading to a capture of homologous induced-cDNAs by the uninduced-cDNA. Each mixture was then mixed together and subjected again to a new denaturation/hybridisation cycle. Among the hybridised cDNA molecules, the final mixture comprises induced-cDNAs with different adapters at their 5' and 3' end. These relevant cDNAs were amplified by polymerase chain reaction (PCR), using primers specific to each adapter located at each end of the cDNA molecules. The PCR products were then ligated into the pCRII™ vector by A-T cloning and cloned in an TOP-10 *E. coli* strain. The heterogeneity of this subtractive library was evaluated by sequencing 96 randomly chosen recombinant clones. The "induced" property of these cDNA sequences was checked by reverse transcription-PCR (RT-PCR) on mRNA extracted from salivary glands of engorged and unfed ticks. Finally, the full-length induced-cDNA was obtained by screening the full-length cDNA library using, as a probe, some incomplete induced-cDNAs isolated from the subtractive library. These full-length induced DNA molecules were sequenced and compared to known polypeptide and polynucleotide sequences existing in the EMBL/GenBank databases.

The full-length cDNA library was set up by using the strategy developed in the "CapFinder PCR cDNA Library Construction Kit" (Clontech). This library construction kit utilises the unique CapSwitch™ oligonucleotide (patent pending) in the first-strand synthesis, followed by a long-distance PCR amplification to generate high yields of full-length, double-stranded cDNAs. All commonly used cDNA synthesis methods rely on the ability of reverse transcriptase to transcribe mRNA into single stranded DNA in the first-strand reaction. However, because the reverse transcriptase cannot always transcribe the entire mRNA sequence, the 5' ends of genes tend to be under-represented in cDNA population. This is particularly true for long mRNAs, especially if the first-strand synthesis is primed with oligo(dT) primers only, or if the mRNA has a persistent secondary structure. Furthermore, the use of T4 DNA polymerase to generate blunt cDNA ends after second-strand synthesis commonly results in heterogeneous 5' ends that are 5-30 nucleotides shorter than the original mRNA. In the CapFinder cDNA synthesis method, a modified oligo(dT) primer is used to prime the first-strand reaction, and the CapSwitch oligonucleotide acts as a short, extended template at the 5' end for the reverse transcriptase. When the reverse transcriptase reaches the 5' end of the mRNA, the enzyme switches templates and continues replicating to the end of the CapSwitch oligonucleotide. This switching in most cases occurs at the 7-methylguanosine cap structure, which is present at the 5' end of all eukaryotic mRNAs. The resulting full-length single stranded cDNA contains the complete 5' end of the mRNA as well as the sequence complementary to the CapSwitch oligonucleotide, which then serves as a universal PCR priming site (CapSwitch anchor) in the subsequent amplification. The CapSwitch-anchored single stranded cDNA is used directly (without an intervening purification step) for PCR. Only those oligo(dT)-primed single stranded cDNAs having a CapSwitch anchor sequence at the 5' end can serve as templates and be exponentially amplified using the 3' and 5' PCR primers. In most cases, incomplete cDNAs and cDNA transcribed from poly-A RNA will not be recognised by the CapSwitch anchor and therefore will not be amplified.

At the end of these reactions, the full-length cDNA PCR products was ligated into the pCRII cloning vector (Invitrogen) and used for the transformation of XL2 E. coli strain. The full-length cDNA library was then screened by using, as a probe, the incomplete induced-cDNAs isolated from the subtractive library.

Ninety-six clones of subtractive library were randomly sequenced, and their DNA and amino acid translated sequences were compared to DNA and protein present in databases. Among these, 27 distinct family sequences were identified, and 3 of them were selected for further characterisation of their corresponding full-length mRNA sequence. These 3 sequences matched the sequence of i) the human tissue factor pathway inhibitor (TFPI), ii) the human thrombin inhibitor gene, and iii) a snake venom zinc-dependent metalloprotease protein. These genes encode proteins that could be involved in the inhibition of the blood coagulation. The other 24 family sequences presented low or no homologies with polynucleotide and polypeptide sequences existing in databases. Screening of the full-length cDNA library using oligonucleotide probes specific to the 3 previously selected subtractive clones lead to the recovery of the corresponding full-length cDNAs. Random screening of this library led to the selection of 2 other clones. One is closely homologous to an interferon-like protein, whereas the other shows homologies to the *Streptococcus equi* M protein, an anti-complement protein.

These polypeptides expressed by *I. ricinus* salivary glands include the polypeptides encoded by the cDNAs defined in the tables, and polypeptides comprising the amino acid sequences which have at least 75% identity to that encoded by the cDNAs defined in the tables over their complete length, and preferable at least 80% identity, and more preferably at least 90% identity. Those with about 95-99% are highly preferred.

The *I. ricinus* salivary gland polypeptides may be in the form of the "mature" protein or may be a part of a larger protein such as a fusion protein. It may be advantageous to include an additional amino acid sequence, which contains secretory or leader sequences, pro-sequences, sequences which help in purification such as multiple histidine residues, or an additional sequence for stability during recombinant production.

Preferably, all of these polypeptide fragments retain parts of the biological activity (for instance antigenic or immunogenic) of the *I. ricinus* salivary gland polypeptides, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5-10, 1-5, or 1-2 amino acids are substituted, deleted, or added in any combination. Most preferred variants are naturally occurring allelic variants of the *I. ricinus* salivary gland polypeptide present in *I. ricinus* salivary glands.

The *I. ricinus* salivary gland polypeptides of the invention can be prepared in any suitable manner. Such polypeptides include isolated naturally occurring polypeptides, recombinant polypeptides, synthetic polypeptides, or polypeptides produced by a combination of these methods. Means for preparing such polypeptides are well understood in the art.

The *I. ricinus* salivary gland cDNAs (polynucleotides) include isolated polynucleotides which encode *I. ricinus* salivary gland polypeptides and fragments thereof, and polynucleotides closely related thereto. More specifically, *I. ricinus* salivary gland cDNAs of the invention include a polynucleotide comprising the nucleotide sequence of cDNAs defined in the table, encoding a *I. ricinus* salivary gland polypeptide. The *I. ricinus* salivary gland cDNAs further include a polynucleotide sequence that has at least 75% identity over its entire length to a nucleotide sequence encoding the *I. ricinus* salivary gland polypeptide encoded by the cDNAs defined in the tables, and a polynucleotide comprising a nucleotide sequence that is at least 75% identical to that of the cDNAs defined in the tables, in this regard, polynucleotides at least 80% identical are particularly preferred, and those with at least 90% are especially preferred. Furthermore, those with at least 95% are highly preferred and those with at least 98-99% are most highly preferred, with at least 99% being the most preferred. Also included under *I. ricinus* salivary gland cDNAs is a nucleotide sequence, which has sufficient identity to a nucleotide sequence of a cDNA defined in the tables to hybridise under conditions usable for amplification or for use as a probe or marker. The invention also provides polynucleotides which are complementary to such *I. ricinus* salivary gland cDNAs.

These nucleotide sequences defined in the tables as a result of the redundancy (degeneracy) of the genetic code may also encode the polypeptides encoded by the genes defined in the tables.

When the polynucleotides of the invention are used for the production of an *I. ricinus* salivary gland recombinant polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or preproprotein sequence, or other fusion peptide portions. For example, a marker sequence, which facilitates purification of the fused polypeptide can be encoded. Preferably, the marker sequence is a hexa-histidine peptide, as provided in the pQE vector (Qiagen, Inc.) and described in Gentz et al, *Proc Natl Acad Sci USA* (1989) 86:821-824, or is an HA tag, or is glutathione-s-transferase. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding *I. ricinus* salivary gland protein variants comprising the amino acid sequence of the *I. ricinus* salivary gland polypeptide encoded by the cDNAs defined by the table respectively in which several, 10-25, 5-10, 1-5, 1-3, 1-2 or 1 amino acid residues are substituted, deleted or added, in any combination. Most preferred variant polynucleotides are those naturally occurring *I. ricinus* sequences that encode allelic variants of the *I. ricinus* salivary gland proteins in *I. ricinus*.

The present invention further relates to polynucleotides that hybridise preferably stringent conditions to the herein above-described sequences. As herein used, the term "stringent conditions" means hybridisation will occur only if there is at least 80%, and preferably at least 90%, and more preferably at least 95%, yet even more preferably 97-99% identity between the sequences.

Polynucleotides of the invention, which are identical or sufficiently identical to a nucleotide sequence of any gene defined in the table or a fragment thereof, may be used as hybridisation probes for cDNA clones encoding *I. ricinus* salivary gland polypeptides respectively and to isolate cDNA clones of other genes (including cDNAs encoding homologs and orthologs from species other than *I. ricinus*) that have a high sequence similarity to the *I. ricinus* salivary gland cDNAs. Such hybridisation techniques are known to those of skill in the art. Typically these nucleotide sequences are 80% identical, preferably 90% identical, more preferably 95% identical to that of the referent. The probes generally comprise at least 15 nucleotides, preferably, at least 30 nucleotides or at least 50 nucleotides. Particularly preferred probes range between 30 and 50 nucleotides. In one embodiment, to obtain a polynucleotide encoding *I. ricinus* salivary gland polypeptide, including homologues and orthologues from species other than *I. ricinus*, comprises the steps of screening an appropriate library under stringent hybridisation conditions with a labelled probe having a nucleotide sequence contained in one of the gene sequences defined by the table, or a fragment thereof; and isolating full-length cDNA clones containing said polynucleotide sequence. Thus in another aspect, *I. ricinus* salivary gland polynucleotides of the present invention further include a nucleotide sequence comprising a nucleotide sequence that hybridise under stringent condition to a nucleotide sequence having a nucleotide sequence contained in the cDNAs defined in the tables or a fragment thereof. Also included with *I. ricinus* salivary gland polypeptides are polypeptides comprising amino acid sequences encoded by nucleotide sequences obtained by the above hybridisation conditions (conditions under overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 microgram/ml denatured, sheared salmon sperm DNA, followed by washing the filters in 0.1×SSC at about 65° C.)

The polynucleotides and polypeptides of the present invention may be employed as research reagents and materials for the development of treatments and diagnostics tools specific to animal and human disease.

This invention also relates to the use of *I. ricinus* salivary gland polypeptides, or *I. ricinus* salivary gland polynucleotides, for use as diagnostic reagents.

Materials for diagnosis may be obtained from a subject's cells, such as from blood, urine, saliva, tissue biopsy.

Thus in another aspect, the present invention relates to a diagnostic kit for a disease or susceptibility to a disease which comprises:
(a) an *I. ricinus* salivary gland polynucleotide, preferably the nucleotide sequence of one of the gene sequences defined by the table, or a fragment thereof;
(b) a nucleotide sequence complementary to that of (a);
(c) an *I. ricinus* salivary gland polypeptide, preferably the polypeptide encoded by one of the gene sequences defined in the table, or a fragment thereof;
(d) an antibody to an *I. ricinus* salivary gland polypeptide, preferably to the polypeptide encoded by one of the gene sequences defined in the table; or
(e) a phage displaying an antibody to an *I. ricinus* salivary gland polypeptide, preferably to the polypeptide encoded by one of the cDNAs sequences defined in the table.

It will be appreciated that in any such kit, (a), (b), (c), (d) or (e) may comprise a substantial component.

Another aspect of the invention relates to a method for inducing an immunological response in a mammal which comprises inoculating the mammal with *I. ricinus* salivary gland polypeptide or epitope-bearing fragments, analogues, outer-membrane vesicles or cells (attenuated or otherwise), adequate to produce antibody and/or T cell immune response to protect said animal from bacteria and viruses which could be transmitted during the blood meal of *I. ricinus* and related species. In particular the invention relates to the use of *I. ricinus* salivary gland polypeptides encoded by the cDNAs defined in the tables. Yet another aspect of the invention relates to a method of inducing immunological response in a mammal which comprises, delivering *I. ricinus* salivary gland polypeptide via a recombinant vector directing expression of *I. ricinus* salivary gland polynucleotide in vivo in order to induce such an immunological response to produce antibody to protect said animal from diseases transmitted by *I. ricinus* ticks or other related species (Lyme disease, tick encephalitis virus disease, . . . ).

A further aspect of the invention relates to an immunological composition or vaccine formulation which, when introduced into a mammalian host, induces an immunological response in that mammal to a *I. ricinus* salivary gland polypeptide wherein the composition comprises a *I. ricinus* salivary gland cDNA, or *I. ricinus* salivary gland polypeptide or epitope-bearing fragments, analogs, outer-membrane vesicles or cells (attenuated or otherwise). The vaccine formulation may further comprise a suitable carrier. The *I. ricinus* salivary gland polypeptide vaccine composition is preferably administered orally or parenterally (including subcutaneous, intramuscular, intravenous, intradermal injection). Formulations suitable for parenteral administration include aqueous and non-aqueous sterile injection solutions which may contain anti-oxidants, buffers, bacteriostats and solutes which render the formulation iotonic with the blood of the recipient; and aqueous and non-aqueous sterile suspensions which may include suspending agents or thickening agents. The formulations may be presented in unit-dose or multi-dose containers, for example; sealed ampoules and vials and may be stored in a freeze-dried condition requiring only the addition of the sterile liquid carrier immediately prior to use. The vaccine formulation may also include adjuvant systems for enhancing the immunogenicity to the formulation, such as oil-in water systems and other systems known in the art. The dosage will depend on the specific activity of the vaccine and can be readily determined by routine experimentation.

Yet another aspect relates to an immunological/vaccine formulation which comprises the polynucleotide of the invention. Such techniques are known in the art, see for example Wolff et al, *Sciences*, (1990) 247: 1465-8.

Another aspect of the invention related to the use of these *I. ricinus* salivary gland polypeptides as therapeutic agents. In considering the particular potential therapeutic areas for such products, the fields covered by these products are: haematology (particularly coagulation clinics), transplantation (for immunosuppression control), rheumatology (for anti-inflammatories), and general treatment (for specific or improved anaesthetics).

TABLE 1

Sequences identified in the subtractive and the cDNA full-length libraries

| | Motifs | Similar sequences in databases | Score | Class |
|---|---|---|---|---|
| Seq. 1 | | No significant identity | | III |
| Seq. 2 | | No significant identity | | III |
| Seq. 3 | | No significant identity | | III |
| Seq. 4 | | No significant identity | | III |
| Seq. 5 | Prokariotic mbre lipoprotein lipid attachment site | No significant identity | | III |
| Seq. 6 | | *R. melioti* Nitrogen fixation (fixF) | 0.00089 | III |
| | | Human Apolipoprotein B-100 | 0.0045 | III |
| | | Hu. mRNA for cAMP response element (CRE-BP1) binding prot | 0.057 | III |
| Seq. 7 | Kunitz family of serine protease inhibitor | Human BAC clone GS345D13 | $4.7^{13}$ | I |
| | | *H. sap* Tissue factor Pathway Inhibitor | $4^{-12}$ | I |
| Seq. 8 | | Amino acid sequence of Seq. 7 | | |
| Seq. 9 | Prokariotic membrane lipoprotein lipid attachment | No significant identity | | III |
| Seq. 10 | | Pea mRNA for GTP binding protection. | 0.48 | III |
| Seq. 11 | | No significant identity | | III |
| Seq. 12 | | IL-11 R-Béta gene | 0.18 | II |
| Seq. 13 | | No significant identity | | III |
| Seq. 14 | | *C. gloeosporioides* cutinase gene | 0.082 | III |
| Seq. 15 | | No significant identity | | III |
| Seq. 16 | | Mouse mRNA for secretory protection cont. thrombospondin motifs | 0.014 | III |
| Seq. 17 | Zinc dependent metallopeptidase family | *B. jararaca* mRNA for jararhagin | $1.1^{-5}$ | I |
| | | *Agkistrodon contortrix* metalloproteinase precursor | $3.9^{-5}$ | I |
| Seq. 18 | | Amino acid sequence of Seq. 17 | | |
| Seq. 19 | | *O. aries* gene for ovine Interferon-alpha | 0.7 | II |
| | | Interferon-omega 45 | 0.88 | II |
| | | Interferon-omega 20 | 0.89 | II |
| | | RCPT PGE2 | 0.85 | III |
| | | PGE Rcpt EP2 | 0.85 | III |
| Seq. 20 | | No significant identity | | III |
| Seq. 21 | | IgG1L chain directed against human IL2 rcpt Tac protein | 0.19 | II |
| | | Var region of light chain of MAK447/179 | 0.2 | II |
| Seq. 22 | | No significant identity | | III |
| Seq. 23 | | No significant identity | | III |
| Seq. 24 | | *Mus Musculus* neuroactin | 0.42 | III |
| Seq. 25 | | No significant identity | | III |
| Seq. 26 | | *H. sapiens* thrombin inhibitor | $2.1^{-12}$ | I |
| | | Cycloplasmic antiproteinase 38 kDa intracellular serine | $2.3^{-12}$ | I |
| Seq. 28 | | No significant identity | | III |
| Seq. 29 | | No significant identity | | III |
| Seq. 30 | | *Mus musculus* transcription factor ELF3 (fasta) | 0.053 | III |
| Seq. 31 | | *Homo sapiens* putative leukocyte interferon-related protein | 1.70E−22 | II |
| Seq. 33 | | *R. norvegicus* mRNA for common antigen-related protein | 4.80E−09 | II |

(SEQ. ID. NO. 26 (Iris): homology with *H. sapiens* thrombin inhibitor 2.1-12, class I
Class I: putative anticoagulant homologs;
Class II: putative immunomodulatory homologs;
Class III: low or no homologies found in the databases).

TABLE 2

Biological characteristics of the selected clones

| Clone | Full-length sequences similarly to databases | Fasta/Blastp Scores[a] | ORF (aa) | Motifs | Signal peptide scores[b] | Sp length/ Prob. | Nucleotide in position −3[c] |
|---|---|---|---|---|---|---|---|
| Seq 31 | Homo sapiens putative interferon-related gene (SKMc15) [U09585] | 1, $8.10^{-36}$/$1.10^{-71}$ | 426 | | D 5, 4/F[e] | 48aa/8, $4.10^{-1}$ | G |
| Seq 33 | *R. norvegicus* leukocyte common antigen (LAR) mRNA [X83546] | 7, $8.10^{-11}$/N | 274 | | 10, 2/S | 18aa/7, $4.10^{-3}$ | A |
| Seq 17 | Mouse mRNA for secretory protein containing thrombospondin motives [D67076] | 0, 002/$6.10^{-7}$ | 489 | Metallopeptidase | 7, 9/S | 19aa/7, $4.10^{-4}$ | G |
| Seq 26 | Pig leukocyte elastase inhibitor mRNA [P80229] | 0/$7.10^{-67}$ | 378 | Serpin | 8, 5/S | 51aa/3, $28.10^{-3}$ | A |
| Seq 7 | Human Tissue Factor Pathway Inhibitor [P48307] | 4, $8.10^{-12}$/$2.10^{-5}$ | 87 | Kunitz | 6, 5/S | 19aa:1, $8.10^{-4}$ | G |

[a]No score (N)
[b]Succeeded (S) and Failed (F)
[c]Guanine (G) and Adenine (A)
[d]von Heijne analysis
[e]McGeoch analysis

Example 2

Construction of a Representational Difference Analysis (RDA) Subtractive Library The salivary glands of 5 day engorged or unfed free of pathogen *I. ricinus* female adult ticks were used in this work.

When removed, these glands were immediately frozen in liquid nitrogen and stored at −80° C. To extract RNA messengers (mRNA), the salivary glands were crushed in liquid nitrogen using a mortar and a pestle. The mRNAs were purified by using an oligo-dT cellulose (Fast Track 2.0 kit, Invitrogen, Groningen, The Netherlands). Two micrograms of mRNAs were extracted from 200 salivary glands of fed ticks, and 1.5 μg of mRNAs were also extracted from 1,000 salivary glands of unfed ticks.

All procedures were performed as described by Hubank and Schatz Nucl. Acid Res Dec. 25, vol 22-25 p 5640-5648 (1994). Double-stranded cDNAs were synthesised using the Superscript Choice System (Life Technologies, Rockville, Md. USA). The cDNAs were digested with DpnII restriction enzyme, ligated to R-linkers, amplified with R-24 primers (Hubank and Schatz, 1994), and finally digested again with the same enzyme to generate a "tester" pool consisting of cDNAs from salivary glands of fed ticks and a "driver" pool consisting of cDNAs from salivary glands of unfed ticks. The first round of the subtractive hybridisation process used a tester/driver ratio of 1:100. The second and third rounds utilised a ratio of 1:400 and 1:200,000, respectively. After three cycles of subtraction and amplification, the DpnII-digested differential products were subdivided according to size into 4 different fractions on a 1.7% electrophoresis agarose gel, and subcloned the BamHI site of the pTZ19r cloning vector. The ligated product was used to transform TOP-10 *E. coli* competent cells (Invitrogen, Groningen, The Nederlands). Nine thousand six hundred clones of this subtractive library were randomly selected, and individually put in 96-well microplates and stored at −80° C. This subtractive library was analysed by sequencing 89 randomly chosen clones, using M13 forward and reverse primers specific to a region located in the pT19r cloning vector. The DNA sequences of these 89 clones were compared, and 27 distinct family sequences were identified. Homology of these sequences to sequences existing in databases is presented in Table 1.

The subtractive sequences 1 to 27 are presented in the sequence-listing file (except for sequences 7, 17 and 26 whose complete mRNA sequences are presented; see also Example 2). Three sequences (SEQ.ID.NO.7, 17 and 26) were selected for further characterisation of their corresponding full-length mRNA sequence. These 3 sequences matched the sequence of i) the human tissue factor pathway inhibitor (TFPI), ii) a snake venom zinc dependent metallopeptidase protein, and iii) the human thrombin inhibitor protein, corresponding to SEQ.ID.NO.7, 17 and 26, respectively. These genes encode proteins which could be involved in the inhibition of the blood coagulation or in the modulation of the host immune response.

Example 3

Construction of the Full Length cDNA Library and Recovery of Full Length cDNAs Sequences by Screening of this Full Length cDNA Library This library was set up using mRNAs extracted from salivary glands of engorged ticks. The mRNAs (80 ng) were subjected to reverse transcription using a degenerated oligo-dT primer (5'A(T)30VN-3'), the Smart™ oligonucleotide (Clontech, Palo Alto, USA), and the Superscript II reverse transcriptase (Life Technologies, Rockville, Md., USA). The single strand cDNA mixture was used as template in a hot start PCR assay including the LA Taq polymerase (Takara, Shiga, Japan), the modified oligo-dT primer and a 3'-Smart primer specific to a region located at the 5' end of the Smart™ oligonucleotide. The PCR protocol applied was: 1 min at 95° C., followed by 25 sec at 95° C./5 min at 68° C., 25 times; and 10 min at 72° C. The amplified double stranded cDNA mixture was purified with a Centricon 30 concentrator (Millipore, Bedford, USA). The cDNAs were divided into 4 fractions ranging from 0.3 to 0.6 kb, 0.6 to 1 kb, 1 kb to 2 kb, and 2 kb to 4 kb on a 0.8% high grade agarose electrophoresis gel. Each fraction was recovered separately by using the Qiaex II extraction kit (Qiagen, Hilden, Germany). The 4 fractions were ligated individually into the pCRII cloning vector included in the TOPO cloning kit (Invitrogen, Groningen, The Netherlands). The ligated fractions were then used to transform XL2-Blue ultracompetent *E. coli* cells (Stratagene, Heidelburg, Germany). The resulted recombinant clones were stored individually in microplates at −80° C. Ten clones were randomly chosen for partial or complete sequencing. As a result of this procedure, 2 cDNA sequences (SEQ.ID.NO.31 and SEQ.ID.NO.33, see Table 1) were selected for their homology to sequence databases. One is closely homologous to an interferon-related protein (SEQ.ID.NO.31), whereas the other shows homologies to the *Rattus norvegicus* leukocyte common antigen-related protein (SEQ.ID.NO.33).

The 4 different fractions of the full-length cDNA library were screened with radiolabelled oligonucleotide probes specific to selected clones identified in the subtractive cDNA library. The labelling of these oligo probes was performed as described in "Current Protocols in Molecular Biology" (Ausubel et al, 1995, J. Wiley and sons, Eds). These 4 different fractions were then plated on nitrocellulose membranes and grown overnight at 37° C. These membranes were denatured in NaOH 0.2M/NaCl 1.5M, neutralised in Tris 0.5M pH 7.5-NaCl 1.5M and fixed in 2×SSC (NaCl 0.3 M/Citric Acid Trisodium di-hydrated 0.03 M). The membranes were heated for 90 min. at 80° C., incubated in a pre-hybridisation solution (SSC 6×, Denhardt's 10×, SDS 0.1%) at 55° C. for 90 min., and finally put overnight in a preheated hybridisation solution containing a specific radiolabelled oligonucleotide probe at 55° C. The hybridised membranes were washed 3 times in a SSC 6× solution at 55° C. for 10 min, dried and exposed on Kodak X-OMAT film overnight at −80° C.

The full-length cDNA library was also analysed by sequencing a set of clones. The resulted DNA sequences were compared to EMBL/GenBank databases and were used to set up oligonucleotide probes to recover other corresponding clones. In this way, the complete consensus mRNA sequence of the SEQ.ID.NO.28 and 29 was confirmed by the recovery of two other clones corresponding to these sequences. Only one full-length cDNA clone corresponding to the subtractive clone 17 was isolated. Therefore, to identify the complete sequence of the SEQ.ID.NO.17 and SEQ.ID.NO.26, the Rapid Amplification of cDNA Ends (RACE) method was applied.

The RACE methodology was performed as described by Frohman et al. Rapid amplification of cDNA Cold Spring Harbor Laboratory press, Cold Spring Harbor, N.Y. p 381-409 (Dieffen bock et al eds) (1995). The reverse transcription step was carried out using 10 ng of mRNAs extracted from salivary glands of engorged ticks and the Thermoscript Reverse transcriptase (Life technologies, Rockville, Md., USA). All gene specific primers (GSP) had an 18 base length with a 61% G/C ratio. The amplified products were subjected to an agarose gel electrophoresis and recovered by using an isotachophorese procedure. The cDNAs were cloned into the pCRII-TOPO cloning vector (Invitrogen, Groningen, The Netherlands). To identify the consensus cDNA sequence, different clones were sequenced, and their sequence was compared to their known corresponding sequence. Therefore, the complete cDNA sequences of the clones 17 and 26 isolated in the subtractive library were obtained by this RACE procedure (FIG. 1).

Example 4

Analysis of the Full Sequences of 5 Selected Clones

The sequences of selected clones (SEQ.ID.NO.7, 17, 26, 31 and 33) allowed identification of the open reading frames, from which the amino sequences were deduced. These potential translation products have a size between 87 and 489 amino acids (see table 2). In order to evaluate, in silico, their respective properties, the amino acid sequences and the nucleotide sequences of said 5 open frames were compared with the databases using the tFasta and Blastp algorithms.

These comparisons show that SEQ.ID.NO.7 is highly homologous to the human Tissue Factor Pathway Inhibitor (TFPI). TFPI is an inhibitor of serine proteases having 3 tandemly arranged Kunitz-type-protease-inhibitor (KPI) domains. Each of these units or motifs has a particular affinity for different types of proteases. The first and second KPI domains are responsible for the respective inhibition of VIIa and Xa coagulation factors. The third KPI domain apparently has no inhibitory activity. It should be noted that the corresponding polypeptide sequence of SEQ.ID.NO.7 cDNA clone is homologous to the region of the first KPI domain of TFPI and that the KPI is perfectly kept therein. This similarity suggests that the SEQ.ID.NO.7 protein is a potential factor VIIa inhibitor.

The amino sequence deduced from the SEQ.ID.NO.28 clone has a great homology with 3 database sequences, namely: mouse TIS7 protein, rat PC4 protein and human SKMc15 protein. These 3 proteins are described as putative interferon type factors. They possess very well conserved regions of the B2 interferon protein. Therefore, it is proposed that the SEQ.ID.NO.31 protein has advantageous immuno-modulatory properties.

Sequences SEQ.ID.NO.17 and SEQ.ID.NO.26 were compared with databases showing homology with the Gloydius halys (sub-order of ophidians) M12b metallopeptidase and the porcine elastase inhibitor belonging to the super-family of the serine protease inhibitors (Serpin), respectively. The amino sequences of these 2 clones also have specific motifs of said families. It is proposed that said proteins have advantageous anticoagulant and immuno-modulatory properties.

Finally, the SEQ.ID.NO.33 clone has a weak homology with the *R. norvegicus* leukocyte common antigen (LAR) that is an adhesion molecule. It is thus possible that the SEQ.ID.NO.33 protein has immunomodulatory properties related to those expressed by the LAR protein.

Due to their potential properties, most of the proteins examined are expected to be secreted in the tick saliva during the blood meal. Accordingly, tests were made for finding the presence of a signal peptide at the beginning of the deduced amino sequences. By the McGeoch method (Virus Res 3: 271-286, 1985), signal peptide sequences were detected for the SEQ.ID.NO.7, SEQ.ID.NO.17, SEQ.ID.NO.26 and SEQ.ID.NO.33 deduced amino sequences. It seems that said proteins are secreted in the tick salivary gland. Furthermore, the presence of a Kozak consensus sequence was observed upstream of the coding sequences of all examined clones. This indicates that their mRNAs potentially could be translated to proteins.

Example 5

Figure 2:
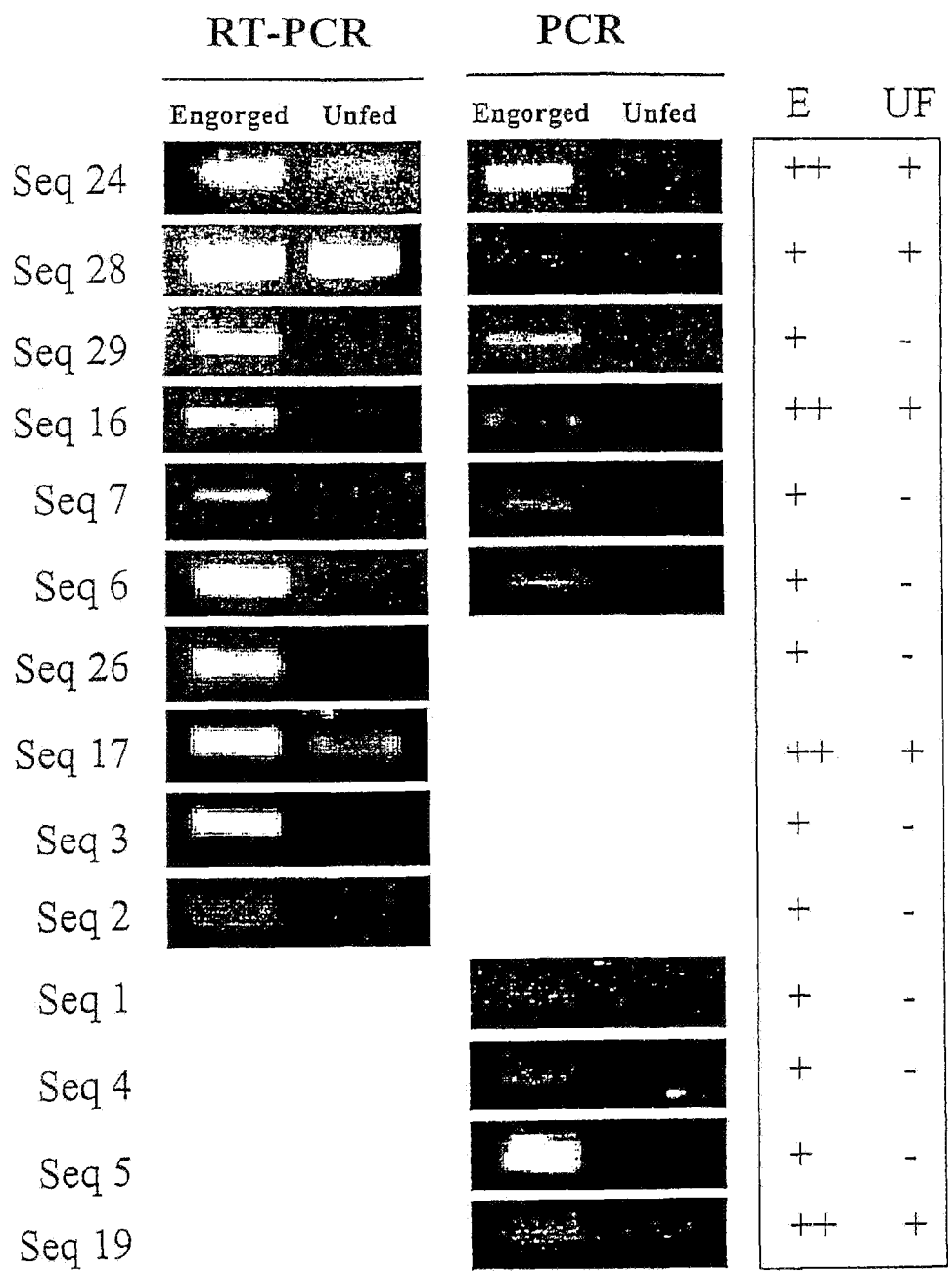
FIG. 2 shows that the expression of the selected sequences is induced in salivary glads of 5 day engorged ticks, except for the sequence 31 that is expressed at a similar level in salivary glads of engorged and unfed ticks.

Evaluation of the Differential Expression of the cDNA Clones Isolated in the Subtractive and Full-Length cDNA Libraries The differential expression of the mRNAs corresponding to the 5 full-length selected clones (SEQ.ID.NO.7, SEQ.ID.NO.17, SEQ.ID.NO.26, SEQ.ID.NO.31 and SEQ.ID.NO.33) and of 9 subtractive clones was assessed using a PCR and a RT-PCR assays (FIG. 2).

The PCR assays were carried out using as DNA template cDNAs obtained from a reverse transcription procedure on mRNAs extracted from salivary glands either of engorged or of unfed ticks.

Each PCR assay included pair of primers specific to each target subtractive or cDNAs full-length sequence. PCR assays were performed in a final volume of 50 µl containing 20 µM primers, 0.2 mM deoxynucleotide (dATP, dCTP, dGTP and dTTP; Boehringer Mannheim GmbH, Mannheim, Germany), PCR buffer (10 mM TrisHCl, 50 mM KCl, 2.5 mM. MgCl2, pH 8.3) and 2.5 U of Taq DNA polymerase (Boehringer Mannheim GmbH, Mannheim, Germany).

DNA samples were amplified for 35 cycles under the following conditions: 94 C for 1 min., 72 C for 1 min. and 64 C for 1 min, followed by a final elongation step of 72 C for 7 min.

The RT-PCR assay was carried out on the 5 selected full-length cDNA clones and on 5 cDNA subtractive clones. The mRNAs used as template in the reverse transcription assay was extracted from salivary glands of engorged and unfed *I. ricinus* ticks. The reverse transcription assays were performed using a specific primer (that target one the selected sequences) and the "Thermoscript Reverse transcriptase" (Life technologies, Rockville, Md., USA) at 60° C. for 50 min. Each PCR assay utilised the reverse transcription specific primer and an another specific primer. The PCR assays were performed in a final volume of 50 µl containing 1 µM primers, 0.2 mM deoxynucleotide (dATP, dCTP, dGTP and dTTP; Boehringer Mannheim GmbH, Mannheim, Germany), PCR buffer (10 mM Tris HCl, 50 mM KCl, 2.5 mM MgCl$_2$, pH 8.3) and 2.5 U of Expand High Fidelity polymerase (Roche, Bruxelles, Belgium). Single stranded DNA samples were amplified for 30 cycles under the following conditions: 95° C. for 1 min., 72° C. for 30 sec. and 60° C. for 1 min, followed by a final elongation step of 72° C. for 7 min.

The FIG. 2 shows that the expression of the selected sequences is induced in salivary glands of 5 day engorged ticks, except for the sequence 31 that is expressed at a similar level in salivary glands of engorged and unfed ticks. The expression of the other mRNAs could be either induced specifically or increased during the blood meal.

Example 6

Expression of Recombinant Proteins in Mammal Cells

The study of the properties of isolated sequences involves the expression thereof in expression systems allowing large amounts of proteins encoded by these sequences to be produced and purified.

The DNA sequences of the 5 selected clones (SEQ. ID.NO.7, SEQ.ID.NO.17, SEQ.ID.NO.26, SEQ.ID.NO.31 and SEQ.ID.NO.33) were transferred into the pcDNA3.1 His/V5 expression vector. Said vector allows the expression of heterologous proteins fused to a tail of 6 histidines as well as to the V5 epitope in eucaryotic cells. The different DNAs were produced by RT-PCR by using primers specific to the corresponding clones. These primers were constructed so as to remove the stop codon of each open reading frame or phase in order to allow the protein to be fused to the 6×HIS/Epitope V5 tail. In addition, the primers contained restriction sites adapted to the cloning in the expression vector. Care was taken to use, when amplifying, a high fidelity DNA polymerase (Pfu polymerase, Promega).

The transient expression of the Seq16 and 24 recombinant proteins was measured after transfection of the Seq16 and Seq24-pcDNA3.1-His/V5 constructions in COS1 cells, using Fugen 6 (Boehringer). The protein extracts of the culture media corresponding to times 24, 48 and 72 hours after transfection were analysed on acrylamide gel by staining with Coomassie blue or by Western blot using on the one hand an anti-6× histidine antibody or on the other hand Nickel chelate beads coupled to alcaline phosphatase.

These analyses showed the expression of said proteins in the cell culture media.

Example 7

Expression of Proteins in *E. coli*

7.1. Insertion of Coding Sequences into the pMAL-C2E Expression Vector

Proteins fused with the Maltose-Binding-Protein (MBP) were expressed in bacteria by using the pMAL-C2E (NEB) vector. The protein of interest then could be separated from the MBP thanks to a site separating the MBP from the protein, said site being specific to protease enterokinase.

In order to express optimally the 5 sequences examined, using the pMAL-C2E vector, PCR primer pairs complementary to 20 bases located upstream of the STOP codon and to 20 bases located downstream of the ATG of the open reading frame or phase were constructed. The amplified cDNA fragments only comprise the coding sequence of the target mRNA provided with its stop codon. The protein of interest was fused to MBP by its N-terminal end. On the other hand, since these primers contained specific restriction sites specific to the expression vector, it was possible to effect direct cloning of the cDNAs. The use of Pfu DNA polymerase (Promega) made it possible to amplify the cDNAs without having to fear for errors introduced into the amplified sequences.

The coding sequences of clones SEQ.ID.NO.7, SEQ.ID.NO.17, SEQ.ID.NO.26 and SEQ.ID.NO.31 were reconstructed in that way. Competent TG1 cells of *E. coli* were transformed using these constructions. Enzymatic digestions of these mini-preparations of plasmidic DNA made it possible to check that the majority of clones SEQ.ID.NO.7, SEQ.ID.NO.17, SEQ.ID.NO.26 and 31-p-MALC2-E effectively were recombinant.

7.2. Expression of Recombinant Proteins.

Starting from various constructions cloned in TG1 *E. coli* cells, the study of the expression of recombinant proteins fused with MBP was initiated for all sequences of interest (i.e. SEQ.ID.NO.7, SEQ.ID.NO.17, SEQ.ID.NO.26 and SEQ.ID.NO.33) except for SEQ.ID.NO.31. The culture of representative clones of SEQ.ID.NO.7, SEQ.ID.NO.17, SEQ.ID.NO.26 and SEQ.ID.NO.33 as well as negative controls (non recombinant plasmids) were started to induce the expression of recombinant proteins therein. These cultures were centrifuged and the pellets were separated from the media for being suspended in 15 mM pH7.5 Tris and passed through the French press. The analysis of these samples on 10% acrylamide gel coloured with Coomassie blue or by Western Blot using rabbit anti-MBP antibodies, showed the expression of recombinant proteins SEQ.ID.NO.7 (~50 kDa), SEQ.ID.NO.17 (~92 kDA), SEQ.ID.NO.26 (~80 kDA) and SEQ.ID.NO.31 (~67 kDa).

Example 8

Production of Antibodies

The SEQ.ID.NO.7, SEQ.ID.NO.17 and SEQ.ID.NO.26 protein were injected into groups of 4 mice with the purpose of producing antibodies directed against said proteins. The antigens were firstly injected with the complete Freund adjuvant. Two weeks later, a recall injection was made with incomplete Freund adjuvant. The sera of mice injected with SEQ.ID.NO.17 provided positive tests for anti-MBP antibodies.

Example 9

Ir-CPI (Sequence SEQ.ID.NO.7 without its Peptide Signal) Characteristics

Ticks and Tick Salivary Gland Extracts.

*I. ricinus* ticks were bred and maintained at the Institute of Zoology, University of Neuchatel (Switzerland). Colony founders were initially collected in the field near Neuchatel and have been maintained on rabbits and mice for over 20 years. Pairs of adult (female and male) ticks were allowed to anchor and feed on rabbits. For preparation of salivary gland extracts (SGE), Five-day engorged female ticks were dissected under the microscope. Salivary glands were harvested in ice cold phosphate saline buffer. Tissues were then disrupted and homogenized using a dounce. Samples were centrifuged for 5 minutes at 10,000 g and the supernatants were recovered and stored at −20° C.

Expression and Purification of Recombinant Ir-CPI in *E. coli*

The coding region of Ir-CPI cDNA was amplified using a forward primer corresponding to the predicted N-terminal end of mature Ir-CPI (5'-CGCGGATCCGCGGCCAACCA-CAAAGGTAGAGGG-3') and a reverse primer (5'-CCGCTCGAGCGGTTA-GACTTTTTTTGCTCTGCATTCC-3') corresponding to the C-terminal end of Ir-CPI including the stop codon. BamHI and XhoI restriction enzyme digestion sites were engineered into the 5' and 3' primers, respectively, to enable cloning into the pGEX-6P-1 expression vector (GE Healthcare, Sweden). PCR were performed in a 50 μl reaction volume containing 2.5 U of Taq polymerase (Takara Ex Taq, Takara, Japan), 10 pmoles of specific primers and 2.5 nmoles of each dNTP (Takara) in a standard buffer supplied by the manufacturer (Takara). PCR conditions were as follows: 1 cycle at 95° C. for 4 min followed by 30 cycles at 95° C. for 30 s/58° C. for 30 s/72° C. for 30 s followed by a final extension step at 72° C. for 10 min. PCR products were then purified by polyacrylamide gel electrophoresis followed by electroelution. The PCR product was cloned in-frame with GST in the pGEX-6P-1 vector at the BamHI and EcoRI restriction sites and transformed into *E. coli* strain BL21. Production of the recombinant protein was induced by the addition of IPTG at a final concentration of 1 mM and shaking at 37° C. for 2 h. Bacteria were harvested by centrifugation at 4000 g for 20 min and the pellet was dissolved in PBS. Lysates containing the expressed fusion protein were prepared using a French press. The resulting supernatant, which contained the GST-Ir-CPI fusion protein, was incubated with Glutathione Sepharose High Performance (GE Healthcare, Sweden) and washed. Ir-CPI was released by cleaving with PreScission protease according to the manufacturer's specifications and then purified to homogeneity by gel filtration chromatography using a HiLoad Superdex 75 column (GE Healthcare, Sweden).

Primary Hemostasis.

Human blood samples were collected from healthy donors in 3.8% trisodium citrate tubes. Global platelet function was measured on a PFA-100 machine (Dade Berhing) with collagen/epinephrine or collagen/ADP cartridge. The sample (1/10 protein in HBSS and 9/10 citrated whole blood) was aspirated through a capillary under steady high shear rates within 45 min of sample collection. A platelet plug was formed because of presence of the platelet agonist and the high shear rates, and this gradually occluded the aperture. The closure time was considered to be the time required to obtain full occlusion of the aperture.

Anticoagulant Activity.

The anticoagulant activities of Ir-CPI (presenting the sequence SEQ.ID.NO.7 without its peptide signal) were determined by four coagulation tests using a Start8 coagulometer. Human blood samples were collected from healthy donors in 3.8% trisodium citrate, and platelet-poor plasma was obtained by further centrifugation at 4000 g for 10 min.

Activated Partial Thromboplastin Time (aPTT)—Plasma (25 µl) and Ir-CPI (25 µl) were preincubated for 2 min at 37° C. Mixtures were activated for 4 min with 25 µl of Actin FSO (Dade Berhing, Germany). Clotting was initiated by adding 50 µl of 25 mM $CaCl_2$.

Prothrombin Time (PT)—Plasma (25 µl) and Ir-CPI (25 µl) were preincubated for 2 min at 37° C. Mixtures were activated for 4 min with 25 µl of Innovin® 1/200 (Dade Berhing, Germany). The clotting reaction was started by adding 50 µl of 25 mM $CaCl_2$.

Stypven Time—Plasma (25 µl), Hepes buffer (50 µl-Hepes 25 mM, Glycine 2%, NaCl 145 mM; pH 7.35) and Ir-CPI (25 µl) were preincubated for 2 min at 37° C. Clotting was initiated by the addition of 25 µl of LA 1 (Diagnostica Stago).

Thrombin Time—Plasma (25 µl), Hepes buffer (50 µl) and Ir-CPI (25 µl) were preincubated for 2 min at 37° C. Clotting was initiated by the addition of 25 µl of Thrombin (Diagnostica Stago).

Determination of Clot Lysis Times.

Clot lysis times on platelet-poor plasma were determined as described by Zouaoui Boudjeltia et al. (BMC Biotechnol. 2, 2:8, 2002). Plasma (100 µl), t-PA (25 µl) and Ir-CPI (100 µl) were preincubated for 2 min at 37° C. Clot formation was started by adding 100 µl (1.5 U/ml) of thrombin. The clot lysis time was measured with a semi-automatic instrument.

Assay of Alternative Pathway (AP) and Classical Pathway (CP) Complement Activity The capacity of Ir-CPI to inhibit the alternative complement pathway (AP) was determined according to Giclas PC (1997) Complement tests. In: Rose N R, Conway de Macario E, Folds J D, Lane H C & Nakamura R M, editors. Manual of clinical laboratory immunology, 5th edition, ASM Press, Washinton DC. pp. 181-186.

on red blood cells (RBC) from naïve healthy female New Zealand White rabbits. Briefly, fresh sera were diluted in gelatin-veronal-EGTA buffer (GVB) in microwell plates and washed RBCs were added. After 60 min of incubation at 37° C., supernatants were recovered to measure absorbance at 415 nm with a Model 680 microplate reader (Biorad). The volume of serum causing 50% hemolysis (AH50 value) was then determined by serial dilutions and used for further tests. The 100% lysis control was the total hemolysis produced by incubating 25 µl of MilliQ water. Background level (no hemolysis) was determined by incubating the erythrocytes in GVB buffer alone (without added serum). In order to test the inhibitory effect of Ir-CPI, 10 µg were introduced in the AP test. Ir-CPI was serially diluted in a final volume of 25 µl GVB in the presence of AH50 volume of the host serum under consideration. The assay then proceeded as described above. Percent inhibition of hemolysis was calculated as follows: ($OD_{415\ nm}$[serum+inhibitor]–$OD_{415\ nm}$ GVB control/$OD_{415\ nm}$[serum only]–$OD_{415\ nm}$ GVB control)×100.

The capacity of Ir-CPI to inhibit the classical complement pathway (CP) was also determined essentially as described by Colligan J E (1994) Complement. In: Coligan J E, Kruisbeek A M, Margulies D H, Shevach E M, Strober W, editors. Current Protocols in Immunology. Wiley/Interscience, New-York. pp. 13.1.1-13.2.7. Ready-to-use reagents were purchased from Institut Virion\Serion GmbH (Würtzburg, Germany). They included sheep erythrocytes pre-coated with rabbit anti-sheep RBC antibodies and Veronal Buffer pH 7.3 (VB) containing NaCl, $CaCl_2$ and $MgCl_2$. Briefly, diluted serum was incubated in the presence of antibody-coated sheep RBCs in microplates. Pooled human serum was first titrated to determine the volume that produces 50% hemolysis (CH50 value). Two-fold dilutions of Ir-CPI starting with 10 µg were prepared in VB buffer containing the equivalent of 0.8 µl human serum per test (total volume 25 µl). Pre-coated sheep erythrocytes were then added and the reaction performed as described above. Results were expressed as percent inhibition of hemolysis in the same was as for the AP pathway.

Thrombin Activity Profiles.

Materials. PPP reagent (5 pM TF and 4 µM PL in the final mixture), PPP LOW reagent (1 pM TF and 4 µM PL in the final mixture) and thrombin calibrator were purchased from Synapse BV. For each experiment, a fresh mixture of fluorogenic substrate/calcium chloride buffer solution was prepared as follows: 2275 µl of buffer (Hepes 20 mM, pH 7.35) containing 60 mg/ml of bovine serum albumin (Sigma) and 240 µl of 1 M calcium chloride were mixed with 60 µl of 100 mM DMSO solution of fluorogenic thrombin substrate (Z-Gly-Gly-Arg-AMC, Bachem). Actin FSO was obtained from Dade-Behring and was diluted 25 fold with distilled water.

Preparation of human plasma. Blood from male healthy volunteers, who were free from medication for at least two weeks, was taken by venipuncture and collected into 0.105 M sodium citrate (9:1 vol/vol). Platelet-poor plasma (PPP) was obtained by centrifugation at room temperature for 10 minutes at 2,500 g and was used immediately after centrifugation.

Calibrated automated thrombin activity measurement. Thrombin activity measurement was performed using the previously reported CAT procedure (Hemker et al. Pathophysiol. Haemost Thtomb. 2003, vol 33 (1) p 4-15). Briefly, 80 µl of PPP, 10 µl of PBS or Ir-CPI and 20 µl of PPP reagent, PPP LOW reagent or diluted Actin FS were mixed in a 96-wells microtiter plate (Thermo Immulon 2HB) and were incubated for 5 minutes at 37° C. The coagulation process was triggered by addition of 20 µl of substrate/calcium chloride buffer at 37° C. A calibration condition was also realized. In this later case, the same protocol as described above using PBS was followed but the activator was replaced by 20 µl of thrombin calibrator. The reaction of fluorogenic thrombin substrate hydrolysis was monitored on a microplate fluorometer Fluoroskan Ascent FL (Thermo Labsystems) with a 390/460 nm filter set (excitation/emission). Fluorescence was measured every 20 s for 60 min. The commercially available Thrombinoscope® software (Synapse BV) processed automatically the acquired data to give thrombin activity profile curves and measurement parameters (lag time and Cmax). Ten Ir-CPI concentrations ranging from 0.001 to 9.077 µM were tested in each experiment in triplicate.

Design of Small Interference RNA (siRNA).

Three siRNA were designed to target Ir-CPI mRNA and were synthesized by Eurogentec. These were 5'-CCAUGCAGAGCACGAAUUC-3',5'-GCACGAAUUCCGAGUUACU-3' and 5'-ACUACGUGCCAAGAGGAAU-3', respectively Ex Vivo Incubation of siRNA with Salivary Gland Extracts.

The salivary glands from 10 partially (5 days) fed female ticks were incubated for 6 h at 37° C. in the presence of 5 µg of siRNA negative control duplexes (Eurogentec, Belgium) or Ir-CPI siRNA or buffer alone in a total volume of 200 µl of incubation buffer TC-199 (Sigma) containing 20 mM MOPS, pH 7.0.

RT-PCR Analysis to Confirm Gene Silencing.

Messenger RNA from salivary gland extracts was isolated by oligo-dT chromatography (MicroFastTrack 2.0 mRNA Isolation Kit, Invitrogen). Reverse transcription was routinely performed in a 20 µl standard RT reaction mixture according to the manufacturer's instructions (First-Strand cDNA Synthesis System, Invitrogen) using the oligo dT primer. PCR was routinely performed in 50 µl of standard Takara buffer containing 2.5 U of Taq polymerase (Takara Ex Taq, Takara, Japan), 10 pmoles of each primer, and 2.5 nmoles of each dNTP (Takara). PCR cycling conditions were as follows: 30 cycles of 95° C. 30 s/58° C. 30 s/72° C. 30 s to 1 min 30 s preceded by an initial 4 min denaturation step at 95° C. and followed by a final 10 min extension at 72° C. Primers (sense-primer: 5'-ATGAAACTAACGATGCAGCT-GATC-3' and anti-sense primer: 5-TTA-GACTTTTTTTGCTCTGCATTCC-3') designed to amplify the Ir-CPI open reading frame were used to perform RT-PCR analysis of the transcripts. A pair of primers designed to amplify a 1,131 bp fragment from the actin open reading frame (sense-primer; 5'-ATGTGTGACGACGAGGTTGCC-3' and anti-sense primer; 5'-TTAGAAGCACTTGCGGTG-GATG-3') were used as controls. 10 µl of the PCR reactions were analyzed on a 2% agarose gel.

Activated Partial Thromboplastin Time (aPTT) and Prothrombin Time (PT) Assay to Confirm Gene Silencing.

Salivary gland extracts incubated with siRNA were assayed for anticoagulant activity in the aPTT or PT assay. SGE (5 µg) and plasma (25 µl) were preincubated for 2 min at 37° C. Mixtures were activated for 4 min with 25 µl of Actin FS for the aPTT (Dade Berhing) or Innovin 1/200 (Dade Berhing) for the PT. The clotting reaction was started by adding 50 µl of 25 mM $CaCl_2$.

Assay of the Inhibitory Effect of Ir-CPI on Coagulation Factors.

The inhibitory activity of Ir-CPI was examined on 9 serine proteases: procoagulant serine proteases (plasma kallikrein, FXIIa, FXIa, FIXa, FXa, thrombin and FVIIa) and fibrinolytic serine proteases (t-PA and plasmin). Each serine protease was preincubated with Ir-CPI in a 1:5 molar ratio for 5 min at 37° C., followed by the addition of the appropriate chromogenic substrate (final concentration 0.5 mM). Final concentrations in a total volume of 200 µl in 96-microwell-plates were as follows: kallikrein (3 nM)/S-2302, FXIIa (62.5 nM)/S-2302, FXIa (31.25 nM)/S2366, FIXa (500 nM)/Spectrozyme FIXa, FXa (10 nM)/S-2222, Thrombin (35 nM)/Spectrozyme TH, FT-FVIIa (100 nM)/Spectrozyme FVIIa, t-PA (35 nM)/Spectrozyme t-PA, plasmin (30 nM)/Spectrozyme PL. The kinetics of substrate hydrolysis were measured over 3 min. Chromogenic substrates S-2302, S-2366 and S-2222 were supplied by Chromogenix AB and Spectrozyme FIXa, TH, FVIIa, t-PA, PL were obtained from American Diagnostica Inc.

Assay of the Effects of Ir-CPI on Contact System Activation in Plasma

The effects of Ir-CPI on the activation of the contact system in human plasma were assessed from the generation of activated contact factors (factor XIa, factor XIIa and kallikrein). Human plasma was treated with acid to inactivate plasma serine protease inhibitors and then diluted 1:10 in buffer. Fifty microliters of diluted plasma were incubated with 20 µl of various concentrations of Ir-CPI for 5 min and then activated with 5 µl of aPTT reagent (Actin FS). After 10 min, a chromogenic substrate mixture at a final concentration of 0.5 mM and one or two inhibitors, Corn Trypsine Inhibitor (100 nM) or kallistop (50 µM), were added, and the amidolytic activity of the generated enzyme was determined at 405 nm. Sets of added chromogenic substrate and inhibitors were as follows: S-2366, Kallistop and CTI for factor XIa assay; S-2302 and Kallistop for factor XIIa assay; and S-2302 and CTI for kallikrein assay.

Assay of the Effect of Ir-CPI in a Reconstituted System.

A reconstitution assay of the kallikrein-kininogen-kinin system was performed using purified coagulation factors (FXIIa and prekallikrein). FXIIa (12.5 nM) was preincubated with Ir-CPI in Hepes buffer for 2 min at 37° C. Prekallikrein (12.5 nM) was added to the mixture, and then prekallikrein activation started. After 10 min, chromogenic substrate S-2302 was added, and the increase in absorbance at 405 nm was recorded over 3 min.

Reconstitution assays of the intrinsic coagulation pathway were performed using purified coagulation factors, factor XI/XIa and factor XII/XIIa. The effect of Ir-CPI on the activation of factor XI by factor XIIa was tested by incubating factor XI (15 nM), factor XIIa (60 nM) and Ir-CPI for 10 min at 37° C. After incubation, substrate S-2366 was added and the increase in absorbance was measured. The effect of Ir-CPI on the activation of factor XII by factor XIa was tested by incubating factor XI (15 nM), factor XIIa (60 nM) and Ir-CPI for 10 min at 37° C. After incubation, substrate S-2302 was added and the increase in absorbance was measured.

Reconstitution assays of the extrinsic coagulation pathway were performed using Actichrome TFPI Activity Assay and recombinant human TFPI according to the manufacturer's specifications (American diagnostica, Stamford).

Reconstitution assay of the fibrinolysis system was performed using purified fibrinolytic factors (t-PA and plasminogen). Plasminogen (500 nM) was preincubated with Ir-CPI for 2 min at 37° C. t-PA (500 nM) was added to the mixture, and plasminogen activation started. After 10 min, Spectrozyme PL chromogenic substrate was added, and the absorbance at 405 nm was measured over 3 min.

Binding Analysis Using Surface Plasmon Resonance.

The interaction between Ir-CPI and coagulation or fibrinolytic factors was monitored using a BIAcore 3000 instrument (BIAcore AB, Sweden). Ir-CPI (15 µM) was immobilized on the surface of a CM5 sensor chip in 10 mM acetate buffer, pH 5.0, by the amine coupling procedure according to the manufacturer's instructions. 1500 resonance units (RU) of immobilized Ir-CPI were used for the assay. To subtract the non-specific component from the apparent binding response, a blank flow cell was prepared using the same immobilizing procedure without Ir-CPI. Binding analyses were carried out using HBS buffer (HEPES mM, NaCl 150 mM, EDTA 3 mM; pH 7.4 with 0.005% surfactant P20) as running buffer at 25° C. 100 µl of each analyte (100 nM) was injected on the sensor chip at a flow rate of 70 µl/min. Association was monitored during an 84 injection of analyte. Dissociation was monitored for 3 min after return to the running buffer. Regeneration of the sensor chip surface was achieved with a pulse injection (15 µl) of 25 mM NaOH.

The kinetics of interactions between Ir-CPI and the four interacting factors were carried out after a new immobilization of Ir-CPI. The quantity of Ir-CPI immobilized for measurements of kinetics was deliberately maintained at a low level (to approximately 200 RU) to avoid the problems of limitation of the reaction by the process of mass-transport Independence with respect to differences in flow of the initial rate of connection, measured by linear regression at the start of the kinetics after injections of analytes with increasing flows (30 to 70 µl/min) confirmed that the reactions were not limited by such a process. Interaction kinetics were determined, for each analyte, with 6 different concentrations (from 5 nM to 300 nM). Binding data were analyzed using BIA evaluation software to determine the kinetic constants.

Assay of the effect of Ir-CPI on activation of the classical complement pathway by Hageman factor fragment (HFT).

The effects of Ir-CPI on activation of the classical complement pathway by Hageman factor fragment (HFf) were assessed using a hemolytic assay. HFf was activated by kallikrein and purified as described by Ghebrehiwet et al. HFf was incubated with various concentrations of Ir-CPI for 5 min. Then 1 µl of human serum and 50 µl of sensitized sheep erythrocytes (EA $10^8$/ml) were added and incubated for 60 min at 37° C. The reaction was stopped by addition of 150 µl of NaCl 0.9%, the mixture was centrifuged, and free hemoglobin was measured in the supernatant at 415 nm.

Determination of Radioactivity of $^{125}$I-Ir-CPI in Rat Blood.

$^{125}$I-labeled Ir-CPI was prepared by iodination with [$^{125}$I] sodium iodide in 20 mCi/mg of protein, using IODO-BEADS Iodination Reagent (PIERCE) according to the manufacturer's instructions. Free iodide was removed by extensive gel filtration on Sephadex G10.

The in vivo distribution of $^{125}$I-Ir-CPI in rat blood was evaluated after i.v. administration. Samples containing $10 \times 10^6$ cpm were resuspended in 200 µl of PBS and administered to rats. Blood was collected after 3, 20, 40 or 60 h by cardiac puncture in 3.8% trisodium citrate. Plasma was obtained by centrifugation, and aliquots of 500 µl were placed in glass test tubes. Radioactivity was determined in a gamma counter.

Ex Vivo Effect of Ir-CPI on aPTT, PT and Fibrinolysis.

The ex vivo effect of Ir-CPI on aPTT, PT and fibrinolysis tests was evaluated using a Start8 coagulometer. Ir-CPI was administered i.v. to rats and blood was collected after 5 min by cardiac puncture in 3.8% trisodium citrate. Platelet-poor plasma was obtained by centrifugation at 4000 g for 10 min. The aPTT, PT and fibrinolysis times were measured using the above-described procedures.

Bleeding Effect

A rat-tail-transection model was used to evaluate the effect of Ir-CPI on bleeding time. Rats were anesthetized and Ir-CPI was administered i.v. into the vena cava. After 5 min, the rat tail was cut 3 mm from the tip and carefully immersed in 10 ml of distilled water at room temperature. The hemoglobin content of the aqueous solution (absorbance at 540 nm) was used to estimate blood loss. Appropriate controls (i.v. injection of PBS) were run in parallel.

Complete Stasis Combined with Vessel Injury Induced Venous Thrombosis Model in the Rat Animals. Studies were carried out using male Sprague-Dawley OFA rats weighing 250 to 300 g obtained from Harlan (The Netherlands).

Thrombosis model. Thrombus formation was induced by a combination of complete stasis and vessel injury by ferric chloride according to the modification of the method described by Peternel et al. Thrombosis Research vol 115(6) p 527-534 (2005). Rats were anesthetized with pentobarbital sodium (70 mg/kg, IP). During anesthesia, the abdomen was opened by making an incision along the linea alba towards the sternum, followed by exposition of the posterior vena cava. Surgical threads, 1 cm apart, were placed loosely around the vena cava beneath the renal veins and above the bifurcation of the iliac veins to form a snare. Complete stasis was induced in the posterior vena cava by tightening the downstream snare firmly around the posterior vena cava. Simultaneously, a piece of filter paper (0.3×0.8 cm) saturated with 10% w/v ferric chloride solution was applied to the external surface of the posterior vena cava caudally of the ligature for 10 min. Ten min after the removal of the filter paper, the upstream snare was firmly tightened around the posterior vena cava and the rat was then euthanized. The ligated venous segment was excised, the thrombus removed, blotted of excess blood and immediately weighed. Results were expressed in milligrams of thrombus weight by kilograms of rat weight. Ir-CPI (0, 5-1000 µg/kg) or saline were injected in the left femoral vein 5 min prior to the induction of the thrombus formation.

Results

Protein Properties—Expression and Purification of Recombinant Ir-CPI.

Figure 3:
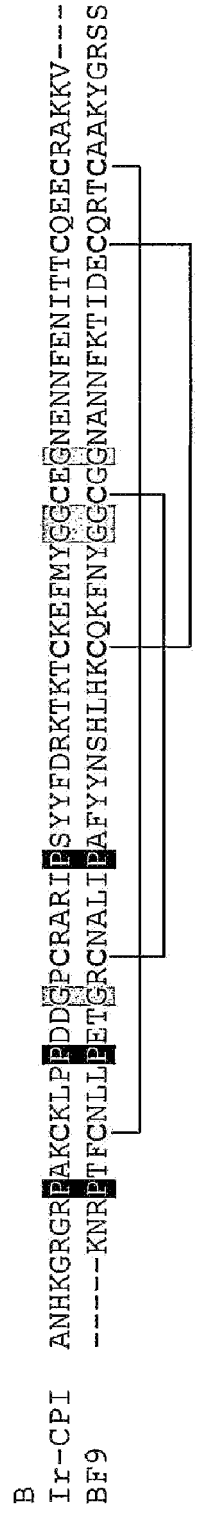
FIG. 3A represents amino acid sequence of Ir-CPI with its peptide signal (SEQ ID NO: 35).
FIG. 3B represents comparison of SEQ ID NO: 36 (Ir-CPI) with the kunitz-type chymotrypsin inhibitor from *Bungarus fasciatus* (BF9) (SEQ ID NO: 37). Some shared conserved residues are shaded (P, proline residue; G, glycine residue). Three disulphide bridges are represented. Finally, no consensus sites for N- and O-glycosylation were predicted in the sequence.

To identify cDNAs encoding proteins specifically expressed during the blood meal in the salivary glands of *I. ricinus* female ticks, a representational difference analysis subtractive library was set up using mRNAs extracted from salivary glands of unfed and 5-day-fed female *I. ricinus* ticks (Leboulle et al, 2002). One clone, formerly named SEQ.ID.NO.7 (GenBank accession no. AJ269641), was selected for further characterization of its recombinant protein, because of its similarity to the second kunitz-domain of the human tissue factor pathway inhibitor. Indeed, the amino acid sequence comprises the typical consensus kunitz motif F-x(3)-G-C-x(6)-[FY]-x(5)-C (FIG. 3A). The signal peptide sequence is in bold and underlined. The kuntiz motif sequence is shaded. Calculated MW and pI were 7,659 Da and 8.89, respectively. Moreover, SignalP and TargetP programs predicted a signal peptide cleavage site at position 23 and the absence of hydrophobic transmembrane region, suggesting that the protein was secreted. In order to find homologs, PDB was searched using the Blast algorithm. SEQ.ID.NO.7 displayed 30% identity and 39% similarity with the kunitz-type chymotrypsin inhibitor from *Bungarus fasciatus*. Both shared some conserved residues (e.g., proline and glycine, and 6 cysteine residues predicted to form three disulphide bridges; FIG. 3B). FIG. 3 represents amino acid sequence comparison of SEQ.ID.NO.7 (Ir-CPI with its peptide signal) with the kunitz-type chymotrypsin inhibitor from *Bungarus* fasciatus (BF9). Some shared conserved residues are shaded (P, praline residue; G, glycine residue). Three disulfide bridges are represented. Finally, no consensus sites for N- and O-glycosylation were predicted in the sequence.

In order to produce a recombinant form of SEQ.ID.NO.7, its coding sequence, without its expected cleavage site and its peptide signal was cloned in the expression vector pGEX-6P-1In-frame with the coding sequence of glutathione S-transferase and expressed in bacteria. Affinity purification followed by cleavage with PreScission protease and further fast protein liquid chromatography yielded pure protein.

Figure 4:
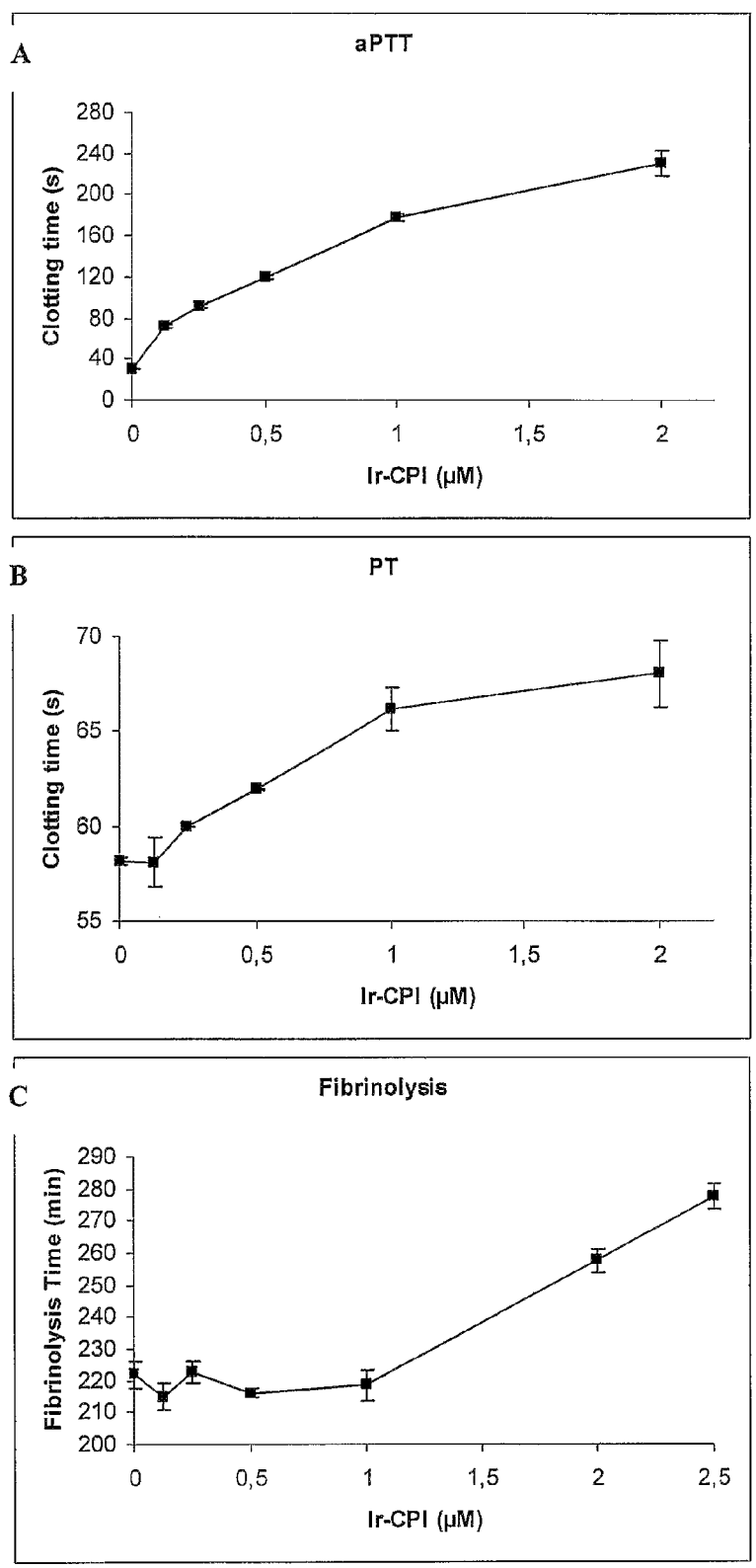
FIG. 4 represents the effects of Ir-CPI on aPTT, PT and Fibrinolysis times. Inhibitory activities of Ir-CPI was estimated on the intrinsic and extrinsic coagulation pathways, and on fibrinolysis.

Ir-CPI Prolongs Activated Partial Thromboplastin (aPTT), Prothrombin (Pt) and Fibrinolysis Times (FIG. 4)

The activity of recombinant Ir-CPI for "*Ixodes ricinus* Contact Phase Inhibitor" was analyzed on the three classical hemostasis pathways. No effect was observed on primary hemostasis for the two activators tested (collagen/epinephrine or collagen/ADP). For the two other pathways, the anticoagulant activity of Ir-CPI was determined by using four tests measuring plasma clotting times. Analysis of all the results showed that recombinant Ir-CPI prolongs aPTT (7.7 times at 2 μM) and PT (1.2 times at 2 μM) in a dose-dependent manner. The thrombin and stypven times were unchanged. The activity of Ir-CPI was also investigated on fibrinolysis. The results showed that the fibrinolysis time was slightly increased by 1.2 times in the presence of Ir-CPI at 2 μM. FIG. 4 represents the effects of Ir-CPI on aPTT, PT and Fibrinolysis times. Inhibitory activities of Ir-CPI was estimated on the intrinsic and extrinsic coagulation pathways, and on the fibrinolysis.

Natural Ir-CPI has an Anticoagulant Activity (FIG. 5)

Figure 5A:
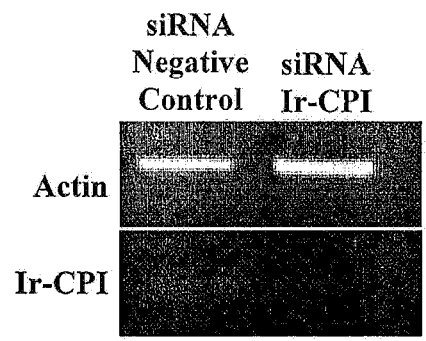
FIG. 5A represents evaluation of the Ir-CPI siRNA specificity by RT-PCR.
Figure 5B:
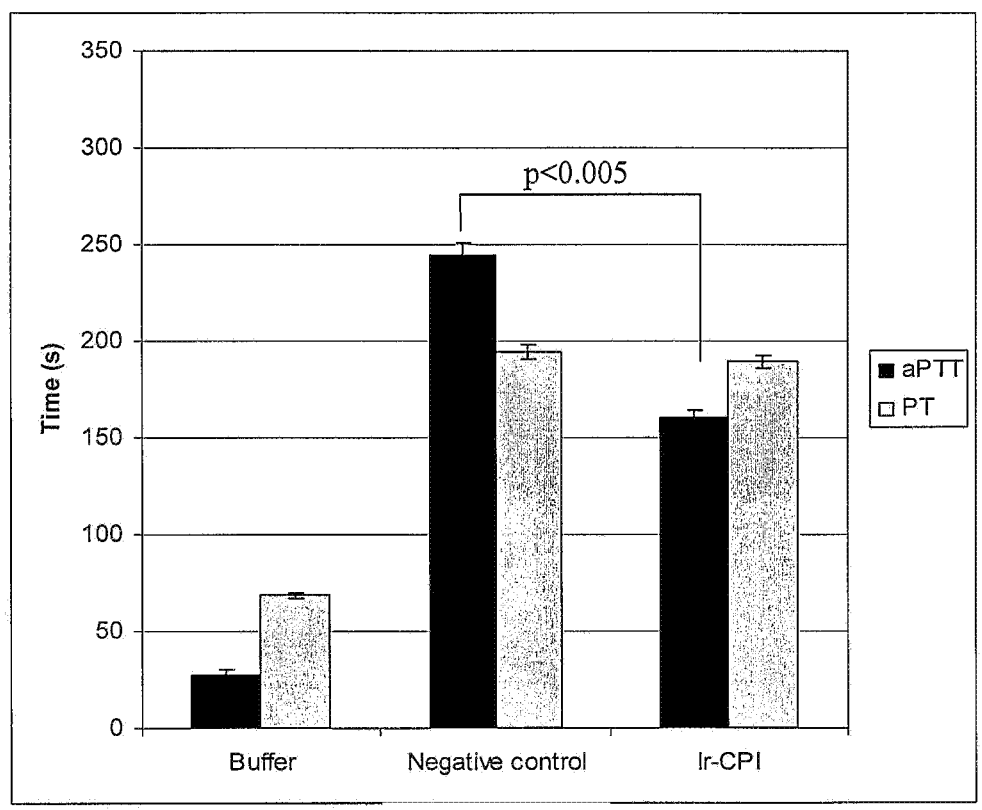
FIG. 5B represents the effect of Ir-CPI siRNA-treated salivary glad extracts on aPTT and PT.

The "RNA interference" method makes it possible to study the properties and role of a protein in its natural context. The inventors therefore synthesized siRNAs specific for Ir-CPI mRNA. The specificity of this siRNA was measured by RT-PCR on salivary gland mRNA extracts. The results showed that Ir-CPI mRNA was only silenced in SGE treated with Ir-CPI siRNA (FIG. 5A). FIG. 5A represents evaluation of the Ir-CPI siRNA specificity by RT-PCR. Salivary glands from 5-days fed female ticks were incubated with siRNA negative control duplexes, actin siRNA or Ir-CPI siRNA for 6 h at 37° C. RT-PCR assays were then realized by using action or Ir-CPI gene specific primers. The inventors then measured the effect on aPTT and PT of these siRNA-treated salivary gland extracts (FIG. 5B). FIG. 5B represents the effect of Ir-CPI siRNA-treated salivary gland extracts on aPTT and PT. Salivary glands were incubated either with negative control siRNA (negative control) or with Ir-CPI siRNA (Ir-CPI). The effect of these siRNA-treated salivary gland extracts on coagulation time (aPTT, PT) was then examined in aPTT and PT assays. Human plasma incubated with buffer served as a control (Buffer). Statistical significance was calculated by using one-way Anova and Student-Newman-Keuls test. Salivary gland extracts incubated with siRNA negative control had a mean aPTT of 217.2 s and PT of 125.8 s. When the same quantity of SGE was treated with Ir-CPI-specific siRNA, there was a major fall in aPTT and a minor fall in PT to values of 132.7 s and 121 s respectively.

Ir-CPI Inhibits Thrombin Generation (FIG. 6)

Figure 6A:
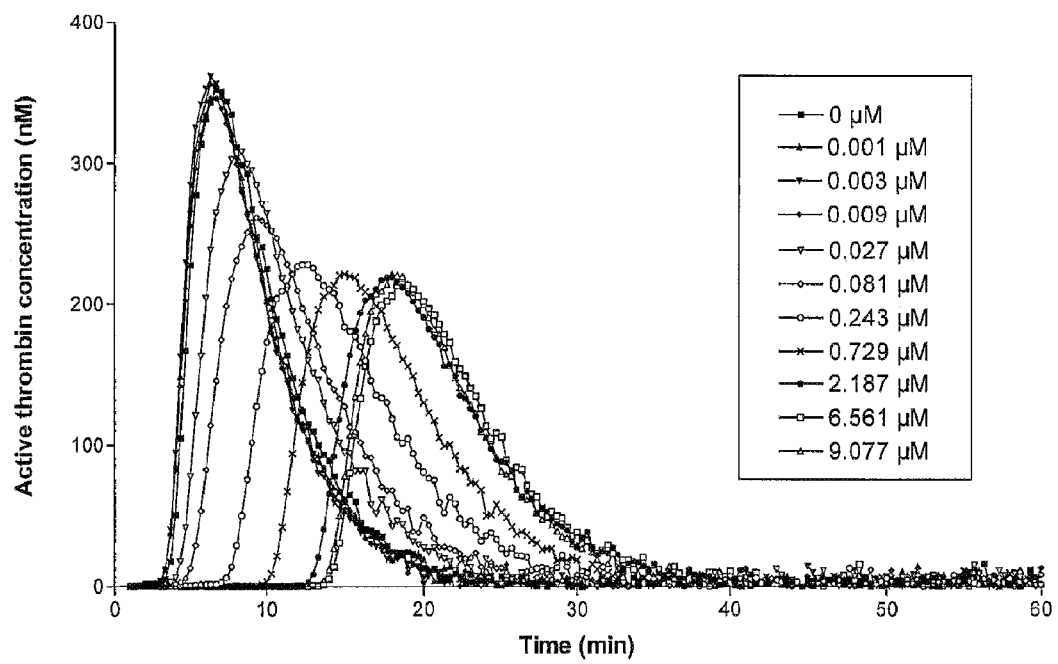
FIG. 6 represents the effect of Ir-CPI on thrombin activity profile during coagulation process induced by either ellagic acid and PL (A) or 5 µM TF and PL (B).

The effects of Ir-CPI were first investigated on thrombin activity during coagulation process induced by the intrinsic pathway by using a mixture of ellagic acid and phospholipids as trigger. Ir-CPI caused a dose-dependent prolongation of the lag time and a dose-dependent decrease of the maximal concentration of active thrombin (Cmax) compared to the control curve (i.e. without inhibitor) (FIG. 6A). At 9.077 μM, the lag time was prolonged 3.6 fold compared to the control curve. Regarding the Cmax, the effect was maximal at 2.187 μM and did not increase at higher concentrations (6.561 μM; 9.077 μM). At this concentration, the Cmax was reduced by 37% and the lag time was prolonged 2.7 fold.

Figure 6B:
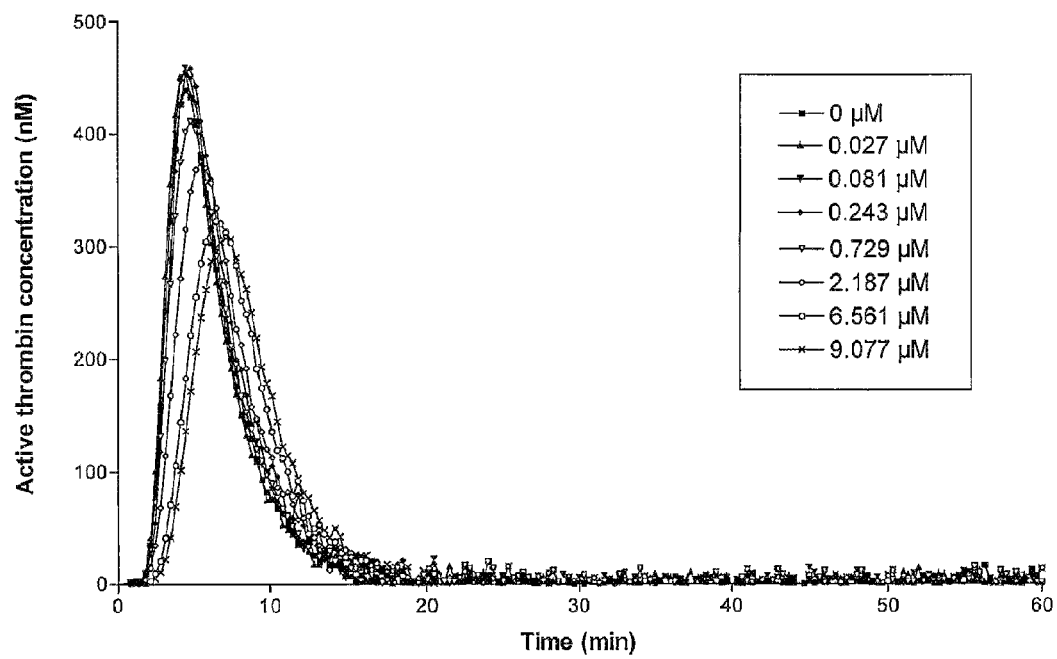

When coagulation cascade was triggered by the extrinsic pathway (5 μM of tissue factor (TF) and 4 μM of phospholipids (PL)), a slight dose-dependent decrease of the Cmax and a dose-dependent prolongation of the lag time were found (FIG. 6B). At 9.077 μM, the Cmax was reduced by 30% and the lag time was prolonged 1.6 fold. Similar results were obtained when using a lower concentration of TF (1 pM) and 4 μM PL. FIG. 6 represents the effect of Ir-CPI on thrombin activity profile during coagulation process induced by either ellagic acid and PL (A) or 5 pM TF and PL (B).

Taken together, these results confirm that Ir-CPI is a potent inhibitor of the thrombin generation induced by the intrinsic pathway, and to a lower extent by the extrinsic pathway.

Figure 7:
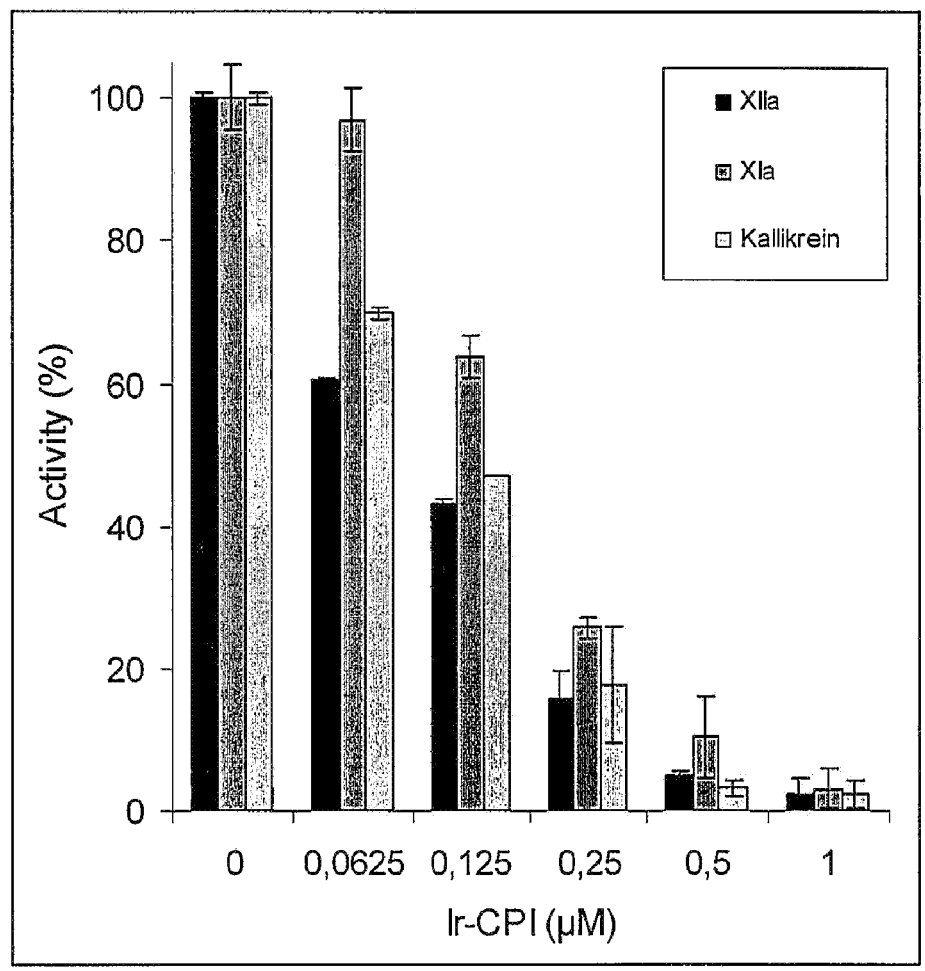
FIG. 7 represents the inhibitory effect of Ir-CPI on generation of factor XIIa, factor Xia and kallikrein in human plasma.
Figure 8:
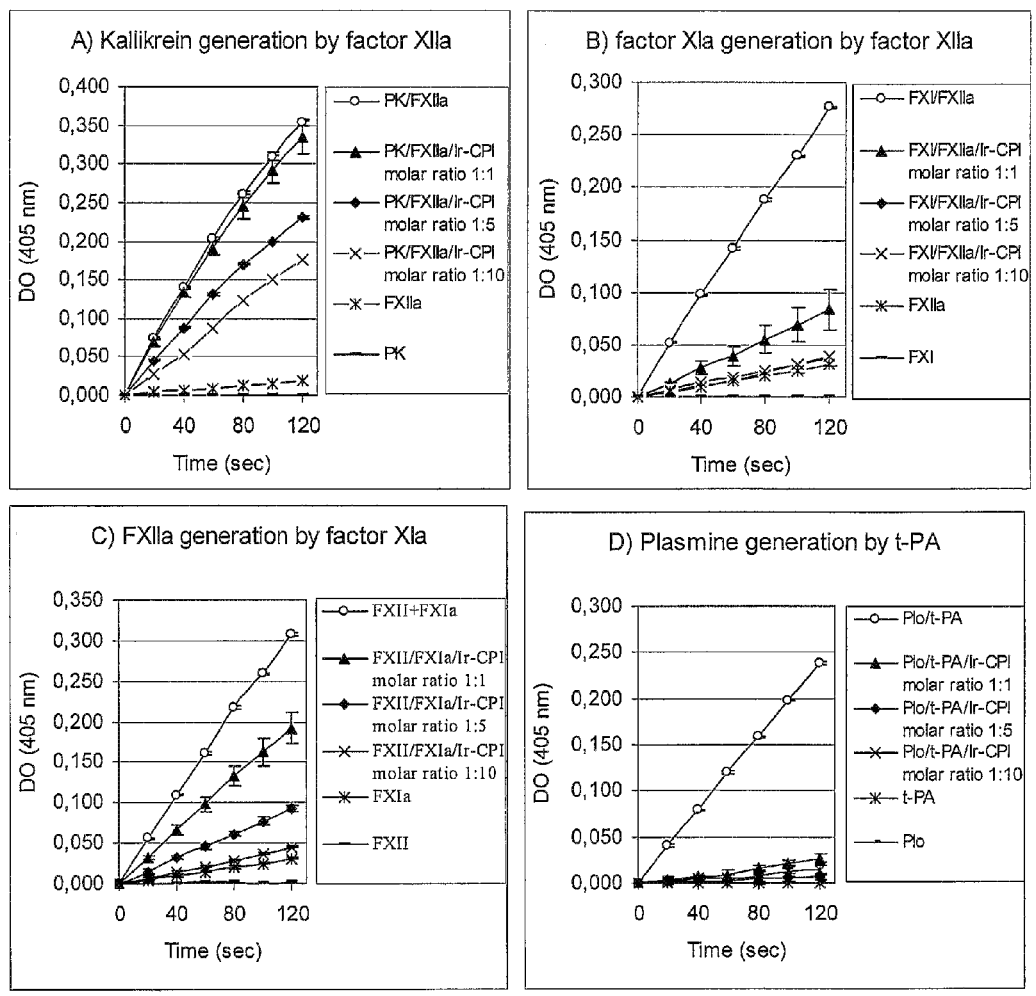
FIG. 8 A-D represents the inhibitory effect of Ir-CPI on reconstituted systems.

Ir-CPI Inhibits the Activation of Contact System Factors (FIGS. 7 and 8)

In order to determine the target of Ir-CPI, the effect of Ir-CPI on 7 procoagulant serine proteases (kallikrein, Factor XIIa, XIa, IXa, IXa, Xa, IIa and VIIa) and 2 fibrinolytic serine proteases (t-PA and plasmin) was measured with amidolytic tests using the specific substrate of each of these serine proteases. The results obtained did not show any effect of Ir-CPI protein on the amidolytic activity of these factors. FIG. 7 represents the inhibitory effect of Ir-CPI on generation of factor XIIa, factor XIa and kallikrein in human plasma. Diluted human plasma was incubated with various concentrations of Ir-CPI (0.0625, 0.125, 0.25, 0.5 and 1 μM), and the mixture was activated with aPTT reagent to initiate the contact system. The amidolytic activities of generated factor XIIa, Factor XIa and kallikrein were determiner by addition of chromogenic substrate, and increases in absorbance at 405 nm were recorded. Results are presented as the mean±SD of triplicate determinations.

The capacity of Ir-CPI protein to inhibit the activation of human plasma contact factors was then analyzed. In this experiment, human plasma was preincubated with Ir-CPI and then treated with a contact phase activator. The activation of contact factors (factor XIIa, XIa and kallikrein) was then evaluated by using the specific substrate of each factor. The results showed that Ir-CPI inhibits the generation of these three factors in a dose-dependent manner.

The effect of Ir-CPI was then examined in different reconstituted systems by using purified factors and their associated chromogenic substrates. In each of these experiments, the inventors analyzed the activation of a non-activated factor by an activated factor, in the presence or absence of Ir-CPI. The results showed that Ir-CPI inhibits the activation of prekallikrein into kallikrein by factor XIIa, the activation of factor XI into factor XIa by factor XIIa and the activation of factor XII into factor XIIa by factor XIa. On the contrary, Ir-CPI did not inhibit the activation of factor XII into factor XIIa by kallikrein or the activation of factor X into factor Xa by tissue factor complex/factor VIIa though it did inhibit the activation of plasminogen into plasmin by t-PA. FIG. 8 represents the inhibitory effect of Ir-CPI on reconstituted systems. The effect of Ir-CPI was examined in different reconstituted systems by using purified factors and their associated chromogenic substrates. The activation of a non-activated factor by an activated factor, in the presence or absence of Ir-CPI was analyzed in each experiment.

Taken overall, the results of these experiments show that Ir-CPI has a major effect on the activated factors participating in the contact phase of coagulation.

Figure 9:
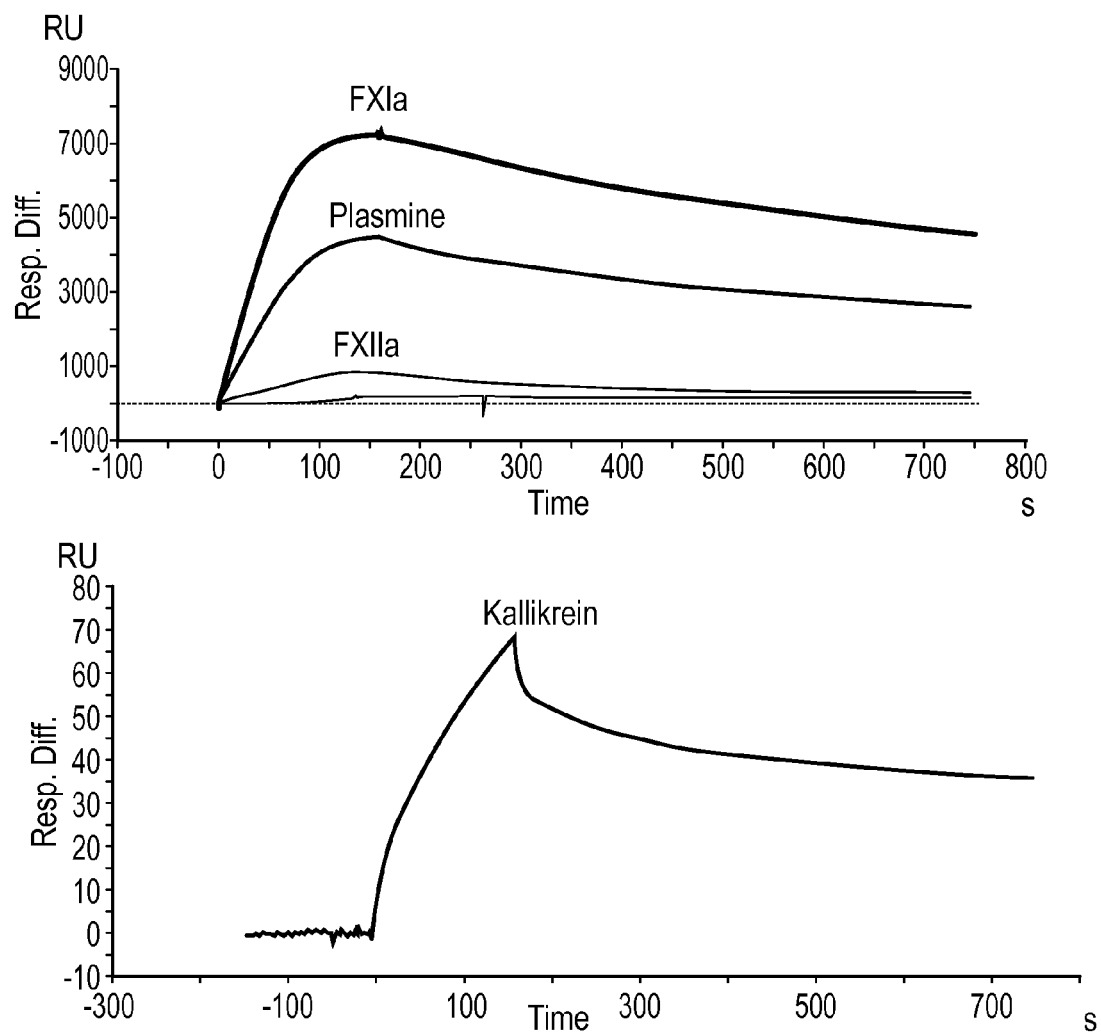
FIG. 9 represents sensorgrams for interactions between coagulation factors and immobilized Ir-CPI measured by surface plasmon resonance.

Ir-CPI Binds to Factor XIa, fXIIa, Kallikrein and Plasmin (FIG. 9)

The ability of Ir-CPI to bind a (co)factor of coagulation or fibrinolysis was evaluated by surface plasmon resonance. The results demonstrated a specific interaction between Ir-CPI and four factors: fXIIa, fXIa, plasmin and kallikrein (FIG. 9). No interaction was observed for the other (co)factors tested (prekallikrein, HMWK, fXII, fXI, fIX, fIXa, fX, fXa, thrombin, fVIIa, t-PA and plasminogen). In FIG. 9, the unlabeled sensorgram in the top panel is representative of the results obtained for the (co)factors in which no interaction was observed. Moreover, the kinetics of interaction between Ir-CPI and the four target factors (XIIa, XIa, plasmin and kallikrein) were measured after a new immobilization of Ir-CPI. In experiments to determine the binding kinetics, the quantity of immobilized Ir-CPI was deliberately kept at a low level (approximately 200 RU) in order to avoid problems where the reaction rate is limited by mass-transport The initial binding rate was shown to be independent of variations in flow by linear regression measurements at the start of kinetics with injections of analytes at increasing flows from 30 to 70 µl/min, confirming that there was no limitation of the reaction. Interaction kinetics were determined for each analyte, at 6 different concentrations (from 5 nM to 300 nM). The kinetic data obtained were individually processed with BIA evaluation software in order to determine the kinetics constants. The results obtained in this way showed that the affinity constant (Kd) of Ir-CPI was similar for fXIIa, fXIa, and plasmin (about nM: from 1.81 to 5.89 nM) whereas it was lower for kallikrein (0.2 µM). FIG. 9 represents sensorgrams for interactions between coagulation factors and immobilized Ir-CPI measured by surface plasmon resonance. Ir-CPI was immobilized onto the surface of a sensor chip CM5 at level of 1500 resonance units (RUs). Contact factors (100 nM final concentration) were injected at a flow rate of 70 µl/min in HBS buffer, and association was monitored. After return to buffer flow, dissociation was monitored during 84 s. The sensor chip surface was regenerated by a pulse injection of 25 mM NaOH after each experiment.

Figure 10:
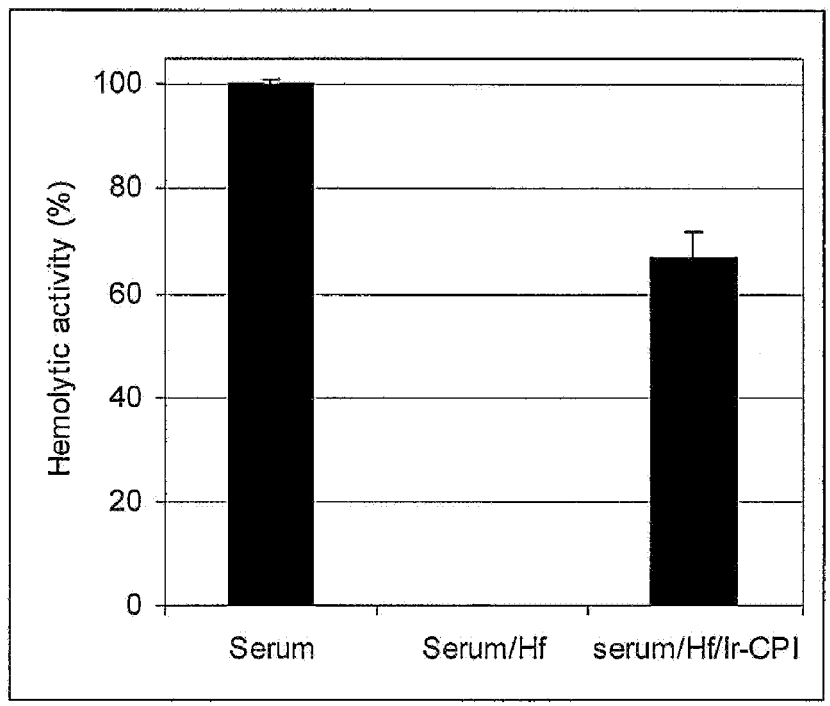
FIG. 10 represents inhibitory effect of Ir-CPI on the activation of the classical complement pathway by fragment f of factor XII (factor Hf).

Ir-CPI does not Inhibit the Classical and Alternative Complement Pathways; but Inhibits the Activation of Complement Factor C1 (FIG. 10)

The inventors also measured the direct effect of recombinant Ir-CPI on the alternative and classical complement pathways using red blood cell hemolysis tests. The results showed that there was no significant effect of Ir-CPI on these 2 pathways indicating that Ir-CPI does not directly interact with any of the factors of these 2 pathways. However, the inventors also examined the capacity of Ir-CPI to inhibit the activation of the classical complement pathway by fragment f of factor XII (factor Hf). In this experiment, Hf was preincubated with Ir-CPI before adding human serum. Under normal conditions, the incubation of Hf with normal serum leads to the sequential depletion of serum C1, C4, C2, and C3 following the activation of the classical complement pathway. In the presence of Ir-CPI, the inventors observed that Ir-CPI inhibits the initiation of the classical complement pathway via factor Hf. FIG. 10 represents inhibitory effect of Ir-CPI on the activation of the classical complement pathway by fragment f of factor XII (factor Hf). Hf was preincubated in the presence (Serum/Hf/Ir-CPI) or absence (Serum/Hf) of Ir-CPI before adding human serum. The mixture was then incubated with sensitized sheep erythrocytes for 60 min at 37° C. The reaction was stopped by addition of 150 µl of NaCl 0.9%, the mixture was centrifuged, and free hemoglobin was measured in the supernatant at 415 nm. Results are presented as the mean±SD of triplicate determinations.

Effect of Ir-CPI on Stasis-Induced Venous Thrombosis in Rats.

Figure 11:
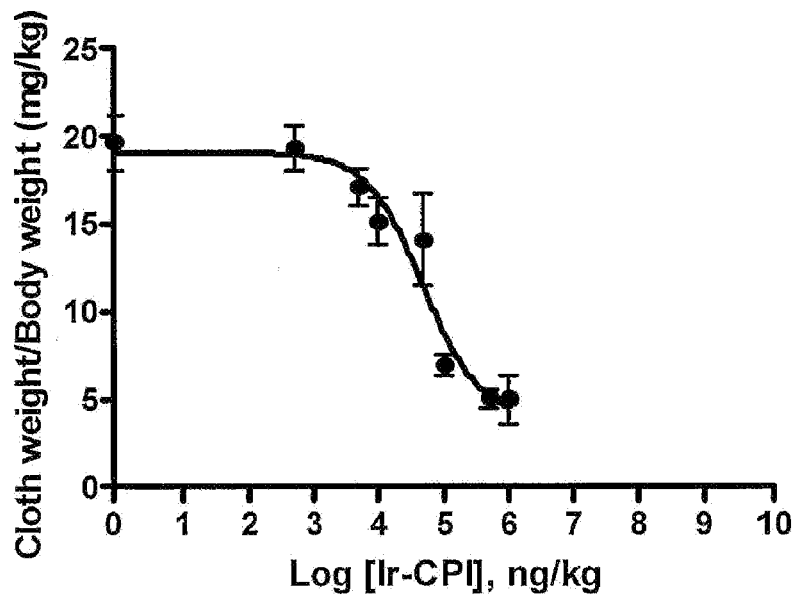
FIG. 11 represents the effect of Ir-CPI on stasis-induced venous thrombosis in rats.
Figure 12:
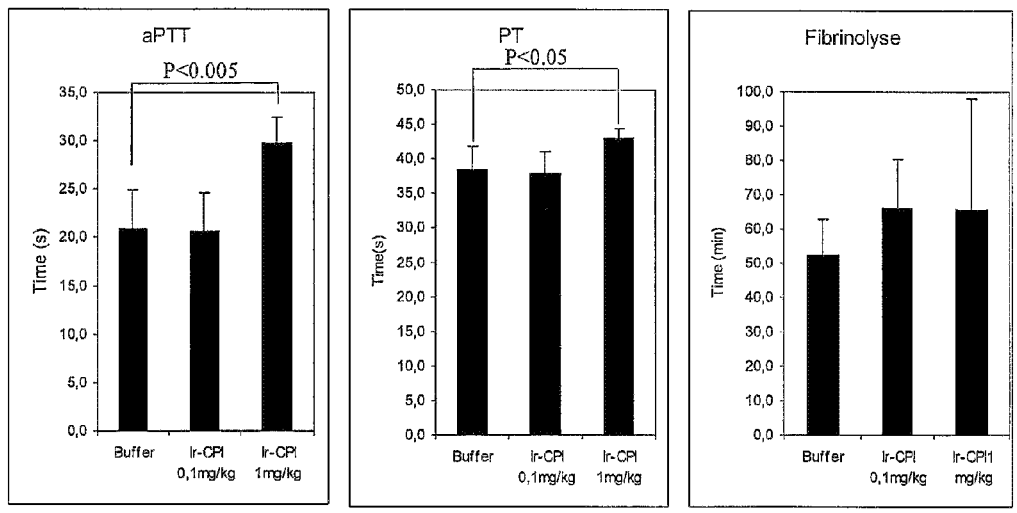
FIG. 12 represents ex vivo anticoagulant and fibrinolysis activity of Ir-CPI.

To determine whether Ir-CPI has an antithrombotic action in vivo, we used a venous thrombosis model in rats that combines stasis by vessel ligation and activation of thrombosis by severe endothelial damage and vessel occlusion with ferric chloride (see Materials and Methods). The control group showed 100% thrombus formation, with a mean thrombus weight of 19.6±1.6 mg/kg (n=6). In contrast, intravenous administration of Ir-CPI induced a progressive decrease in thrombus formation, with EC50 at about 50 µg/kg and with a maximum effect starting at 100 µg/kg (FIG. 11). FIG. 11 represents the effect of Ir-CPI on stasis-induced venous thrombosis in rats. Ir-CPI at the indicated doses was administered i.v. 5 min before induction of thrombosis by 10% FeCl3 and complete stasis, as described in Materials and methods. The control group received PBS instead of Ir-CPI. Each point represents mean±SD of five to six animals. In addition, the inventors also evaluated the half-life of Ir-CPI in vivo. A semi-quantitative estimate of Ir-CPI pharmacokinetics was obtained using $^{125}$I-Ir-CPI. The result shows that plasma $^{125}$I-Ir-CPI concentrations reached a peak 3 h after intravenous administration and were about 40.8%±9.9% of the maximum value 20 h after administration of the recombinant protein. The effects of Ir-CPI on ex vivo clotting assays were then tested. FIG. 12 represents ex vivo anticoagulant and fibrinolysis activity of Ir-CPI. Ir-CPI at the indicated concentrations was given intravenously to rats; after 5 min, blood was collected, and platelet-poor plasma was obtained. Coagulation tests aPTT, PT, fibrinolysis time were determined as described in Materials and methods. Each point represents mean±SD of five animals.

Figure 13:
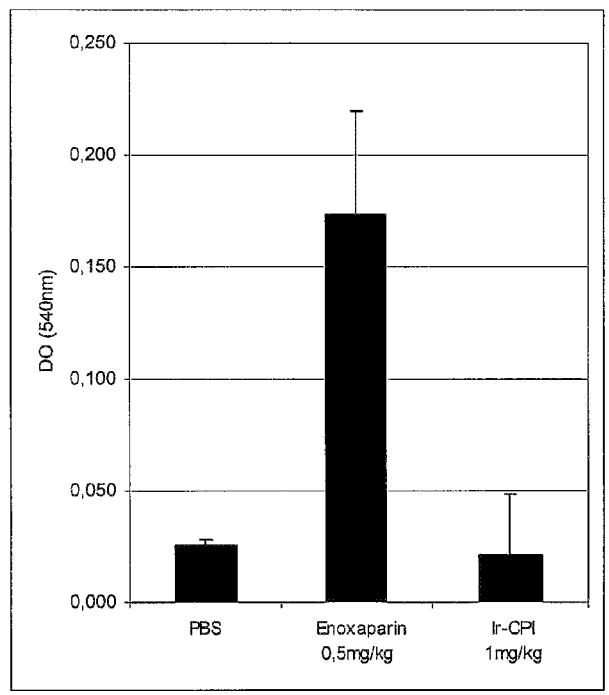
FIG. 13 represents the determination of the bleeding effect of Ir-CPI. Ir-CPI at the indicated dose was administered intravenously; after 5 min of administration, the rat tail was cut 3 mm from the tip.

FIG. 12 shows that aPTT values were similar in comparison with controls for Ir-CPI EC50 and 100 µg/kg doses whereas aPTT values were statistically higher in comparison with controls for Ir-CPI doses higher than 1 mg/kg, showing a ~1.4-fold increase in that case. In contrast, PT was only slightly affected by 1 mg/kg Ir-CPI. Moreover, this high dose of Ir-CPI had no effect on the fibrinolysis time. FIG. 13 represents the determination of the bleeding effect of Ir-CPI. Ir-CPI at the indicated dose was administered intravenously; after 5 min of administration, the rat tail was cut 3 mm from the tip. The tail was carefully immersed in 10 ml of distilled water at room temperature, and blood loss (hemoglobin content) was estimated at 540 nm after 60 min. The absorbance detected for a group that received PBS or Enoxaparin instead of Ir-CPI was taken as controls. Results represent the mean±SD of five animals. Finally, the bleeding effect of Ir-CPI was evaluated using a tail-transection model (FIG. 13); no statistically significant blood loss was observed 5 min after administration of 1 mg/kg Ir-CPI.

The coagulation cascade occurring in mammalian plasma involves a large number of plasma proteins that participate in a stepwise manner and eventually lead to the generation of thrombin. This enzyme then converts fibrinogen to an insoluble fibrin clot. Blood coagulation starts immediately after damage to the vascular endothelium and uncovering of the subendothelial structures. Contact phase proteins include the zymogens, factor XII, prekallikrein, factor XI and the cofactor, high molecular weight kininogen (HMWK). Factor XII autoactivates when bound to polyanionic surfaces, with conversion of factor XII to factor XIIa. Surface-bound activated factor XII then converts prekallikrein into kallikrein by cleavage of a single peptide bond. However, once small amounts of kallikrein are formed, there is rapid conversion of surface-bound factor XII to factor XIIa, resulting in strong positive feedback on the system. During activation of proenzymes, factor XII may also be activated during proteolysis by kallikrein leading to the production of a series of active enzymes formed by successive cleavages. Kallikrein first cleaves surface bound single-chain factor XII into a two-chain active α-factor XIIa. The newly formed α-factor XIIa has the same molecular weight as zymogen but is composed of a heavy chain of 50 kDa and a light chain of 28 kDa. The intrinsic coagulation pathway is initiated by cleavage of factor XI into activated factor XI (factor XIa) by α-factor XIIa. The heavy chain may be further cleaved into a series of lower molecular-weight forms of activated XII, known as Hageman factor fragment (HFf), all of which retain activity in terms of conversion of prekallikrein to kallikrein but lose the ability to activate factor XI. Similarly, HFf will not activate zymogen factor XII and therefore does not participate in autoactivation.

It later became clear that activation of the contact-phase system plays an essential role in fibrinolysis as it results in the activation of plasmin and pro-urokinase.

Serine protease, which is generated after initiation of the intrinsic pathway, also influences complement. Thus, plasmin, factor HFf, and kallikrein are responsible for activation of the C1r and C1s subunits of the first complement component, which are precursors of serine proteinases in the classic activation pathway and factor B, which is a proform of the serine proteinase of the alternative complement activation pathway.

Moreover, kallikrein is an activator of prorenin and is responsible for kinin formation. The contact phase has therefore been shown to initiate activation not only of the coagulation system but also of all the other proteolytic systems in blood plasma: kallikrein-kinin, complement, fibrinolytic, and renin-angiotensin systems. HFf can also activate factor VII, the proenzyme initiating the extrinsic coagulation pathway, dependent on tissue factor (TF).

Many blood-sucking ectoparasites synthesize substances to thwart the defense mechanisms of the hosts on which they feed. In order to effectively acquire and digest their blood meal, ticks must adapt to their host's defense systems and produce a certain number of salivary substances capable of modulating the host immune responses and maintaining blood in a sufficiently fluid state to acquire this meal.

The hemostatic system is composed of a network of factors, and the activation of each pathway may be induced in many different ways. Ticks however are confronted with the problem of redundancy as it is not sufficient to specifically inhibit a single factor as another pathway may take its place and activate blood clotting. However, the long parallel tick/host evolution has allowed ticks to confront such a system by producing several compounds with an anti-hemostatic activity.

When ticks take a blood meal, the action of the chelicerae and insertion of the hypostome into the host skin causes damage to the epidermis and dermis with rupture of local blood vessels thereby activating the contact phase pathway. Few inhibitors that act contact phase pathway have so far been discovered. Haemaphysalin is an inhibitor of the kallikrein-kinin system with two kunitz domains discovered in *Haemaphysalis longicornis* (Kato et al., (*Thrombosis haemostasis*, vol 93 p 359-367) 2005a). It appears that this molecule binds via its C terminal domain to the cell binding domains of high molecular weight kininogen and also that of fXIIa, which prevents the activation stages of the compounds of the contact system (Kato et al., (*Journal of Biochemistry* vol 38 (3) p 225-235) 2005b).

Ir-CPI is a low molecular weight protein that plays a major role in the tick blood meal by interfering with the activated factors involved in the contact phase of the coagulant balance. Such an inhibitor is not unexpected as the tick uses its chelicerae, pedipalps and hypostome during feeding. These cause extensive damage to the tissues surrounding the bite site by locally breaking the vessels and establishing a nutrition cavity rich in cells and in host blood factors. This phenomenon leads to the activation of contact phase factors.

Autoactivation of factor XII into factor XIIa usually occurs during the contact phase. This may therefore trigger both the intrinsic coagulation pathway by activating factor XI and also an inflammatory process by activating prekallikrein into kallikrein. Then, once activated, kallikrein releases bradykinin from high molecular weight kininogen. Bradykinin is an endogenous polypeptide comprising nine amino-acids. Bradykinin is one of the most potent vasodilators known which increases capillary permeability and promotes the development of edema. In addition to kallikrein, other tissue or plasma proteases are capable of cleaving bradykinin and others kinins. Plasmin, which is responsible for lysis of the fibrin clot, releases not only bradykinin but also its derivatives. Moreover, factor XIIa, XIa, and kallikrein are also capable of converting plasminogen into plasmin. By directly acting on factors XIIa and XIa, Ir-CPI blocks the intrinsic coagulation pathway; but also prevents the formation of kallikrein which plays an active role in the amplification process of these two factors. The inhibition of kallikrein production makes it possible to prevent the initiation of an inflammatory process by bradykinin release. Moreover, bradykinin production is also blocked by direct inhibition of plasmin and indirect inhibition of factor XIIa, XIa and kallikrein which are no longer capable of activating plasminogen into plasmin.

Factor XIIa also has an important role in the activation of the complement system. Factor XIIa can activate C1r and to a lesser extent C1s, the first element of the complement cascade. The hemolysis assay of the classical complement pathway using sheep red blood cells demonstrated the capacity of Ir-CPI to inhibit the initiation of this pathway by factor XIIa via factor Hf.

Moreover, deficiencies in these factors (XII, XI and prekallikrein) do not give rise to clinical situations that may be explained by impaired clotting or fibrinolysis. The coagulation balance of factor XII-knockout mice and fXII-deficient patients is not disturbed in any way and is similar to that observed in wild mice and healthy patients. On the other hand, fXII-KO mice are protected from thrombus formation, an essential element in venous thrombosis, cerebral ischemia and arterial thrombosis. The preclinical evaluation of Ir-CPI in 2 models of venous thrombosis suggests that Ir-CPI may therefore mirror the situation in KO mice by preventing clot formation without interfering with the clotting equilibrium (aPTT, PT and fibrinolysis were unchanged at the effective dose) or with the bleeding time. Ir-CPI therefore provide an excellent therapeutic tool by protecting patients at risk from diseases such as pulmonary embolism, cerebral ischemia or deep vein thrombosis.

We claim:

1. A method of inhibiting factor XIIa bound to a polyanionic surface, comprising causing the factor XIIa bound to the polyanionic surface to contact an isolated fusion protein which comprises an isolated polypeptide having at least 95% sequence identity to the amino acid sequence of SEQ ID NO:36 fused to a heterologous polypeptide, wherein said polypeptide has a kunitz-type-protease-inhibitor (KPI) domain, wherein the KPI domain of the polypeptide comprises Phe at position corresponding to position 40 of SEQ ID NO:36, Gly at position corresponding to position 44 of SEQ ID NO:36; Cys at position corresponding to position 45 of SEQ ID NO:36, Phe at position corresponding to position 52 of SEQ ID NO:36, and Cys at position corresponding to position 58 of SEQ ID NO:36.

2. The method of claim 1, wherein the isolated polypeptide is modified by or linked to at least one substitution group.

3. A method of inhibiting thrombus formation in the blood of a human patient, the method comprising:
   (A) a method of inhibiting thrombus formation in the blood of a human patient wherein the blood contacts an exposed structure other than the patient's endothelium, the method comprising introducing to the patient's blood a sufficient amount to inhibit thrombus formation of an isolated fusion protein which comprises a polypeptide having at least 95% sequence identity to the amino acid sequence of SEQ ID NO:36 fused to a heterologous polypeptide, wherein said polypeptide has a kunitz-type-protease-inhibitor (KPI) domain, wherein the KPI domain of the polypeptide comprises Phe at position corresponding to position 40 of SEQ ID NO:36, Gly at position corresponding to position 44 of SEQ ID NO:36; Cys at position corresponding to position 45 of SEQ ID NO:36, Phe at position corresponding to position 52 of SEQ ID NO:36, and Cys at position corresponding to position 58 of SEQ ID NO:36; or
   (B) a method of inhibiting thrombus formation, wherein the formation is inhibited after cutting the patient's vasculature, comprising cutting the patient's vasculature and introducing to the patient's blood flow a sufficient amount to inhibit thrombus formation of an isolated fusion protein which comprises a polypeptide having at least 95% sequence identity to the amino acid sequence of SEQ ID NO:36 fused to a heterologous polypeptide, wherein said polypeptide has a kunitz-type-protease-inhibitor (KPI) domain, wherein the KPI domain of the polypeptide comprises Phe at position corresponding to position 40 of SEQ ID NO:36, Gly at position corresponding to position 44 of SEQ ID NO:36; Cys at position corresponding to position 45 of SEQ ID NO:36, Phe at position corresponding to position 52 of SEQ ID NO:36, and Cys at position corresponding to position 58 of SEQ ID NO:36.

4. The method of claim 3, wherein the polypeptide is modified by or linked to at least one substitution group.

5. A method of inhibiting the contact phase pathway, comprising:
   causing a human's blood to contact a sufficient amount to inhibit the contact phase pathway of an isolated fusion protein which comprises a polypeptide having at least 95% sequence identity to the amino acid sequence of SEQ ID NO:36 fused to a heterologous polypeptide, wherein said polypeptide has a kunitz-type-protease-inhibitor (KPI) domain, wherein the KPI domain of the polypeptide comprises Phe at position corresponding to position 40 of SEQ ID NO:36, Gly at position corresponding to position 44 of SEQ ID NO:36; Cys at position corresponding to position 45 of SEQ ID NO:36, Phe at position corresponding to position 52 of SEQ ID NO:36, and Cys at position corresponding to position 58 of SEQ ID NO:36; and
   exposing the human's blood to a trigger selective for the contact phase pathway.

6. The method of claim 5, wherein the blood to which the isolated fusion protein is administered is venous blood.

7. The method of claim 5, wherein the isolated fusion protein is administered as a pharmaceutical composition comprising a pharmaceutical carrier and the polypeptide.

8. The method of claim 5, wherein the isolated fusion protein is administered by injection.

9. The method of claim 8, wherein the causing contact comprises administering to the human's blood a pharmaceutical composition comprising the isolated fusion protein and an anti-oxidant, buffer, bacteriostat, or solute that renders the composition isotonic with the blood.

10. The method of claim 5, wherein the polypeptide is selected from the group consisting of a polypeptide having up to 3 amino acid substitutions relative to the amino acid sequence of SEQ ID NO:36, a polypeptide having up to 3 amino acid deletions relative to the amino acid sequence of SEQ ID NO:36, and a polypeptide having up to 3 amino acid additions relative to the amino acid sequence of SEQ ID NO:36.

11. The method of claim 5, wherein the KPI domain comprises the amino acid sequence of amino acid residues 40 to 58 of SEQ ID NO:36.

12. The method of claim 5, wherein the polypeptide further comprises Cys at a position corresponding to position 12 of SEQ ID NO:36, Cys at a position corresponding to position 21 of SEQ ID NO:36, Cys at a position corresponding to position 37 of SEQ ID NO:36, and Cys at a position corresponding to position 62 of SEQ ID NO:36.

13. The method of claim 5, wherein the polypeptide has the amino acid sequence of SEQ ID NO:36.

14. The method of claim 5, wherein the polypeptide is modified by or linked to at least one substitution group.

15. The method of claim 5, wherein the trigger comprises a polyanionic surface.

16. The method of claim 5, wherein the exposing comprising cutting the human's vasculature after the isolated fusion protein is administered.

17. The method of claim 5, wherein the causing contact comprises administering to the human's blood by injection a pharmaceutical composition comprising a pharmaceutical carrier and the isolated fusion protein.

18. The method of claim 15, wherein the polypeptide is modified by or linked to at least one substitution group.

19. A method of preventing clot formation in the blood of a human patient without interfering with the bleeding time, the method comprising:
  (A) a method of preventing clot formation in the blood of a human patient without interfering with the bleeding time, wherein the blood contacts an exposed structure other than the patient's endothelium, the method comprising introducing to the patient's blood a sufficient amount to inhibit thrombus formation of an isolated fusion protein which comprises a polypeptide having at least 95% sequence identity to the amino acid sequence of SEQ ID NO:36 fused to a heterologous polypeptide, wherein said polypeptide has a kunitz-type-protease-inhibitor (KPI) domain, wherein the KPI domain of the polypeptide comprises Phe at position corresponding to position 40 of SEQ ID NO:36, Gly at position corresponding to position 44 of SEQ ID NO:36; Cys at position corresponding to position 45 of SEQ ID NO:36, Phe at position corresponding to position 52 of SEQ ID NO:36, and Cys at position corresponding to position 58 of SEQ ID NO:36; or
  (B) a method of preventing clot formation in the blood of a human patient without interfering with the bleeding time, wherein the formation is inhibited after cutting the patient's vasculature, comprising cutting the patient's vasculature and introducing to the patient's blood flow a sufficient amount to inhibit thrombus formation of an isolated fusion protein which comprises a polypeptide having at least 95% sequence identity to the amino acid sequence of SEQ ID NO:36 fused to a heterologous polypeptide, wherein said polypeptide has a kunitz-type-protease-inhibitor (KPI) domain, wherein the KPI domain of the polypeptide comprises Phe at position corresponding to position 40 of SEQ ID NO:36, Gly at position corresponding to position 44 of SEQ ID NO:36; Cys at position corresponding to position 45 of SEQ ID NO:36, Phe at position corresponding to position 52 of SEQ ID NO:36, and Cys at position corresponding to position 58 of SEQ ID NO:36.

* * * * *